US008481297B2

(12) United States Patent
van den Pol et al.

(10) Patent No.: US 8,481,297 B2
(45) Date of Patent: Jul. 9, 2013

(54) COMPOSITIONS AND METHODS OF USE OF AN ONCOLYTIC VESICULAR STOMATITIS VIRUS

(75) Inventors: Anthony N. van den Pol, Branford, CT (US); Guido Wollmann, New Haven, CT (US)

(73) Assignee: Yale University, New Haven, CT (US)

( * ) Notice: Subject to any disclaimer, the term of this patent is extended or adjusted under 35 U.S.C. 154(b) by 654 days.

(21) Appl. No.: 12/683,973

(22) Filed: Jan. 7, 2010

(65) Prior Publication Data

US 2010/0172877 A1    Jul. 8, 2010

Related U.S. Application Data

(60) Provisional application No. 61/143,236, filed on Jan. 8, 2009.

(51) Int. Cl.
*C12N 7/00* (2006.01)
*A01N 63/00* (2006.01)

(52) U.S. Cl.
USPC ..................................... 435/235.1; 424/93.2

(58) Field of Classification Search
None
See application file for complete search history.

(56) References Cited

U.S. PATENT DOCUMENTS

| | | | |
|---|---|---|---|
| 5,571,711 A | 11/1996 | vanderBruggen | |
| 5,683,886 A | 11/1997 | vanderBruggen | |
| 6,428,968 B1 | 8/2002 | Molnar-Kimber | |
| 6,673,545 B2 | 1/2004 | Faris | |
| 6,677,157 B1 | 1/2004 | Cohen | |
| 6,699,475 B1 | 3/2004 | Panicali | |
| 7,192,580 B2 | 3/2007 | Atkins | |
| 7,306,902 B2 | 12/2007 | Thompson | |
| 7,429,481 B2 | 9/2008 | Bergman | |
| 7,470,426 B1 | 12/2008 | Roberts | |
| 7,595,042 B2 | 9/2009 | Groene | |
| 7,731,974 B2 | 6/2010 | Bell | |
| 7,778,962 B2 | 8/2010 | Shah | |
| 8,147,822 B1 * | 4/2012 | Bell et al. ...................... | 424/93.6 |
| 2004/0017067 A1 | 1/2004 | Daines | |
| 2004/0170607 A1 | 9/2004 | Bell | |
| 2007/0026012 A1 | 2/2007 | Delisa | |
| 2007/0218078 A1 | 9/2007 | Clarke | |
| 2009/0047234 A1 | 2/2009 | Touitou | |
| 2009/0175906 A1 | 7/2009 | Kalyan | |
| 2009/0252672 A1 | 10/2009 | Eddington | |

FOREIGN PATENT DOCUMENTS

| | | |
|---|---|---|
| GB | 2241703 | 9/1991 |
| WO | 9640039 | 12/1996 |
| WO | 0050900 | 8/2000 |
| WO | 2004085659 | 10/2004 |
| WO | 2010080909 | 7/2010 |
| WO | 2011032003 | 3/2011 |

OTHER PUBLICATIONS

Aghi, et al., "Viral vectors as therapeutic agents for glioblastoma", Curr. Opinion, 7:419-30 (2000).
Ahmed, et al., "Identification of a consensus mutation in M protein of vesicular stomatitis virus from persistently infected cells that affects inhibition of host-directed gene expression", Virology, 237:378-88 (1997).
Ahmed,et al., "Immune response in the absence of neurovirulence in mice infected with m protein mutant vesicular stomatitis virus", J. Virol., 82(18):9273-7 (2008).
Alcami, et al., "The vaccinia virus soluble alpha/beta interferon (IFN) receptor binds to the cell surface and protects cells from the antiviral effects of IFN", J. Virol., 74:11230-9 (2000).
Ando, et al., "Ganglioside GM2 on the K562 cell line is recognized as a target structure by human natural killer cells", Int. J. Cancer, 40:12-17 (1987).
Aungst, "Intestinal permeation enhancers", J. Pharm. Sci. 89(4):429-42 (2000).
Baldridge, et al., "Teratogenic effects of neonatal arenavirus infection on the developing rat cerebellum are abrogated by passive immunotherapy", Virol., 197:669-77 (1993).
Bandi, et al., "Inhibition of type III interferon activity by orthopoxvirus immunomodulatory proteins", J. Interferon Cytokine Res. 30:123-134 (2010).
Bast, et al., "A radioimmunoassay using a monoclonal antibody to monitor the course of epithelial ovarian cancer", N. Eng. J. Med., 309:883-7 (1983).
Bharatan, et al., "Differential susceptibility of pediatric sarcoma cells to oncolysis by conditionally replication-competent herpes simplex viruses", J. Pediatr. Hematol. Oncol. 24:447-53 (2002).
Bi, et al., "Vesicular stomatitis virus infection of the central nervous system activates both innate and acquired immunity", J. Virol., 69:6466-72 (1995).
Brown, et al., "Structural characterization of human melanoma-associated antigen p97 with monoclonal antibodies", J. Immunol., 127:539-46 (1981).
Chang, et al., "Frequent expression of the tumor antigen CAK1 in squamous-cell carcinomas", Int. J. Cancer, 51:548-54 (1992c).
Chang, et al., "Isolation and characterization of a monoclonal antibody, K1, reactive with ovarian cancers and normal mesothelium", Int. J. Cancer, 50:373-81 (1992b).
Christian, et al., "Host immune response to vesicular stomatitis virus infection of the central nervous system in C57BL/6 mice", Viral Immuno., 9:195-205 (1996).

(Continued)

*Primary Examiner* — Michael Burkhart
(74) *Attorney, Agent, or Firm* — Pabst Patent Group LLP

(57) ABSTRACT

Oncolytic VSV viruses have been developed as a strategy for combating cancer. The present invention includes mutant VSV that have one or more mutations in the nucleic acid sequence encoding the viral genome that increase the oncolytic potential of the virus. Pharmaceutical compositions including oncolytic virus disclosed herein are also provided. Pharmaceutical compositions containing virus and one or more excipients may be for systemic or local administration. Methods of administering an effective amount of the compositions for treating cancer are disclosed. Preferred routes of administration include intratumeral and intravenous injection, and intranasal delivery. Administration of the disclosed compositions containing oncolytic viruses may be coupled with surgical, radiologic, other therapeutic approaches to treatment of cancer. Methods of manufacturing mutant VSV viruses exhibiting desired properties include applying selective pressure, and through directed or random mutagenesis.

13 Claims, 10 Drawing Sheets

OTHER PUBLICATIONS

Cooper, et al., "Attenuation of recombinant vesicular stomatitis virus-human immunodeficiency virus type 1 vaccine vectors by gene translocations and g gene truncation reduces neurovirulence and enhances immunogenicity in mice", J. Virol., 82:207-19 (2008).
Coulon, et al., "Genetic evidence for multiple functions of the matrix protein of vesicular stomatitis virus", J. Gen. Viral., 71:991-6 (1990).
Datta, et al., "Sensitive detection of occult breast cancer by the reverse-transcriptase polymerase chain reaction", J. Clin. Oncol., 12:475-82 (1994).
Diallo, et al., "A high-throughput pharmacoviral approach identifies novel oncolytic virus sensitizers", Mol. Ther. 18:1123-9 (2010).
Duntsch, et al., "Recombinant vesicular stomatitis virus vectors as oncolytic agents in the treatment of high-grade gliomas in an organotypic brain tissue slice-glioma coculture model", J. Neurosurg., 100:1049-59 (2004).
Flanagan, et al., "Vesicular stomatitis viruses with rearranged genomes have altered invasiveness and neuropathogenesis in mice", J. Virol., 77:5740-8 (2003).
Gaddy, et al., "Vesicular stomatitis viruses expressing wild-type or mutant M proteins activate apoptosis through distinct pathways", J. Virol., 79:4170-9 (2005).
Gearhart, et al., "Serum neutralizing antibody titers in dairy cattle administered an inactivated vesicular stomatitis virus vaccine", J. Am. Vet. Med. Assoc., 191:819-22 (1987).
Gebauer, et al., "Tumor marker concentrations in normal and malignant tissues of colorectal cancer patients and their prognostic relevance", Anticancer Res., 17 (4B):2939-42 (1997).
Gerlinger, et al., "How Darwinian models inform therapeutic failure initiated by clonal heterogeneity in cancer medicine", Br. J. Cancer, 103:1139-43 (2010).
Gobet, et al., "The role of antibodies in natural and acquired resistance of mice to vesicular stomatitis virus", Exp. Cell Bio., 56:175-80 (1988).
Goodin, "Treatment of multiple sclerosis with human beta interferon", Int. MS J., 12:96-108 (2005).
Held, et al., "Characterization of melanoma cells capable of propagating tumors from a single cell", Cancer Res. 70:388-97 (2010).
Hirokawa, et al., "Neuroblastoma in an adult with a high serum level of carbohydrate antigen, CA125: report of a case", Surg. Today, 28:349-54 (1998).
Hoon, et al., "Ganglioside GM2 expression on human melanoma cells correlates with sensitivity to lymphokine-activated killer cells", Int. J. Cancer, 43:857-62 (1989).
Jackson, "Rabies.", Neurol Clin. 26:717-26 (2008).
Jager, et al., "Antigen-specific immunotherapy and cancer vaccines", Int. J. Cancer, 106:817-20 (2003).
Johnson, et al., "Neurovirulence properties of recombinant vesicular stomatitis virus vectors in non-human primates", Virology, 360:36-49 (2007).
Jones, et al., "Live attenuated recombinant vaccine protects nonhuman primates against Ebola and Marburg viruses", Nat. Med. 11:786-90 (2005).
Kawakami, et al., "Cloning of the gene coding for a shared human melanoma antigen recognized by autologous T cells infiltrating into tumor", Proc. Nat. Acad. Sci. USA, 91(9):3515-9 (1994).
Kennedy, et al., "A role for antibodies in tumor immunity", Int. Rev. Immunol., 22:141-72 (2003).
Kudoh, et al., "Preoperative determination of several serum tumor markers in patients with primary epithelial ovarian carcinoma", Gynecol. Obstet. Invest., 47:52-7 1999).
Li, et al., "GSK-3$^2$: a signaling pathway node modulating neural stem cell and endothelial cell interactions", Angiogenesis, 14:173-85 (2011).
Lloyd, et al., "Isolation and characterization of ovarian cancer antigen CA 125 using a new monoclonal antibody (VK-8): identification as a mucin-type molecule", Int. J. Canc., 71:842-50 (1997).
Lockwood, et al., "Decidual hemostasis, inflammation, and angiogenesis in pre-eclampsia", Semin. Thromb. Hemost. 37:158-64 (2011).
Long, et al., "Genetic and spectrally distinct in vivo imaging: embryonic stem cells and mice with widespread expression of a monomeric red fluorescent protein", BMC Biotechnol., 5:20 (2005).
Lundh, et al., "Non-lethal infection of aminergic reticular core neurons: age-dependent spread of ts mutant vesicular stomatitis virus from the nose", J. Neuropathol. Exp. Neurol., 47:497-506 (1988).
Lyles, "Cytopathogenesis and inhibition of host gene expression by RNA viruses", Microbiol. Mol. Biol. Rev., 64:709-24 (2000).
Meager, "Biological assays for interferons", J. Immunol. Methods, 261:21-36 (2002).
Meier, et al., "Prognostic significance of CA125 in patients with ovarian cancer and secondary debulking surgery", Anticancer Res., 17(4B):2945 (1997).
Muller, et al., "Functional role of type I and type II interferons in antiviral defense", Science, 264:1918-21 (1994).
Natali, et al., "Immunohistochemical detection of antigen in human primary and metastatic melanomas by the monoclonal antibody 140.240 and its possible prognostic significance", Cancer, 59:55-63 (1987).
Nguyen, et al., "Chemical targeting of the innate antiviral response by histone deacetylase inhibitors renders refractory cancers sensitive to viral oncolysis", PNAS, 105:14981-6 (2008).
Ohgaki, et al., "Population-based studies on incidence, survival rates, and genetic alterations in astrocytic and oligodendroglial gliomas", J. Neuropathol. Exp. Neurol., 64:479-89 (2005).
Otsuki, et al., "Histone deacetylase inhibitors augment antitumor efficacy of herpes-based oncolytic viruses", Mol. Ther. 16:1546-55 (2008).
Perry, et al., "The host type I interferon response to viral and bacterial infections", Cell Res., 5:407-422 (2005).
Plowman, et al., "Heregulin induces tyrosine phosphorylation of HER4/p180erbB4", Nature, 366:473-5 (1993).
Publicover, et al., "A single-cycle vaccine vector based on vesicular stomatitis virus can induce immune responses comparable to those generated by a replication-competent vector", J. Virol., 79:13231-8 (2005).
Qiao, et al., "Loading of oncolytic vesicular stomatitis virus onto antigen-specific T cells enhances the efficacy of adoptive T-cell therapy of tumors", Gene Ther., 15:604-16 (2008).
Randall, et al., "Interferons and viruses: an interplay between induction, signalling, antiviral responses and virus countermeasures", J. Gen. Virol. 89:1-47 (2008).
Reiss, et al., "Viral replication in olfactory receptor neurons and entry into the olfactory bulb and brain", Ann. N.Y. Acad. Sci., 855:751-61 (1998).
Reuter, et al., "Systemic immune deficiency necessary for cytomegalovirus invasion of the mature brain", J. Virol., 78:1473-87 (2004).
Roberts, et al., "Vaccination with a recombinant vesicular stomatitis virus expressing an influenza virus hemagglutinin provides complete protection from influenza virus challenge", J. Virol., 72:4704-11 (1998).
Ryder, et al., "Statistics for the molecular biologist: group comparisons", Curr. Protoc. Mol. Biol., Appendix 3: Appendix 3I (2001).
Sabin, et al., "influence of host factors on neuroinvasiveness of vesicular stomatitis virus : I. effect of age on the invasion of the brain by virus instilled in the nose", J. Exp. Med., 66:15-34 (1937).
Sadler, et al., "Interferon-inducible antiviral effectors", Nat. Rev. Immunol. 8:559-68 (2008).
Saha, et al., "Mother-to-baby transfer of humoral immunity against retrovirus-induced neurologic disorders and immunodeficiency", Virology, 198:129-37 (1994).
Sarandakou, et al., "Tumour-associated antigens CEA, CA125, SCC and TPS in gynaecological cancer", Eur. J. Gynaecol. Oncol., 19:73-7 (1998).
Sarandakou, et al., "Vaginal fluid and serum CEA, CA125 and SCC in normal conditions and in benign and malignant diseases of the genital tract", Acta Oncol., 36:755-9 (1997).
Schneider-Schaulies, et al., J. Neurovirol. 5:613-22 (1994).
Schnell, et al., "Construction of a novel virus that targets HIV-1-infected cells and controls HIV-1 infection", Cell, 90:849-57 (1997).
Shinozaki, et al., "Eradication of advanced hepatocellular carcinoma in rats via repeated hepatic arterial infusions of recombinant VSV", Hepatology, 41:196-203 (2005c).

Simon, et al., "Replication and propagation of attenuated vesicular stomatitis virus vectors in vivo: vector spread correlates with induction of immune responses and persistence of genomic RNA", J. Virol., 81:2078-82 (2007).
Studahl, et al., "Influenza virus and CNS manifestations", J. Clin. Virol. 28:28:225-32(2003).
Taniguchi, et al., "A weak signal for strong responses: interferon-alpha/beta revisited", Mol. Cell Biol. 2:378-86 (2001).
Trottier, et al., "VSV replication in neurons is inhibited by type I IFN at multiple stages of infection", Virology, 333:215-25 (2005).
Tsuchida, et al., "Gangliosides of human melanoma: GM2 and tumorigenicity", J. Natl. Cancer, 78:55-60 (1987).
Tsuchida, et al., "Gangliosides of human melanoma", J. Natl. Cancer, 78:45-54 (1987).
Van Den Bruggen, et al., "A gene encoding an antigen recognized by cytolytic T lymphocytes on a human melanoma", Science, 254:1643-7 (1991).
Van Den Pol, et al., "Cytomegalovirus induces interferon-stimulated gene expression and is attenuated by interferon in the developing brain", J. Virol. 81:332-48 (2007).
Van Den Pol, et al., "Viral strategies for studying the brain, including a replication-restricted self-amplifying delta-G vesicular stomatis virus that rapidly expresses transgenes in brain and can generate a multicolor golgi-like expression", J. Comp. Neurol., 516:456-81 (2009).
Wege, et al., "Coronavirus JHM-induced demyelinating encephalomyelitis in rats: influence of immunity on the course of disease", Prog. Brain Res. 59:221-231 (1983).
Yoshimura, et al., "Assessment of urinary beta-core fragment of human chorionic gonadotropin as a new tumor marker of lung cancer", Cancer, 73:2745-52 (1994).
Yoshino, et al., "Association of HER2/neu expression with sensitivity to tumor-specific CTL in human ovarian cancer", J. Immunol., 152:2393-400 (1994).
Adema, et al., "Molecular characterization of the melanocyte lineage-specific antigen gp100", J. Biol. Chem., 269(31):20126-20133 (1994).
Ahmed, et al., "Sensitivity of prostate tumors to wild type and M protein mutant vesicular stomatitis viruses", Virology, 330(1):34-49 (2004).
Akiyama, et al., "Genistein, a specific inhibitor of tyrosine-specific protein kinases", J. Biol. Chem., 262(12):5592-5595 (1987).
Alfthan, et al., "Elevation of free beta subunit of human choriogonadotropin and core beta fragment of human choriogonadotropin in the serum and urine of patients with malignant pancreatic and biliary disease", Cancer Res., 52:4628-4633 (1992).
Balachandran and Barber, "Vesicular stomatitis virus (VSV) therapy of tumors", IUBMB Life, 50:135-138 (2000).
Balachandran and Barber, "Defective translational control facilitates vesicular stomatitis virus oncolysis", Cancer Cell, 5(1):51-65 (2004).
Balachandran, et al., "Oncolytic activity of vesicular stomatitis virus is effective against tumors exhibiting aberrant p53, Ras, or myc function and involves the induction of apoptosis", J Virol, 75 (7):3474-3479 (2001).
Ball-Goodrich, and Tattersall, "Two amino acid substitutions within the capsid are coordinately required for acquisition of fibrotropism by the lymphotropic strain of minute virus of mice", J. Virol., 66:3415-3423 (1992).
Bantel-Schaal, "Adeno-assciated parvoviruses inhibit growth of cells derived from malignant human tumors", Int. J. Cancer, 45:190-194 (1990).
Barber, "Vesicular stomatitis virus as an oncolytic vector", Viral Immunol., 17 (4):516-527 (2004).
Barber, "VSV-tumor selective replication and protein translation", Oncogene, 24(52):7710-7719 (2005).
Bardelli, et al., "Mutational analysis of the tyrosine kinome in colorectal cancers", Science, 300(5621):949 (2003).
Barik and Banerjee, "Phosphorylation by cellular casein kinase II is essential for transcriptional activity of vesicular stomatitis virus phosphoprotein P", Proc. Nat. Acad. Sci. USA, 89:6570-6574 (1992).

Barnd, et al., "Specific, major histocompatibility complex-unrestricted recognition of tumor-associated mucins by human cytotoxic T cells", Proc. Nat. Acad. Sci. USA, 86 (18):7159-7163 (1989).
Boldogkoi, et al., "Evaluation of pseudorabies virus as a gene transfer vector and an ocolytic agent for human tumor cells", Anticancer Res., 22:2153-2159 (2002).
Chang, et al., "Characterization of the antigen (CAK1) recognized by monoclonal antibody K1 present on ovarian cancers and normal mesothelium", Cancer Res., 52(1):181-186 (1992).
Chang, et al., "Molecular cloning of mesothelin, a differentiation antigen present on mesothelium, mesotheliomas, and ovarian cancers", Proc. Natl. Acad. Sci. USA, 93(1):136-140 (1996).
Chiocca, "Oncolytic viruses", Nat. Rev. Cancer, 2(12):938-950 (2002).
Chiocca, et al., "Viral therapy for glioblastoma", Cancer J., 9:167-179 (2003).
Chowdhury, et al., "Isolation of a high-affinity stable single-chain Fv specific for mesothelin from DNA-immunized mice by phage display and construction of a recombinant immunotoxin with anti-tumor activity", Proc. Natl. Acad. Sci. USA, 95(2):669-674 (1998).
Clarke, et al., "Synergistic attenuation of vesicular stomatitis virus by combination of specific G gene truncations and N gene translocations", J. Virol., 81(4):2056-2064 (2007).
Dalton and Rose, "Vesicular stomatitis virus glycoprotein containing the entire green fluorescent protein on its cytoplasmic domain is incorporated efficiently into virus particles", Virology, 279(2):414-421 (2001).
Das and Pattnaik, "Phosphorylation of vesicular stomatitis virus phosphoprotein P is indispensable for virus growth", J. Virol., 78(12):6420-6430 (2004).
De Mattos, et al., "Rhabdoviruses", In Fields of Virology (Knipe, et al., Eds.), Lippincott Williams and Wilkins: Philadelphia, pp. 1245-1277, 2001.
Disis, et al., "Existent T-cell and antibody immunity to HER-2/neu protein in patients with breast cancer", Cancer Res., 54(1):16-20 (1994).
Drake, et al., "Mutation rates among RNA viruses", Proc. Natl. Acad. Sci. USA, 96(24):13910-13913 (1999).
Dupont, et al., "Tumor-selective gene transduction and cell killing with an oncotropic autonomous parvovirus-based vector", Gene Ther., 7:790-796 (2000).
Ebert, et al., "Systemic therapy of experimental breast cancer metastases by mutant vesicular stomatitis virus in immune-competent mice", Cancer Gene Ther., 12(4):350-358 (2005).
Flanagan, et al., "Rearrangement of the genes of vesicular stomatitis virus eliminates clinical disease in the natural host: new strategy for vaccine development", J. Virol., 75 (13):6107-6114 (2001).
GenBank Accession No. FJ478454 "Recombinant vesicular stomatitis Indiana virus rVSV-G/GFP, complete genome", 5 pages, submitted Nov. 20, 2008, first published Dec. 23, 2008, accessed Jan. 3, 2011.
GenBank Accession No. Q8B0H8 "RecName: Full=Phosphoprotein; Short=Protein P; AltName: Full=NS; AltName: Full=Protein M1", 2 pages, submitted Nov. 11, 2005, first published May 15, 2007, accessed Jan. 3, 2011.
GenBank Accession No. Q8B0H3 "RecName: Full=Phosphoprotein; Short=Protein P; AltName: Full=NS; AltName: Full=Protein M1", 2 pages, submitted Nov. 11, 2005, first published May 15, 2007, accessed Jan. 3, 2011.
GenBank Accession No. Q8B0I3 "RecName: Full=Phosphoprotein; Short=Protein P; AltName: Full=NS; AltName: Full=Protein Ml", 2 pages, submitted Nov. 11, 2005, first published May 15, 2007, accessed Jan. 3, 2011.
GenBank Accession No. P03520 "RecName: Full=Phosphoprotein; Short=P protein; AltName: Full=Protein Ml", 3 pages, submitted Jul. 21, 1986, first published Apr. 24, 1993, accessed Jan. 3, 2011.
GenBank Accession No. P04879 "RecName: Full=Phosphoprotein; Short=Protein P; AltName: Full=Protein Ml", 2 pages, submitted Aug. 13, 1987, first published Apr. 24, 1993, accessed Jan. 3, 2011.
GenBank Accession No. P04880 "RecName: Full=Phosphoprotein; Short=Protein P; AltName: Full=Protein Ml", 2 pages, submitted Aug. 13, 1987, first published Apr. 24, 1993, accessed Jan. 3, 2011.

Germano, et al., "Adenovirus/herpes simplex-thymidine kinase/ganciclovir complex: preliminary results of a phase I trial in patients with recurrent malignant gliomas", J. Neurooncol., 65:279-289 (2003).

Gold and Freedman, "Demonstration of Tumor-Specific Antigens in Human Colonic Carcinomata by Immunological Tolerance and Absorption Techniques.", J. Exp. Med., 121:439-462 (1985).

Gromeier, et al., "Intergeneric poliovirus recombinants for the treatment of malignant glioma", Proc. Natl. Acad. Sci. USA, 97:6803-6808 (2000).

Herrero, et al., "Parvovirus H-1 infection of human glioma cells leads to complete viral replication and efficient cell killing", Int. J. Cancer, 109:76-84 (2004).

Ishii, et al., "Frequent co-alterations of TP53, p16/CDKN2A, p14ARF, PTEN tumor suppressor genes in human glioma cell lines", Brain Pathol., 9:469-479 (1999).

Jan, et al., "Sindbis virus entry into cells triggers apoptosis by activating sphingomyelinase, leading to the release of ceramide", J. Virol., 74:6425-6432 (2000).

Jarvis, et al., "Human cytomegalovirus infection of caco-2 cells occurs at the basolateral membrane and is differentiation state dependant", J. Virol., 73:4552-4560 (1999).

Kahn, et al., "Recombinant vesicular stomatitis virus expressing respiratory syncytial virus (RSV) glycoproteins: RSV fusion protein can mediate infection and cell fusion", Virology, 254(1):81-91 (1999).

Kawakami, et al., "Cloning of the gene coding for a shared human melanoma antigen recognized by autologous T cells infiltrating into tumor", Proc. Nat. Acad. Sci. USA, 91 (9):3515-3519 (1994).

Lawson, et al., "Recombinant vesicular stomatitis viruses from DNA", PNAS, 92 (10):4477-4481 (1995).

Legrand, "MVM(p) Ns-2 protein expression is required with NS-1 for maximal cytotoxicity in human transformed cells", Virology, 195:149-155 (1993).

Lehmann, et al., "Discrimination between benign and malignant cells of melanocytic lineage by two novel antigens, a glycoprotein with a molecular weight of 113,000 and a protein with a molecular weight of 76,000.", Cancer Res., 47(3):841-845 (1987).

Lehmann, et al., "MUC18, a marker of tumor progression in human melanoma, shows sequence similarity to the neural cell adhesion molecules of the immunoglobulin superfamily.", Proc. Natl. Acad. Sci. USA, 86(24):9891-9895 (1989).

Lenard, "Host cell protein kinases in nonsegmented negative-strand virus (mononegavirales) infection.", Pharmacol. Ther., 83(1):39-48 (1999).

Lewis, et al., "Alpha-virus-induced apoptosis in mouse brains correlates with neurovirulence", J. Virol., 70:1828-1835 (1996).

Lichty, et al., "Vesicular stomatitis virus: re-inventing the bullet", Trends Mol. Med., 10(5):210-216 (2004).

Lun, et al., "Effects of Intravenously Administered Recombinant Vesicular Stomatitis Virus (VSV"M51) on Multifocal and Invasive Gliomas", J. Natl. Can. Instit., 98(21):1546-1557 (2006).

Lun, et al., "Targeting human medulloblastoma: oncolytic virotherapy with myxoma virus is enhanced by rapamycin", Cancer Res., 67(18):8818-8827 (2007).

Lyles and Rupprecht, "Rhabdoviridae", Fields Virology, 5th ed. (Knipe and Howley, eds.), Lippincott Williams and ilkins: Philadelphia, pp. 1363-1408, 2007.

Ma, et al., "Intratumoral gene therapy of malignant brain tumor in a rat model with angiostatin delivered by adeno-associated viral (AAV) vector", Gene Ther., 9:2-11 (2002).

McManus, et al., "Human chorionic gonadotropin in human neoplastic cells.", Cancer Res., 36(9 pt 2):3476-3481 (1976).

Mizuno, et al., Adeno-associated virus vector containing the herpes simplex virus thymidine kinase gene causes complete regression of intracerebrally implanted human gliomas in mice, in conjunction with ganciclovir administration, Jpn. J. Cancer Res., 89:76-80 (1998).

Nister, et al., "Expression of messenger RNAs for platelet-derived growth factor and transforming growth factor-alpha and their receptors in human malignant glioma cell lines", Cancer Res., 48:3910-3918 (1988).

Obuchi, et al., "Development of recombination vesicular stomatitis viruses that exploit defects in host defense to augment specific oncolytic activity", J. Virol., 75:8843-8856 (2003).

Okuma, et al., "Recombinant vesicular stomatitis viruses encoding simian immunodeficiency virus receptors target infected cells and control infection", Virology, 346(1):86-97 (2006).

Ozduman, et al., "Systemic vesicular stomatitis virus selectively destroys multifocal glioma and metastatic carcinoma in brain", J. Neurosci., 28 (8):1882-1893 (2008).

Özduman, et al., "Peripheral immunization blocks lethal actions of vesicular stomatitis virus within the brain", J. Virol., 83(22):11540-11549 (2009).

Pardridge, "Drug and gene delivery to the brain: the vascular route", Neuron, 36(4):555-558 (2002).

Parsons, et al., "Colorectal cancer: mutations in a signalling pathway", Nature, 436(7052):792 (2005).

Phuong, et al., "Use of a vaccine strain of measles virus genetically engineered to produce carcino-embryonic antigen as a novel therapeutic agent against glioblastoma multi-forme", Cancer Res., 63:2462-2469 (2003).

Prieto, et al., "Development of new expression vector based on pseudorbies virus amplicons: application to human insulin expression", Virus Res., 89:123-129 (2002).

Publicover, et al., "Characterization of nonpathogenic, live, viral vaccine vectors inducing potent cellular immune responses", J. Virol., 78(17):9317-9324 (2004).

Publicover, et al., "Rapid pathogenesis induced by a vesicular stomatitis virus matrix protein mutant: viral pathogenesis is linked to induction of tumor necrosis factor alpha", J. Virol., 80(14):7028-7036 (2006).

Pulkkanen and Yla-Herttuala, "Gene therapy for malignant glioma: current clinical status", Mol. Ther., 12(4):585-598 (2005).

Puumalainen, et al., "Gene therapy for malignant glioma patients", Adv. Exp. Med. Biol., 451:505-509 (1998).

Rainov and Ren, "Oncolytic viruses for treatment of malignant brain tumours.", Acta Neurochir Suppl., 88:113-123 (2003).

Ramsburg, et al., "A vesicular stomatitis virus recombinant expressing granulocyte-macrophage colony-stimulating factor induces enhanced T-cell responses and is highly attenuated for replication in animals", J. Virol., 79(24):15043-15053 (2005).

Roberts, et al., "Complete protection from papillomavirus challenge after a single vaccination with a vesicular stomatitis virus vector expressing high levels of L1 protein.", J. Virol., 78(6):3196-3199 (2004).

Roberts, et al., "Attenuated vesicular stomatitis viruses as vaccine vectors", J. Virol., 73(5):3723-3732 (1999).

Rose, et al., "An effective AIDS vaccine based on live attenuated vesicular stomatitis virus recombinants", Cell, 106(5):539-549 (2001).

Rose, et al., "Primary structure of the human melanoma-associated antigen p97 (melanotransferrin) deduced from the mRNA sequence", Proc. Natl. Acad. Sci. USA, 83(5):1261-1265 (1986).

Scanlan, et al., "The cancer/testis genes: review, standardization, and commentary", Cancer Immun., 4:1 (2004).

Schlehofer, "The tumor suppressive properties of adeno-associated viruses", Matat. Res., 305:303-313 (1994).

Schnell, et al., "Requirement for a non-specific glycoprotein cytoplasmic domain sequence to drive efficient budding of vesicular stomatitis virus", EMBO Journal, 17(5):1289-1296 (1998).

Schnell, et al., "The minimal conserved transcription stop-start signal promotes stable expression of a foreign gene in vesicular stomatitis virus", J. Virol., 70 (4):2318-2323 (1996).

Schnell, et al., "Foreign glycoproteins expressed from recombinant vesicular stomatitis viruses are incorporated efficiently into virus particles", PNAS, 93 (21):11359-11365 (1996).

Shaughnessy, et al., "Parvoviral vectors for the gene therapy of cancer", Semin. Oncol., 213:159-171 (1996).

Shinozaki, et al., "Prophylactic alpha interferon treatment increases the therapeutic index of oncolytic vesicular stomatitis virus virotherapy for advanced hepatocellular carcinoma in immune-competent rats", J. Virol., 79(21):13705-13713 (2005).

Shinozaki, et al., "Treatment of multi-focal colorectal carcinoma metastatic to the liver of immune-competent and syngeneic rats by hepatic artery infusion of oncolytic vesicular stomatitis virus", Int. J. Cancer, 114(4):659-664 (2005).

Smith, et al., "Pseudorabies virus expressing enhanced green fluorescent protein: A tool for in vitro electrophysiological analysis of transsynaptically labeled neurons in identified central nervous system circuits", Proc. Natl. Acad. Sci., 97(16):9264-9269 (2000).

Spadafora, et al., "Constitutive phosphorylation of the vesicular stomatitis virus P protein modulates polymerase complex formation but is not essential for transcription or replication", J. Virol., 70(7):4538-4548 (1996).

Stojdl, et al., "VSV strains with defects in their ability to shutdown innate immunity are potent systemic anti-cancer agents", Cancer Cell, 4(4):263-275 (2003).

Stojdl, et al., "Exploiting tumor-specific defects in the interferon pathway with a previously unknown oncolytic virus", Nat Med, 6(7):821-825 (2000).

Sung, et al., "Combined VSV oncolytic virus and chemotherapy for squamous cell carcinoma", The Laryngoscope, 118(2):237-242 (2008).

Tesh, et al., "Ecologic studies of vesicular stomatitis virus. I. Prevalence of infection among animals and humans living in an area of endemic VSV activity", Am. J. Epidemiol., 90(3):255-261 (1969).

Timiryasova, et al., "Antitumor effect of vaccinia virus in glioma model", Oncol. Res., 11:133-144 (1999).

Topalian, et al., "Human CD4+ T cells specifically recognize a shared melanoma-associated antigen encoded by the tyrosinase gene", Proc. Natl. Acad. Sci. USA, 91(20):9461-9465 (1994).

Trowbridge and Omary, "Human cell surface glycoprotein related to cell proliferation is the receptor for transferrin", Proc. Natl. Acad. USA, 78 (5):3039-3043 (1981).

Tseng, et al., "Systemic tumor targeting and killing by Sindbis viral vectors", Nat. Biotechnol., 22:70-77 (2004).

Van Den Pol, et al., "Cytomegalovirus cell tropism, replication, and gene transfer in brain", J. Neurosci., 19:10948-10965 (1999).

Van Den Pol, et al., "Relative neurotropism of a recombinant rhabdovirus expressing a green fluorescent envelope glycoprotein", J. Virol., 76(3):1309-1327 (2002).

Vecil and Lang, "Clinical trials of adenoviruses in brain tumors: a review of Ad-p53 and oncolytic adenoviruses", J. Neurooncol., 65:237-246 (2003).

Vijayasardahi, et al., "The melanoma antigen gp75 is the human homologue of the mouse b (brown) locus gene product", J. Exp. Med., 171(4):1375-1380 (1990).

Vilchez and Butel, "SV40 in human brain cancers and non-Hodgkin\s lymphoma", Oncogene, 22:5164-5172 (2003).

Wagner and Rose, "Rhabdoviridae: the Viruses and Their Replication", Fields Virology, Lippincott-Raven Press: Philadelphia, pp. 561-575, 1996.

Wang, et al., "Mutational analysis of the tyrosine phosphatome in colorectal cancers", Science, 304(5674):1164-1166 (2004).

Weber, et al., "Tumor immunity and autoimmunity induced by immunization with homologous DNA", J. Clin. Invest, 102(6):1258-1264 (1998).

Wollmann, et al., "Targeting human glioblastoma cells: comparison of nine viruses with oncolytic potential", J. Virol., 79(10):6005-6022 (2005).

Wollmann, et al., "Variable deficiencies in the interferon response enhance susceptibility to vesicular stomatitis virus oncolytic actions in glioblastoma cells but not in normal human glial cells", J Virol, 81(3):1479-1491 (2007).

Wollmann, et al., "Some attenuated variants of vesicular stomatitis virus show enhanced oncolytic activity against human glioblastoma cells relative to normal brain cells", J. Virol., 84(3):1563-1573 (2009).

Wrensch, et al., "Epidemiology of primary brain tumors: current concepts and review of the literature", Neuro-oncology, 4:278-299 (2002).

Wu, et al., "Oncolytic efficacy of recombinant vesicular stomatitis virus and myxoma virus in experimental models of rhabdoid tumors", Clin. Cancer Res., 14 (4):1218-1227 (2008).

Yamaguchi, et al., "Human chorionic gonadotropin in colorectal cancer and its relationship to prognosis", Br. J. Cancer, 60(3):382-384 (1989).

Yoshida, et al., "Antitumor effect of an adeno-associated virus vector containing the human interferon-beta gene on experimental intracranial human glioma", Jpn. J. Cancer Res., 93:223-228 (2002).

Zeicher, et al., "Oncoselective parvoviral vector-mediated gene therapy of cancer", Oncol. Res., 13:437-444 (2003).

Zrachia, et al., "Infection of glioma cells with Sindbis virus induces selective activation and tyrosine phophorylation of protein kinase C delta. Implications for Sindbis virus-induced apoptosis", J. Biol. Chem., 277:23693-23701 (2002).

* cited by examiner

VSV
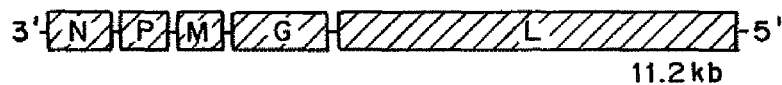
G/GFP
RP30
M51/CT9
1'GFP
FI

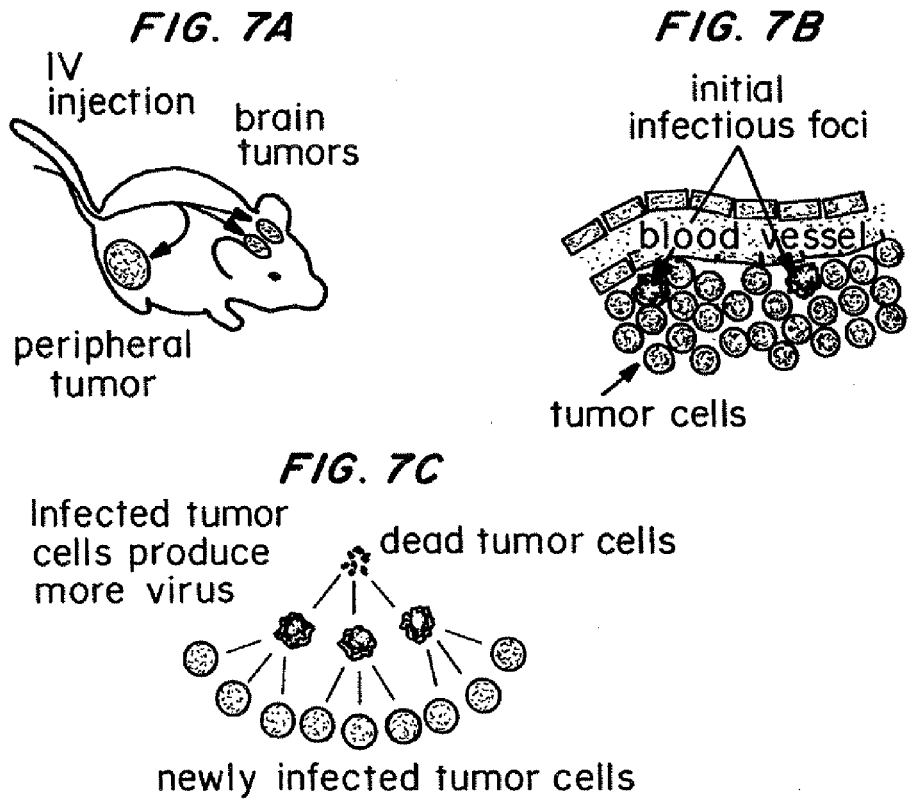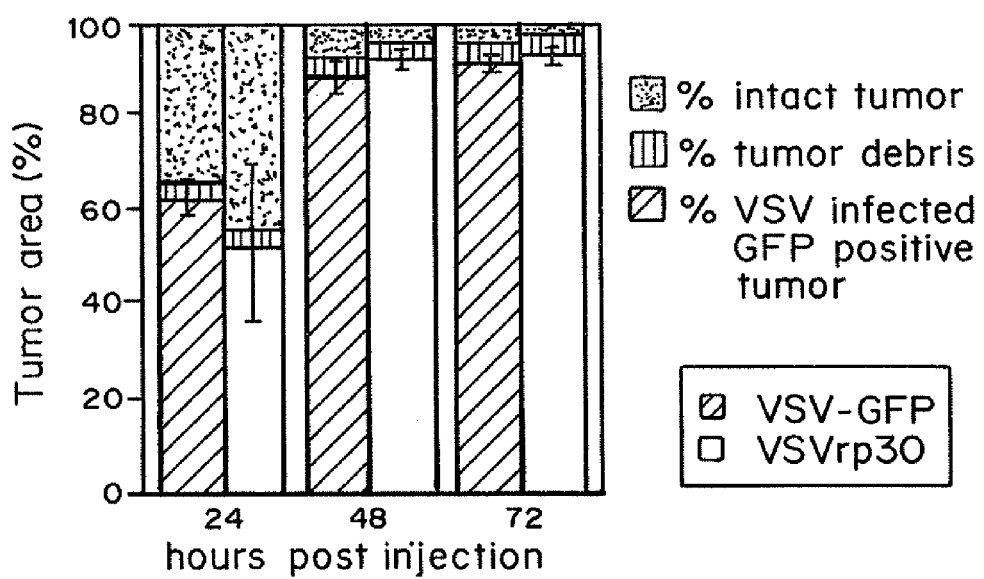

SEQUENCE LISTING

```
<160> NUMBER OF SEQ ID NOS: 41

<210> SEQ ID NO 1
<211> LENGTH: 13455
<212> TYPE: DNA
<213> ORGANISM: Artificial sequence
<220> FEATURE:
<223> OTHER INFORMATION: Synthetic cDNA sense strand encoding VSV-G/GFP

<400> SEQUENCE: 1
acgaagacaa acaaaccatt attatcatta aaaggctcag gagaaacttt aacagtaatc      60
aaaatgtctg ttacagtcaa gagaatcatt gacaacacag tcgtagttcc aaaacttcct     120
gcaaatgagg atccagtgga atacccggca gattacttca gaaaatcaaa ggagattcct     180
ctttacatca atactacaaa aagtttgtca gatctaagag gatatgtcta ccaaggcctc     240
aaatccggaa atgtatcaat catacatgtc aacagctact tgtatggagc attaaaggac     300
atccggggta agttggataa agattggtca agtttcggaa taaacatcgg gaaagcaggg     360
gatacaatcg gaatatttga ccttgtatcc ttgaaagccc tggacggcgt acttccagat     420
```

```
ggagtatcgg atgcttccag aaccagcgca gatgacaaat ggttgccttt gtatctactt    480
ggcttataca gagtgggcag aacacaaatg cctgaataca gaaaaaagct catggatggg    540
ctgacaaatc aatgcaaaat gatcaatgaa cagtttgaac ctcttgtgcc agaaggtcgt    600
gacatttttg atgtgtgggg aaatgacagt aattacacaa aaattgtcgc tgcagtggac    660
atgttcttcc acatgttcaa aaacatgaa tgtgcctcgt tcagatacgg aactattgtt     720
tccagattca agattgtgc tgcattggca acatttggac acctctgcaa aataaccgga     780
atgtctacag aagatgtaac gacctggatc ttgaaccgag aagttgcaga tgaaatggtc    840
caaatgatgc ttccaggcca agaaattgac aaggccgatt catacatgcc ttatttgatc    900
gactttggat tgtcttctaa gtctccatat tcttccgtca aaaaccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgccg acttggcaca acagttttgt gttggagata caaatacac tccagatgat    1140
agtaccggag gattgacgac taatgcaccg ccacaaggca gagatgtggt cgaatggctc   1200
ggatggtttg aagatcaaaa cagaaaaccg actcctgata tgatgcagta tgcgaaaaga   1260
gcagtcatgt cactgcaagg cctaagagag aagacaattg caagtatgc taagtcagaa    1320
tttgacaaat gaccctataa ttctcagatc acctattata tattatgcta catatgaaaa   1380
aaactaacag atatcatgga taatctcaca aaagttcgtg agtatctcaa gtcctattct   1440
cgtctggatc aggcggtagg agagatagat gagatcgaag cacaacgagc tgaaaagtcc   1500
aattatgagt tgttccaaga ggatggagtg aagagcata ctaagccctc ttatttcag     1560
gcagcagatg attctgacac agaatctgaa ccagaaattg aagacaatca aggcttgtat   1620
gcaccagatc cagaagctga gcaagttgaa ggctttatac aggggccttt agatgactat   1680
gcagatgagg aagtggatgt tgtatttact tcggactgga acagcctga gcttgaatct    1740
gacgagcatg gaaagacctt acggttgaca tcgccagagg gtttaagtgg agagcagaaa   1800
tcccagtggc tttcgacgat taaagcagtc gtgcaaagtg ccaaatactg gaatctggca   1860
gagtgcacat ttgaagcatc gggagaaggg gtcattatga aggagcgcca gataactccg   1920
gatgtatata aggtcactcc agtgatgaac acacatccgt cccaatcaga agcagtatca   1980
gatgtttggt ctctctcaaa gacatccatg actttccaac ccaagaaagc aagtcttcag   2040
cctctcacca tatccttgga tgaattgttc tcatctagag agagttcat ctctgtcgga    2100
ggtgacggac gaatgtctca taaagaggcc atcctgctcg gcctgagata caaaaagttg   2160
tacaatcagg cgagagtcaa atattctctg tagactatga aaaaagtaa cagatatcac   2220
gatctaagtg ttatcccaat ccattcatca tgagttcctt aaagaagatt ctcggtctga   2280
agggaaagg taagaaatct aagaaattag ggatcgcacc acccccttat gaagaggaca    2340
ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga acgtcccctt ctacaaaatc ttggcttttt   2580
tgggttcttc taatctaaag gccactccag cggtattggc agatcaaggt caaccagagt   2640
atcacgctca ctgcgaaggc agggcttatt tgccacatag gatggggaag acccctccca   2700
tgctcaatgt accagagcac ttcagaagac cattcaatat aggtctttac aagggaacga   2760
ttgagctcac aatgaccatc tacgatgatg agtcactgga agcagctcct atgatctggg   2820
```

```
atcatttcaa ttcttccaaa ttttctgatt tcagagagaa ggccttaatg tttggcctga   2880
ttgtcgagaa aaaggcatct ggagcgtggg tcctggactc tatcggccac ttcaaatgag   2940
ctagtctaac ttctagcttc tgaacaatcc ccggtttact cagtctcccc taattccagc   3000
ctctcgaaca actaatatcc tgtcttttct atccctatga aaaaaactaa cagagatcga   3060
tctgtttacg cgtcactatg aagtgccttt tgtacttagc cttttttattc attggggtga   3120 attgcaagtt caccatagtt tttccacaca accaaaaagg aaactggaaa aatgttcctt   3180
ctaattacca ttattgcccg tcaagctcag atttaaattg gcataatgac ttaataggca   3240
cagccttaca agtcaaaatg cccaagagtc acaaggctat tcaagcagac ggttggatgt   3300
gtcatgcttc caaatgggtc actacttgtg atttccgctg gtatggaccg aagtatataa   3360
cacattccat ccgatccttc actccatctg tagaacaatg caaggaaagc attgaacaaa   3420
cgaaacaagg aacttggctg aatccaggct tccctcctca agttgtgga tatgcaactg    3480 tgacggatgc cgaagcagtg attgtccagg tgactcctca ccatgtgctg gttgatgaat   3540
acacaggaga atgggttgat tcacagttca tcaacgaaaa atgcagcaat tacatatgcc   3600
ccactgtcca taactctaca acctggcatt ctgactataa ggtcaaaggg ctatgtgatt   3660
ctaacctcat ttccatggac atcaccttct tctcagagga cggagagcta tcatccctgg   3720 gaaggaggg cacagggttc agaagtaact actttgctta tgaaactgga ggcaaggcct    3780
gcaaaatgca atactgcaag cattggggag tcagactccc atcaggtgtc tggttcgaga   3840
tggctgataa ggatctcttt gctgcagcca gattccctga atgcccagaa gggtcaagta   3900
tctctgctcc atctcagacc tcagtggatg taagtctaat tcaggacgtt gagaggatct   3960
tggattattc cctctgccaa gaaacctgga gcaaaatcag agcgggtctt ccaatctctc   4020
cagtggatct cagctatctt gctcctaaaa acccaggaac cggtcctgct ttcaccataa   4080
tcaatggtac cctaaaatac tttgagacca gatacatcag agtcgatatt gctgctccaa   4140
tcctctcaag aatggtcgga atgatcagtg aactaccac agaaagggaa ctgtgggatg    4200
actgggcacc atatgaagac gtggaaattg gacccaatgg agttctgagg accagttcag   4260
gatataagtt tccttatac atgattggac atggtatgtt ggactccgat cttcatctta    4320
gctcaaaggc tcaggtgttc gaacatcctc acattcaaga cgctgcttcg caacttcctg   4380
atgatgagag tttatttttt ggtgatactg ggctatccaa aaatccaatc gagcttgtag   4440
aaggttggtt cagtagttgg aaaagctcta ttgcctctttt ttctttatc ataggggttaa    4500 tcattggact attcttggtt ctccgagttg gtatccatct ttgcattaaa ttaaagcaca   4560
ccaagaaaag acagatttat acagacatag agatgaaccg acttggaaag taactcaaat   4620
cctgctaggt atgaaaaaaa ctaacagata tcacgctcga gactatgaag tgccttttgt   4680
acttagcctt tttattcatt ggggtgaatt gcaagttcac catagttttt ccacacaacc   4740 aaaaggaaa ctggaaaaat gttccttcta attaccatta ttgcccgtca agctcagatt    4800
taaattggca taatgactta ataggcacag ccttacaagt caaatgccc aagagtcaca    4860 aggctattca agcagacggt tggatgtgtc atgcttccaa atgggtcact acttgtgatt   4920
tccgctggta tggaccgaag tatataacac attccatccg atccttcact ccatctgtag   4980
aacaatgcaa ggaaagcatt gaacaaacga acaaggaac ttggctgaat ccaggcttcc    5040
ctcctcaaag ttgtggatat gcaactgtga cggatgccga agcagtgatt gtccaggtga   5100
ctcctcacca tgtgctggtt gatgaataca caggagaatg ggttgattca cagttcatca   5160
acggaaaatg cagcaattac atatgcccca ctgtccataa ctctacaacc tggcattctg   5220
```

```
actataaggt caaagggcta tgtgattcta acctcatttc catggacatc accttcttct    5280
cagaggacgg agagctatca tccctgggaa aggagggcac agggttcaga agtaactact    5340
ttgcttatga aactggaggc aaggcctgca aaatgcaata ctgcaagcat tgggagtca     5400
gactcccatc aggtgtctgg ttcgagatgg ctgataagga tctctttgct gcagccagat    5460
tccctgaatg cccagaaggg tcaagtatct ctgctccatc tcagacctca gtggatgtaa    5520
gtctaattca ggacgttgag aggatcttgg attattccct ctgccaagaa acctggagca    5580
aaatcagagc gggtcttcca atctctccag tggatctcag ctatcttgct cctaaaaacc    5640
caggaaccgg tcctgctttc accataatca atggtaccct aaaatacttt gagaccagat    5700
acatcagagt cgatattgct gctccaatcc tctcaagaat ggtcggaatg atcagtggaa    5760
ctaccacaga aagggaactg tgggatgact gggcaccata tgaagacgtg gaaattggac    5820
ccaatggagt tctgaggacc agttcaggat ataagtttcc tttatacatg attggacatg    5880
gtatgttgga ctccgatctt catcttagct caaaggctca ggtgttcgaa catcctcaca    5940
ttcaagacgc tgcttcgcaa cttcctgatg atgagagttt atttttttggt gatactgggc    6000
tatccaaaaa tccaatcgag cttgtagaag gttggttcag tagttggaaa agctctattg    6060
cctcttttt ctttatcata gggttaatca ttggactatt cttggttctc cgagttggta    6120
tccatctttg cattaaatta aagcacacca agaaaagaca gatttataca gacatagaga    6180
tgaaccgact tggaaagatg gtgagcaagg gcgaggagct gttcaccggg gtggtgccca    6240
tcctggtcga gctggacggc gacgtaaacg gccacaagtt cagcgtgtcc ggcgagggcg    6300
agggcgatgc cacctacggc aagctgaccc tgaagttcat ctgcaccacc ggcaagctgc    6360
ccgtgccctg gcccaccctc gtgaccaccc tgacctacgg cgtgcagtgc ttcagccgct    6420
accccgacca catgaagcag cacgacttct tcaagtccgc catgcccgaa ggctacgtcc    6480
aggagcgcac catcttcttc aaggacgacg gcaactacaa gacccgcgcc gaggtgaagt    6540
tcgagggcga caccctggtg aaccgcatcg agctgaaggg catcgacttc aaggaggacg    6600
gcaacatcct ggggcacaag ctggagtaca actacaacag ccacaacgtc tatatcatgg    6660
ccgacaagca gaagaacggc atcaaggtga acttcaagat ccgccacaac atcgaggacg    6720
gcagcgtgca gctcgccgac cactaccagc agaacacccc catcggcgac ggccccgtgc    6780
tgctgcccga caaccactac ctgagcaccc agtccgccct gagcaaagac cccaacgaga    6840
agcgcgatca catggtcctg ctggagttcg tgaccgccgc cgggatcact ctcggcatgg    6900
acgagctgta caagtaagct agccagattc ttcatgtttg gaccaaatca acttgtgata    6960
ccatgctcaa agaggcctca attatatttg agttttaat tttatgaaa aaaactaaca    7020
gcaatcatgg aagtccacga ttttgagacc gacgagttca tgatttcaa tgaagatgac    7080
tatgccacaa gagaattcct gaatcccgat gagcgcatga cgtacttgaa tcatgctgat    7140
tacaacctga attctcctct aattagtgat gatattgaca atttaatcag gaaattcaat    7200
tctcttccaa ttccctcgat gtgggatagt aagaactggg atggagttct tgagatgtta    7260
acgtcatgtc aagccaatcc catcccaaca tctcagatgc ataaatggat gggaagttgg    7320
ttaatgtctg ataatcatga tgccagtcaa gggtatagtt tttacatga agtggacaaa    7380
gaggcagaaa taacatttga cgtggtggag accttcatcc gcggctgggg caacaaacca    7440
attgaataca tcaaaaagga aagatggact gactcattca aaattctcgc ttatttgtgt    7500
caaaagttt tggacttaca caagttgaca ttaatcttaa atgctgtctc tgaggtggaa    7560
ttgctcaact tggcgaggac tttcaaaggc aaagtcagaa gaagttctca tggaacgaac    7620
```

```
atatgcagga ttagggttcc cagcttgggt cctacttttta tttcagaagg atgggcttac    7680
ttcaagaaac ttgatattct aatggaccga aactttctgt taatggtcaa agatgtgatt    7740
atagggagga tgcaaacggt gctatccatg gtatgtagaa tagacaacct gttctcagag    7800
caagacatct tctcccttct aaatatctac agaattggag ataaaattgt ggagaggcag    7860 ggaaatttt  cttatgactt gattaaaatg gtggaaccga tatgcaactt gaagctgatg    7920
aaattagcaa gagaatcaag gcctttagtc ccacaattcc ctcattttga aaatcatatc    7980
aagacttctg ttgatgaagg ggcaaaaatt gaccgaggta taagattcct ccatgatcag    8040
ataatgagtg tgaaaacagt ggatctcaca ctggtgattt atggatcgtt cagacattgg    8100
ggtcatcctt ttatagatta ttacactgga ctagaaaaat tacattccca agtaaccatg    8160
aagaaagata ttgatgtgtc atatgcaaaa gcacttgcaa gtgatttagc tcggattgtt    8220
ctatttcaac agttcaatga tcataaaaag tggttcgtga atggagactt gctccctcat    8280
gatcatccct ttaaaagtca tgttaaagaa aatacatggc ccacagctgc tcaagttcaa    8340
gattttggag ataaatggca tgaacttccg ctgattaaat gttttgaaat acccgactta    8400
ctagacccat cgataatata ctctgacaaa agtcattcaa tgaataggtc agaggtgttg    8460
aaacatgtcc gaatgaatcc gaacactcct atccctagta aaaggtgtt  gcagactatg    8520 ttggacacaa aggctaccaa ttggaaagaa tttcttaaag agattgatga aagggctta    8580 gatgatgatg atctaattat tggtcttaaa ggaaaggaga gggaactgaa gttggcaggt    8640 agattttct  ccctaatgtc ttggaaattg cgagaatact ttgtaattac cgaatatttg    8700
ataaagactc atttcgtccc tatgtttaaa ggcctgacaa tggcggacga tctaactgca    8760
gtcattaaaa agatgttaga ttcctcatcc ggccaaggat tgaagtcata tgaggcaatt    8820
tgcatagcca atcacattga ttacgaaaaa tggaataacc accaaaggaa gttatcaaac    8880
ggcccagtgt tccgagttat gggccagttc ttaggttatc catccttaat cgagagaact    8940
catgaatttt ttgagaaaag tcttatatac tacaatggaa gaccagactt gatgcgtgtt    9000
cacaacaaca cactgatcaa ttcaacctcc caacgagttt gttggcaagg acaagagggt    9060
ggactggaag gtctacggca aaaaggatgg agtatcctca atctactggt tattcaaaga    9120
gaggctaaaa tcagaaacac tgctgtcaaa gtcttggcac aaggtgataa tcaagttatt    9180
tgcacacagt ataaaacgaa gaaatcgaga aacgttgtag aattacaggg tgctctcaat    9240
caaatggttt ctaataatga gaaaattatg actgcaatca aaataggac  agggaagtta    9300 ggacttttga taaatgacga tgagactatg caatctgcag attacttgaa ttatggaaaa    9360
ataccgattt tccgtggagt gattagaggg ttagagacca agagatggtc acgagtgact    9420
tgtgtcacca atgaccaaat acccacttgt gctaatataa tgagctcagt ttccacaaat    9480
gctctcaccg tagctcattt tgctgagaac ccaatcaatg ccatgataca gtacaattat    9540
tttgggacat ttgctagact cttgttgatg atgcatgatc ctgctcttcg tcaatcattg    9600
tatgaagttc aagataagat accgggcttg cacagttcta ctttcaaata cgccatgttg    9660
tatttggacc cttccattgg aggagtgtcg ggcatgtctt tgtccaggtt tttgattaga    9720
gccttcccag atcccgtaac agaaagtctc tcattctgga gattcatcca tgtacatgct    9780
cgaagtgagc atctgaagga gatgagtgca gtatttggaa accccgagat agccaagttt    9840
cgaataactc acatagacaa gctagtagaa gatccaacct ctctgaacat cgctatggga    9900
atgagtccga cgaacttgtt aaagactgag gttaaaaaat gcttaatcga atcaagacaa    9960
accatcagga accaggtgat taaggatgca accatatatt tgtatcatga agaggatcgg   10020
```

```
ctcagaagtt tcttatggtc aataaatcct ctgttcccta gattttaag tgaattcaaa      10080 tcaggcactt ttttgggagt cgcagacggg ctcatcagtc tatttcaaaa ttctcgtact      10140
attcggaact cctttaagaa aaagtatcat agggaattgg atgatttgat tgtgaggagt      10200
gaggtatcct ctttgacaca tttagggaaa cttcatttga aagggggatc atgtaaaatg      10260
tggacatgtt cagctactca tgctgacaca ttaagataca aatcctgggg ccgtacagtt      10320
attgggacaa ctgtaccca tccattagaa atgttgggtc cacaacatcg aaaagagact      10380
ccttgtgcac catgtaacac atcagggttc aattatgttt ctgtgcattg tccagacggg      10440
atccatgacg tctttagttc acggggacca ttgcctgctt atctagggtc taaaacatct      10500
gaatctacat ctattttgca gccttgggaa agggaaagca aagtcccact gattaaaaga      10560
gctacacgtc ttagagatgc tatctcttgg tttgttgaac ccgactctaa actagcaatg      10620
actatacttt ctaacatcca ctctttaaca ggcgaagaat ggaccaaaag gcagcatggg      10680
ttcaaaagaa cagggtctgc ccttcatagg ttttcgacat ctcggatgag ccatggtggg      10740
ttcgcatctc agagcactgc agcattgacc aggttgatgg caactacaga caccatgagg      10800
gatctgggag atcagaattt cgacttttta ttccaagcaa cgttgctcta tgctcaaatt      10860
accaccactg ttgcaagaga cggatggatc accagttgta cagatcatta tcatattgcc      10920
tgtaagtcct gtttgagacc catagaagag atcaccctgg actcaagtat ggactacacg      10980 ccccccagatg tatcccatgt gctgaagaca tggaggaatg gggaaggttc gtgggacaa      11040 gagataaaac agatctatcc tttagaaggg aattggaaga atttagcacc tgctgagcaa      11100
tcctatcaag tcggcagatg tataggtttt ctatatggag acttggcgta tagaaaatct      11160
actcatgccg aggacagttc tctatttcct ctatctatac aaggtcgtat tagaggtcga      11220
ggtttcttaa aagggttgct agacggatta atgagagcaa gttgctgcca agtaatacac      11280
cggagaagtc tggctcattt gaagaggccg gccaacgcag tgtacggagg tttgatttac      11340
ttgattgata aattgagtgt atcacctcca ttcctttctc ttactagatc aggacctatt      11400
agagacgaat tagaaacgat tccccacaag atcccaacct cctatccgac aagcaaccgt      11460
gatatggggg tgattgtcag aaattacttc aaataccaat gccgtctaat tgaaaaggga      11520
aaatacagat cacattattc acaattatgg ttattctcag atgtcttatc catagacttc      11580
attggaccat tctctatttc caccacctc ttgcaaatcc tatacaagcc attttatct      11640 gggaaagata agaatgagtt gagagagctg gcaaatcttt cttcattgct aagatcagga      11700
gaggggtggg aagacataca tgtgaaattc ttcaccaagg acatattatt gtgtccagag      11760
gaaatcagac atgcttgcaa gttcgggatt gctaaggata taataaaga catgagctat      11820 cccccttggg gaagggaatc cagagggaca attacaacaa tccctgttta ttatacgacc      11880 acccccttacc caaagatgct agagatgcct ccaagaatcc aaaatcccct gctgtccgga      11940
atcaggttgg gccaattacc aactggcgct cattataaaa ttcggagtat attacatgga      12000
atgggaatcc attacaggga cttcttgagt tgtggagacg gctccggagg gatgactgct      12060
gcattactac gagaaaatgt gcatagcaga ggaatattca atagtctgtt agaattatca      12120
gggtcagtca tgcgaggcgc ctctcctgag ccccccagtg ccctagaaac tttaggagga      12180
gataaatcga gatgtgtaaa tggtgaaaca tgttgggaat atccatctga cttatgtgac      12240
ccaaggactt gggactattt cctccgactc aaagcaggct tggggcttca aattgattta      12300
attgtaatgg atatggaagt tcggattct tctactagcc tgaaaattga gacgaatgtt      12360
agaaattatg tgcaccggat tttggatgag caaggagttt taatctacaa gacttatgga      12420
```

```
acatatattt gtgagagcga aaagaatgca gtaacaatcc ttggtcccat gttcaagacg    12480
gtcgacttag ttcaaacaga atttagtagt tctcaaacgt ctgaagtata tatggtatgt    12540
aaaggtttga agaaattaat cgatgaaccc aatcccgatt ggtcttccat caatgaatcc    12600
tggaaaaacc tgtacgcatt ccagtcatca gaacaggaat ttgccagagc aaagaaggtt    12660
agtacatact ttaccttgac aggtattccc tcccaattca ttcctgatcc ttttgtaaac    12720
attgagacta tgctacaaat attcggagta cccacgggtg tgtctcatgc ggctgcctta    12780
aaatcatctg atagacctgc agatttattg accattagcc tttttttatat ggcgattata    12840 tcgtattata acatcaatca tatcagagta ggaccgatac ctccgaaccc cccatcagat    12900
ggaattgcac aaaatgtggg gatcgctata actggtataa gcttttggct gagtttgatg    12960
gagaaagaca ttccactata tcaacagtgt ttagcagtta tccagcaatc attcccgatt    13020
aggtgggagg ctgtttcagt aaaaggagga tacaagcaga agtggagtac tagaggtgat    13080
gggctcccaa aagatacccg aatttcagac tccttggccc caatcgggaa ctggatcaga    13140
tctctggaat tggtccgaaa ccaagttcgt ctaaatccat tcaatgagat cttgttcaat    13200
cagctatgtc gtacagtgga taatcatttg aaatggtcaa atttgcgaag aaacacagga    13260
atgattgaat ggatcaatag acgaatttca aaagaagacc ggtctatact gatgttgaag    13320
agtgacctac acgaggaaaa ctcttggaga gattaaaaaa tcatgaggag actccaaact    13380
ttaagtatga aaaaacttt gatccttaag accctcttgt ggttttttatt ttttatctgg    13440 ttttgtggtc ttcgt                                                     13455

<210> SEQ ID NO 2
<211> LENGTH: 798
<212> TYPE: DNA
<213> ORGANISM: Artificial Sequence
<220> FEATURE:
<223> OTHER INFORMATION: Synthetic nucleotide 1396-2193 of SEQ ID NO: 1

<400> SEQUENCE: 2
atggataatc tcacaaaagt tcgtgagtat ctcaagtcct attctcgtct ggatcaggcg      60
gtaggagaga tagatgagat cgaagcacaa cgagctgaaa agtccaatta tgagttgttc     120
caagaggatg gagtggaaga gcatactaag ccctcttatt ttcaggcagc agatgattct     180
gacacagaat ctgaaccaga aattgaagac aatcaaggct tgtatgcacc agatccagaa     240
gctgagcaag ttgaaggctt tatacagggg cctttagatg actatgcaga tgaggaagtg     300
gatgttgtat ttacttcgga ctggaaacag cctgagcttg aatctgacga gcatggaaag     360
accttacggt tgcatcgcc agagggttta agtggagagc agaaatccca gtggctttcg      420
acgattaaag cagtcgtgca aagtgccaaa tactggaatc tggcagagtg cacatttgaa     480
gcatcgggag aagggcat tatgaaggag cgccagataa ctccggatgt atataaggtc       540
actccagtga tgaacacaca tccgtcccaa tcagaagcag tatcagatgt ttggtctctc     600
tcaaagacat ccatgacttt ccaacccaag aaagcaagtc ttcagcctct caccatatcc     660
ttggatgaat tgttctcatc tagaggagag ttcatctctg tcggaggtga cggacgaatg     720
tctcataaag aggccatcct gctcggcctg agatacaaaa agttgtacaa tcaggcgaga     780
gtcaaatatt ctctgtag                                                   798

<210> SEQ ID NO 3
<211> LENGTH: 265
<212> TYPE: PRT
<213> ORGANISM: Vesicular stomatitis virus
```

<400> SEQUENCE: 3

```
Met Asp Asn Leu Thr Lys Val Arg Glu Tyr Leu Lys Ser Tyr Ser Arg
1               5                   10                  15
Leu Asp Gln Ala Val Gly Glu Ile Asp Glu Ile Glu Ala Gln Arg Ala
            20                  25                  30
Glu Lys Ser Asn Tyr Glu Leu Phe Gln Glu Asp Gly Val Glu Glu His
        35                  40                  45
Thr Lys Pro Ser Tyr Phe Gln Ala Ala Asp Asp Ser Asp Thr Glu Ser
    50                  55                  60
Glu Pro Glu Ile Glu Asp Asn Gln Gly Leu Tyr Ala Pro Asp Pro Glu
65                  70                  75                  80
Ala Glu Gln Val Glu Gly Phe Ile Gln Gly Pro Leu Asp Asp Tyr Ala
                85                  90                  95
Asp Glu Glu Val Asp Val Val Phe Thr Ser Asp Trp Lys Gln Pro Glu
            100                 105                 110
Leu Glu Ser Asp Glu His Gly Lys Thr Leu Arg Leu Thr Ser Pro Glu
        115                 120                 125
Gly Leu Ser Gly Glu Gln Lys Ser Gln Trp Leu Ser Thr Ile Lys Ala
    130                 135                 140
Val Val Gln Ser Ala Lys Tyr Trp Asn Leu Ala Glu Cys Thr Phe Glu
145                 150                 155                 160
Ala Ser Gly Glu Gly Val Ile Met Lys Glu Arg Gln Ile Thr Pro Asp
                165                 170                 175
Val Tyr Lys Val Thr Pro Val Met Asn Thr His Pro Ser Gln Ser Glu
            180                 185                 190
Ala Val Ser Asp Val Trp Ser Leu Ser Lys Thr Ser Met Thr Phe Gln
        195                 200                 205
Pro Lys Lys Ala Ser Leu Gln Pro Leu Thr Ile Ser Leu Asp Glu Leu
    210                 215                 220
Phe Ser Ser Arg Gly Glu Phe Ile Ser Val Gly Gly Asp Gly Arg Met
225                 230                 235                 240
Ser His Lys Glu Ala Ile Leu Leu Gly Leu Arg Tyr Lys Lys Leu Tyr
                245                 250                 255
Asn Gln Ala Arg Val Lys Tyr Ser Leu
            260                 265
```

<210> SEQ ID NO 4
<211> LENGTH: 6330
<212> TYPE: DNA
<213> ORGANISM: Artificial Sequence
<220> FEATURE:
<223> OTHER INFORMATION: Synthetic fragment for SEQ ID NO: 1 sequence between 7027-13356

<400> SEQUENCE: 4

```
atggaagtcc acgattttga gaccgacgag ttcaatgatt tcaatgaaga tgactatgcc      60
acaagagaat tcctgaatcc cgatgagcgc atgacgtact tgaatcatgc tgattacaac     120
ctgaattctc ctctaattag tgatgatatt gacaatttaa tcaggaaatt caattctctt     180
ccaattccct cgatgtggga tagtaagaac tgggatggag ttcttgagat gttaacgtca     240
tgtcaagcca atcccatccc aacatctcag atgcataaat ggatgggaag ttggttaatg     300
tctgataatc atgatgccag tcaagggtat agtttttac atgaagtgga caaagaggca     360
gaaataacat ttgacgtggt ggagaccttc atccgcggct ggggcaacaa accaattgaa     420
tacatcaaaa aggaaagatg gactgactca ttcaaaattc tcgcttattt gtgtcaaaag     480
```

```
tttttggact tacacaagtt gacattaatc ttaaatgctg tctctgaggt ggaattgctc    540
aacttggcga ggactttcaa aggcaaagtc agaagaagtt ctcatggaac gaacatatgc    600
aggattaggg ttcccagctt gggtcctact tttatttcag aaggatgggc ttacttcaag    660
aaacttgata ttctaatgga ccgaaacttt ctgttaatgg tcaaagatgt gattataggg    720
aggatgcaaa cggtgctatc catggtatgt agaatagaca acctgttctc agagcaagac    780
atcttctccc ttctaaatat ctacagaatt ggagataaaa ttgtggagag cagggaaat    840 ttttcttatg acttgattaa aatggtggaa ccgatatgca acttgaagct gatgaaatta    900
gcaagagaat caaggccttt agtcccacaa ttccctcatt ttgaaaatca tatcaagact    960
tctgttgatg aaggggcaaa aattgaccga ggtataagat tcctccatga tcagataatg    1020
agtgtgaaaa cagtggatct cacactggtg atttatggat cgttcagaca ttgggtcat    1080 cctttttatag attattacac tggactagaa aaattacatt cccaagtaac catgaagaaa    1140
gatattgatg tgtcatatgc aaaagcactt gcaagtgatt tagctcggat tgttctattt    1200
caacagttca atgatcataa aaagtggttc gtgaatggag acttgctccc tcatgatcat    1260
ccctttaaaa gtcatgttaa agaaaataca tggcccacag ctgctcaagt tcaagatttt    1320
ggagataaat ggcatgaact tccgctgatt aaatgttttg aaatacccga cttactagac    1380
ccatcgataa tatactctga caaaagtcat tcaatgaata ggtcagaggt gttgaaacat    1440
gtccgaatga atccgaacac tcctatccct agtaaaaagg tgttgcagac tatgttggac    1500
acaaaggcta ccaattggaa agaatttctt aaagagattg atgagaaggg cttagatgat    1560
gatgatctaa ttattggtct taaaggaaag gagagggaac tgaagttggc aggtagattt    1620
ttctccctaa tgtcttggaa attgcgagaa tactttgtaa ttaccgaata tttgataaag    1680
actcatttcg tccctatgtt taaaggcctg acaatggcgg acgatctaac tgcagtcatt    1740
aaaaagatgt tagattcctc atccggccaa ggattgaagt catatgaggc aatttgcata    1800
gccaatcaca ttgattacga aaaatggaat aaccaccaaa ggaagttatc aaacggccca    1860
gtgttccgag ttatgggcca gttcttaggt tatccatcct taatcgagag aactcatgaa    1920 tttttttgaga aaagtcttat atactacaat ggaagaccag acttgatgcg tgttcacaac    1980
aacacactga tcaattcaac ctcccaacga gtttgttggc aaggacaaga gggtggactg    2040
gaaggtctac ggcaaaaagg atggagtatc ctcaatctac tggttattca aagagaggct    2100
aaaatcagaa acactgctgt caaagtcttg gcacaaggtg ataatcaagt tatttgcaca    2160
cagtataaaa cgaagaaatc gagaaacgtt gtagaattac agggtgctct caatcaaatg    2220
gtttctaata atgagaaaat tatgactgca atcaaaatag gacagggaa gttaggactt    2280 ttgataaatg acgatgagac tatgcaatct gcagattact tgaattatgg aaaaataccg    2340
attttccgtg gagtgattag agggttagag accaagagat ggtcacgagt gacttgtgtc    2400
accaatgacc aaatacccac ttgtgctaat ataatgagct cagtttccac aaatgctctc    2460
accgtagctc attttgctga gaacccaatc aatgccatga tacagtacaa ttattttggg    2520
acatttgcta gactcttgtt gatgatgcat gatcctgctc ttcgtcaatc attgtatgaa    2580
gttcaagata agataccggg cttgcacagt tctactttca aatacgccat gttgtatttg    2640
gacccttcca ttggaggagt gtcggcatg tctttgtcca ggttttgat tagagccttc    2700 ccagatcccg taacagaaag tctctcattc tggagattca tccatgtaca tgctcgaagt    2760
gagcatctga aggagatgag tgcagtattt ggaaaccccg atatagcaa gtttcgaata    2820 actcacatag acaagctagt agaagatcca acctctctga acatcgctat gggaatgagt    2880
```

```
ccagcgaact tgttaaagac tgaggttaaa aaatgcttaa tcgaatcaag acaaaccatc    2940
aggaaccagg tgattaagga tgcaaccata tatttgtatc atgaagagga tcggctcaga    3000
agtttcttat ggtcaataaa tcctctgttc cctagatttt taagtgaatt caaatcaggc    3060 actttttgg gagtcgcaga cgggctcatc agtctatttc aaaattctcg tactattcgg     3120
aactccttta agaaaagta tcatagggaa ttggatgatt tgattgtgag gagtgaggta     3180
tcctctttga cacatttagg gaaacttcat ttgagaaggg gatcatgtaa aatgtggaca    3240
tgttcagcta ctcatgctga cacattaaga tacaaatcct ggggccgtac agttattggg    3300
acaactgtac cccatccatt agaaatgttg ggtccacaac atcgaaaaga gactccttgt    3360
gcaccatgta acacatcagg gttcaattat gtttctgtgc attgtccaga cgggatccat    3420 gacgtctttta gttcacgggg accattgcct gcttatctag ggtctaaaac atctgaatct    3480
acatctattt tgcagccttg ggaaagggaa agcaaagtcc cactgattaa aagagctaca    3540
cgtcttagag atgctatctc ttggtttgtt gaacccgact ctaaactagc aatgactata    3600
ctttctaaca tccactcttt aacaggcgaa gaatggacca aaaggcagca tgggttcaaa    3660
agaacagggt ctgcccttca taggttttcg acatctcgga tgagccatgg tgggttcgca    3720
tctcagagca ctgcagcatt gaccaggttg atggcaacta cagacaccat gagggatctg    3780
ggagatcaga atttcgactt tttattccaa gcaacgttgc tctatgctca aattaccacc    3840
actgttgcaa gagacggatg gatcaccagt tgtacagatc attatcatat tgcctgtaag    3900
tcctgtttga gacccataga agagataccc ctggactcaa gtatggacta cacgccccca    3960
gatgtatccc atgtgctgaa gacatggagg aatggggaag gttcgtgggg acaagagata    4020
aaacagatct atcctttaga agggaattgg aagaatttag cacctgctga gcaatcctat    4080
caagtcggca gatgtatagg ttttctatat ggagacttgg cgtatagaaa atctactcat    4140
gccgaggaca gttctctatt tcctctatct atacaaggtc gtattagagg tcgaggtttc    4200
ttaaaagggt tgctagacgg attaatgaga gcaagttgct gccaagtaat acaccggaga    4260
agtctggctc atttgaagag gccggccaac gcagtgtacg gaggtttgat ttacttgatt    4320
gataaattga gtgtatcacc tccattcctt tctcttacta gatcaggacc tattagagac    4380
gaattagaaa cgattcccca caagatccca acctcctatc cgacaagcaa ccgtgatatg    4440
ggggtgattg tcagaaatta cttcaaatac caatgccgtc taattgaaaa gggaaaatac    4500
agatcacatt attcacaatt atggttattc tcagatgtct tatccataga cttcattgga    4560
ccattctcta tttccaccac cctcttgcaa atcctataca agccattttt atctgggaaa    4620
gataagaatg agttgagaga gctggcaaat cttttcttcat tgctaagatc aggagagggg    4680
tgggaagaca tacatgtgaa attcttcacc aaggacatat tattgtgtcc agaggaaatc    4740
agacatgctt gcaagttcgg gattgctaag gataataata aagacatgag ctatcccccct    4800 tggggaaggg aatccagagg gacaattaca acaatccctg tttattatac gaccacccct    4860
tacccaaaga tgctagagat gcctccaaga atccaaaatc ccctgctgtc cggaatcagg    4920
ttgggccaat taccaactgg cgctcattat aaaaattcgga gtatattaca tggaatggga    4980
atccattaca gggacttctt gagttgtgga gacggctccg gagggatgac tgctgcatta    5040
ctacgagaaa atgtgcatag cagaggaata ttcaatagtc tgttagaatt atcagggtca    5100
gtcatgcgag gcgcctctcc tgagccccccc agtgccctag aaactttagg aggagataaa    5160
tcgagatgtg taaatggtga acatgttggg gaatatccat ctgacttatg tgacccaagg    5220
acttgggact atttcctccg actcaaagca ggcttggggc ttcaaattga tttaattgta    5280
```

```
atggatatgg aagttcggga ttcttctact agcctgaaaa ttgagacgaa tgttagaaat    5340
tatgtgcacc ggattttgga tgagcaagga gtttttaatct acaagactta tggaacatat    5400
atttgtgaga gcgaaaagaa tgcagtaaca atccttggtc ccatgttcaa gacggtcgac    5460
ttagttcaaa cagaatttag tagttctcaa acgtctgaag tatatatggt atgtaaaggt    5520
ttgaagaaat taatcgatga acccaatccc gattggtctt ccatcaatga atcctggaaa    5580
aacctgtacg cattccagtc atcagaacag gaatttgcca gagcaaagaa ggttagtaca    5640
tactttacct tgacaggtat tccctcccaa ttcattcctg atcctttgt aaacattgag    5700 actatgctac aaatattcgg agtacccacg ggtgtgtctc atgcggctgc cttaaaatca    5760
tctgatagac ctgcagattt attgaccatt agccttttt atatggcgat tatatcgtat    5820
tataacatca atcatatcag agtaggaccg atacctccga accccccatc agatggaatt    5880
gcacaaaatg tggggatcgc tataactggt ataagctttt ggctgagttt gatggagaaa    5940
gacattccac tatatcaaca gtgtttagca gttatccagc aatcattccc gattaggtgg    6000
gaggctgttt cagtaaaagg aggatacaag cagaagtgga gtactagagg tgatgggctc    6060
ccaaaagata cccgaatttc agactccttg gccccaatcg ggaactggat cagatctctg    6120
gaattggtcc gaaaccaagt tcgtctaaat ccattcaatg agatcttgtt caatcagcta    6180
tgtcgtacag tggataatca tttgaaatgg tcaaatttgc gaagaaacac aggaatgatt    6240
gaatggatca atagacgaat ttcaaaagaa gaccggtcta tactgatgtt gaagagtgac    6300
ctacacgagg aaaactcttg gagagattaa                                      6330

<210> SEQ ID NO 5
<211> LENGTH: 2109
<212> TYPE: PRT
<213> ORGANISM: Vesicular stomatitis virus

<400> SEQUENCE: 5

Met Glu Val His Asp Phe Glu Thr Asp Glu Phe Asn Asp Phe Asn Glu
1               5                   10                  15

Asp Asp Tyr Ala Thr Arg Glu Phe Leu Asn Pro Asp Glu Arg Met Thr
            20                  25                  30

Tyr Leu Asn His Ala Asp Tyr Asn Leu Asn Ser Pro Leu Ile Ser Asp
        35                  40                  45

Asp Ile Asp Asn Leu Ile Arg Lys Phe Asn Ser Leu Pro Ile Pro Ser
    50                  55                  60

Met Trp Asp Ser Lys Asn Trp Asp Gly Val Leu Glu Met Leu Thr Ser
65                  70                  75                  80

Cys Gln Ala Asn Pro Ile Pro Thr Ser Gln Met His Lys Trp Met Gly
                85                  90                  95

Ser Trp Leu Met Ser Asp Asn His Asp Ala Ser Gln Gly Tyr Ser Phe
            100                 105                 110

Leu His Glu Val Asp Lys Glu Ala Glu Ile Thr Phe Asp Val Val Glu
        115                 120                 125

Thr Phe Ile Arg Gly Trp Gly Asn Lys Pro Ile Glu Tyr Ile Lys Lys
    130                 135                 140

Glu Arg Trp Thr Asp Ser Phe Lys Ile Leu Ala Tyr Leu Cys Gln Lys
145                 150                 155                 160

Phe Leu Asp Leu His Lys Leu Thr Leu Ile Leu Asn Ala Val Ser Glu
                165                 170                 175

Val Glu Leu Leu Asn Leu Ala Arg Thr Phe Lys Gly Lys Val Arg Arg
            180                 185                 190
```

```
Ser Ser His Gly Thr Asn Ile Cys Arg Ile Arg Val Pro Ser Leu Gly
        195                 200                 205

Pro Thr Phe Ile Ser Glu Gly Trp Ala Tyr Phe Lys Lys Leu Asp Ile
210                 215                 220

Leu Met Asp Arg Asn Phe Leu Met Val Lys Asp Val Ile Ile Gly
225                 230                 235                 240

Arg Met Gln Thr Val Leu Ser Met Val Cys Arg Ile Asp Asn Leu Phe
            245                 250                 255

Ser Glu Gln Asp Ile Phe Ser Leu Leu Asn Ile Tyr Arg Ile Gly Asp
            260                 265                 270

Lys Ile Val Glu Arg Gln Gly Asn Phe Ser Tyr Asp Leu Ile Lys Met
        275                 280                 285

Val Glu Pro Ile Cys Asn Leu Lys Leu Met Lys Leu Ala Arg Glu Ser
290                 295                 300

Arg Pro Leu Val Pro Gln Phe Pro His Phe Glu Asn His Ile Lys Thr
305                 310                 315                 320

Ser Val Asp Glu Gly Ala Lys Ile Asp Arg Gly Ile Arg Phe Leu His
            325                 330                 335

Asp Gln Ile Met Ser Val Lys Thr Val Asp Leu Thr Leu Val Ile Tyr
            340                 345                 350

Gly Ser Phe Arg His Trp Gly His Pro Phe Ile Asp Tyr Tyr Thr Gly
        355                 360                 365

Leu Glu Lys Leu His Ser Gln Val Thr Met Lys Lys Asp Ile Asp Val
370                 375                 380

Ser Tyr Ala Lys Ala Leu Ala Ser Asp Leu Ala Arg Ile Val Leu Phe
385                 390                 395                 400

Gln Gln Phe Asn Asp His Lys Lys Trp Phe Val Asn Gly Asp Leu Leu
            405                 410                 415

Pro His Asp His Pro Phe Lys Ser His Val Lys Glu Asn Thr Trp Pro
            420                 425                 430

Thr Ala Ala Gln Val Gln Asp Phe Gly Asp Lys Trp His Glu Leu Pro
        435                 440                 445

Leu Ile Lys Cys Phe Glu Ile Pro Asp Leu Leu Asp Pro Ser Ile Ile
450                 455                 460

Tyr Ser Asp Lys Ser His Ser Met Asn Arg Ser Glu Val Leu Lys His
465                 470                 475                 480

Val Arg Met Asn Pro Asn Thr Pro Ile Pro Ser Lys Lys Val Leu Gln
            485                 490                 495

Thr Met Leu Asp Thr Lys Ala Thr Asn Trp Lys Glu Phe Leu Lys Glu
            500                 505                 510

Ile Asp Glu Lys Gly Leu Asp Asp Asp Leu Ile Ile Gly Leu Lys
        515                 520                 525

Gly Lys Glu Arg Glu Leu Lys Leu Ala Gly Arg Phe Phe Ser Leu Met
530                 535                 540

Ser Trp Lys Leu Arg Glu Tyr Phe Val Ile Thr Glu Tyr Leu Ile Lys
545                 550                 555                 560

Thr His Phe Val Pro Met Phe Lys Gly Leu Thr Met Ala Asp Asp Leu
            565                 570                 575

Thr Ala Val Ile Lys Lys Met Leu Asp Ser Ser Ser Gly Gln Gly Leu
            580                 585                 590

Lys Ser Tyr Glu Ala Ile Cys Ile Ala Asn His Ile Asp Tyr Glu Lys
        595                 600                 605

Trp Asn Asn His Gln Arg Lys Leu Ser Asn Gly Pro Val Phe Arg Val
```

-continued

```
              610                 615                 620
Met Gly Gln Phe Leu Gly Tyr Pro Ser Leu Ile Glu Arg Thr His Glu
625                 630                 635                 640

Phe Phe Glu Lys Ser Leu Ile Tyr Tyr Asn Gly Arg Pro Asp Leu Met
                    645                 650                 655

Arg Val His Asn Asn Thr Leu Ile Asn Ser Thr Ser Gln Arg Val Cys
                660                 665                 670

Trp Gln Gly Gln Glu Gly Gly Leu Glu Gly Leu Arg Gln Lys Gly Trp
                675                 680                 685

Ser Ile Leu Asn Leu Leu Val Ile Gln Arg Glu Ala Lys Ile Arg Asn
690                 695                 700

Thr Ala Val Lys Val Leu Ala Gln Gly Asp Asn Gln Val Ile Cys Thr
705                 710                 715                 720

Gln Tyr Lys Thr Lys Ser Arg Asn Val Val Glu Leu Gln Gly Ala
                    725                 730                 735

Leu Asn Gln Met Val Ser Asn Asn Glu Lys Ile Met Thr Ala Ile Lys
                740                 745                 750

Ile Gly Thr Gly Lys Leu Gly Leu Leu Ile Asn Asp Asp Glu Thr Met
                755                 760                 765

Gln Ser Ala Asp Tyr Leu Asn Tyr Gly Lys Ile Pro Ile Phe Arg Gly
770                 775                 780

Val Ile Arg Gly Leu Glu Thr Lys Arg Trp Ser Arg Val Thr Cys Val
785                 790                 795                 800

Thr Asn Asp Gln Ile Pro Thr Cys Ala Asn Ile Met Ser Ser Val Ser
                    805                 810                 815

Thr Asn Ala Leu Thr Val Ala His Phe Ala Glu Asn Pro Ile Asn Ala
                820                 825                 830

Met Ile Gln Tyr Asn Tyr Phe Gly Thr Phe Ala Arg Leu Leu Leu Met
835                 840                 845

Met His Asp Pro Ala Leu Arg Gln Ser Leu Tyr Glu Val Gln Asp Lys
850                 855                 860

Ile Pro Gly Leu His Ser Ser Thr Phe Lys Tyr Ala Met Leu Tyr Leu
865                 870                 875                 880

Asp Pro Ser Ile Gly Gly Val Ser Gly Met Ser Leu Ser Arg Phe Leu
                    885                 890                 895

Ile Arg Ala Phe Pro Asp Pro Val Thr Glu Ser Leu Ser Phe Trp Arg
                900                 905                 910

Phe Ile His Val His Ala Arg Ser Glu His Leu Lys Glu Met Ser Ala
                915                 920                 925

Val Phe Gly Asn Pro Glu Ile Ala Lys Phe Arg Ile Thr His Ile Asp
930                 935                 940

Lys Leu Val Glu Asp Pro Thr Ser Leu Asn Ile Ala Met Gly Met Ser
945                 950                 955                 960

Pro Ala Asn Leu Leu Lys Thr Glu Val Lys Lys Cys Leu Ile Glu Ser
                    965                 970                 975

Arg Gln Thr Ile Arg Asn Gln Val Ile Lys Asp Ala Thr Ile Tyr Leu
                980                 985                 990

Tyr His Glu Glu Asp Arg Leu Arg Ser Phe Leu Trp Ser Ile Asn Pro
                995                 1000                1005

Leu Phe Pro Arg Phe Leu Ser Glu Phe Lys Ser Gly Thr Phe Leu
        1010                1015                1020

Gly Val Ala Asp Gly Leu Ile Ser Leu Phe Gln Asn Ser Arg Thr
        1025                1030                1035
```

-continued

```
Ile Arg Asn Ser Phe Lys Lys Lys Tyr His Arg Glu Leu Asp Asp
1040                1045                1050

Leu Ile Val Arg Ser Glu Val Ser Ser Leu Thr His Leu Gly Lys
1055                1060                1065

Leu His Leu Arg Arg Gly Ser Cys Lys Met Trp Thr Cys Ser Ala
1070                1075                1080

Thr His Ala Asp Thr Leu Arg Tyr Lys Ser Trp Gly Arg Thr Val
1085                1090                1095

Ile Gly Thr Thr Val Pro His Pro Leu Glu Met Leu Gly Pro Gln
1100                1105                1110

His Arg Lys Glu Thr Pro Cys Ala Pro Cys Asn Thr Ser Gly Phe
1115                1120                1125

Asn Tyr Val Ser Val His Cys Pro Asp Gly Ile His Asp Val Phe
1130                1135                1140

Ser Ser Arg Gly Pro Leu Pro Ala Tyr Leu Gly Ser Lys Thr Ser
1145                1150                1155

Glu Ser Thr Ser Ile Leu Gln Pro Trp Glu Arg Glu Ser Lys Val
1160                1165                1170

Pro Leu Ile Lys Arg Ala Thr Arg Leu Arg Asp Ala Ile Ser Trp
1175                1180                1185

Phe Val Glu Pro Asp Ser Lys Leu Ala Met Thr Ile Leu Ser Asn
1190                1195                1200

Ile His Ser Leu Thr Gly Glu Glu Trp Thr Lys Arg Gln His Gly
1205                1210                1215

Phe Lys Arg Thr Gly Ser Ala Leu His Arg Phe Ser Thr Ser Arg
1220                1225                1230

Met Ser His Gly Gly Phe Ala Ser Gln Ser Thr Ala Ala Leu Thr
1235                1240                1245

Arg Leu Met Ala Thr Thr Asp Thr Met Arg Asp Leu Gly Asp Gln
1250                1255                1260

Asn Phe Asp Phe Leu Phe Gln Ala Thr Leu Leu Tyr Ala Gln Ile
1265                1270                1275

Thr Thr Thr Val Ala Arg Asp Gly Trp Ile Thr Ser Cys Thr Asp
1280                1285                1290

His Tyr His Ile Ala Cys Lys Ser Cys Leu Arg Pro Ile Glu Glu
1295                1300                1305

Ile Thr Leu Asp Ser Ser Met Asp Tyr Thr Pro Pro Asp Val Ser
1310                1315                1320

His Val Leu Lys Thr Trp Arg Asn Gly Glu Gly Ser Trp Gly Gln
1325                1330                1335

Glu Ile Lys Gln Ile Tyr Pro Leu Glu Gly Asn Trp Lys Asn Leu
1340                1345                1350

Ala Pro Ala Glu Gln Ser Tyr Gln Val Gly Arg Cys Ile Gly Phe
1355                1360                1365

Leu Tyr Gly Asp Leu Ala Tyr Arg Lys Ser Thr His Ala Glu Asp
1370                1375                1380

Ser Ser Leu Phe Pro Leu Ser Ile Gln Gly Arg Ile Arg Gly Arg
1385                1390                1395

Gly Phe Leu Lys Gly Leu Leu Asp Gly Leu Met Arg Ala Ser Cys
1400                1405                1410

Cys Gln Val Ile His Arg Arg Ser Leu Ala His Leu Lys Arg Pro
1415                1420                1425

Ala Asn Ala Val Tyr Gly Gly Leu Ile Tyr Leu Ile Asp Lys Leu
1430                1435                1440
```

```
Ser Val Ser Pro Pro Phe Leu Ser Leu Thr Arg Ser Gly Pro Ile
    1445             1450                 1455

Arg Asp Glu Leu Glu Thr Ile Pro His Lys Ile Pro Thr Ser Tyr
    1460             1465                 1470

Pro Thr Ser Asn Arg Asp Met Gly Val Ile Val Arg Asn Tyr Phe
    1475             1480                 1485

Lys Tyr Gln Cys Arg Leu Ile Glu Lys Gly Lys Tyr Arg Ser His
    1490             1495                 1500

Tyr Ser Gln Leu Trp Leu Phe Ser Asp Val Leu Ser Ile Asp Phe
    1505             1510                 1515

Ile Gly Pro Phe Ser Ile Ser Thr Thr Leu Leu Gln Ile Leu Tyr
    1520             1525                 1530

Lys Pro Phe Leu Ser Gly Lys Asp Lys Asn Glu Leu Arg Glu Leu
    1535             1540                 1545

Ala Asn Leu Ser Ser Leu Leu Arg Ser Gly Glu Gly Trp Glu Asp
    1550             1555                 1560

Ile His Val Lys Phe Phe Thr Lys Asp Ile Leu Leu Cys Pro Glu
    1565             1570                 1575

Glu Ile Arg His Ala Cys Lys Phe Gly Ile Ala Lys Asp Asn Asn
    1580             1585                 1590

Lys Asp Met Ser Tyr Pro Pro Trp Gly Arg Glu Ser Arg Gly Thr
    1595             1600                 1605

Ile Thr Thr Ile Pro Val Tyr Tyr Thr Thr Pro Tyr Pro Lys
    1610             1615                 1620

Met Leu Glu Met Pro Pro Arg Ile Gln Asn Pro Leu Leu Ser Gly
    1625             1630                 1635

Ile Arg Leu Gly Gln Leu Pro Thr Gly Ala His Tyr Lys Ile Arg
    1640             1645                 1650

Ser Ile Leu His Gly Met Gly Ile His Tyr Arg Asp Phe Leu Ser
    1655             1660                 1665

Cys Gly Asp Gly Ser Gly Gly Met Thr Ala Ala Leu Leu Arg Glu
    1670             1675                 1680

Asn Val His Ser Arg Gly Ile Phe Asn Ser Leu Leu Glu Leu Ser
    1685             1690                 1695

Gly Ser Val Met Arg Gly Ala Ser Pro Glu Pro Ser Ala Leu
    1700             1705                 1710

Glu Thr Leu Gly Gly Asp Lys Ser Arg Cys Val Asn Gly Glu Thr
    1715             1720                 1725

Cys Trp Glu Tyr Pro Ser Asp Leu Cys Asp Pro Arg Thr Trp Asp
    1730             1735                 1740

Tyr Phe Leu Arg Leu Lys Ala Gly Leu Gly Leu Gln Ile Asp Leu
    1745             1750                 1755

Ile Val Met Asp Met Glu Val Arg Asp Ser Ser Thr Ser Leu Lys
    1760             1765                 1770

Ile Glu Thr Asn Val Arg Asn Tyr Val His Arg Ile Leu Asp Glu
    1775             1780                 1785

Gln Gly Val Leu Ile Tyr Lys Thr Tyr Gly Thr Tyr Ile Cys Glu
    1790             1795                 1800

Ser Glu Lys Asn Ala Val Thr Ile Leu Gly Pro Met Phe Lys Thr
    1805             1810                 1815

Val Asp Leu Val Gln Thr Glu Phe Ser Ser Ser Gln Thr Ser Glu
    1820             1825                 1830

Val Tyr Met Val Cys Lys Gly Leu Lys Lys Leu Ile Asp Glu Pro
```

-continued

```
                            1835                1840                1845

Asn Pro Asp Trp Ser Ser Ile Asn Glu Ser Trp Lys Asn Leu Tyr
    1850                1855                1860

Ala Phe Gln Ser Ser Glu Gln Glu Phe Ala Arg Ala Lys Lys Val
    1865                1870                1875

Ser Thr Tyr Phe Thr Leu Thr Gly Ile Pro Ser Gln Phe Ile Pro
    1880                1885                1890

Asp Pro Phe Val Asn Ile Glu Thr Met Leu Gln Ile Phe Gly Val
    1895                1900                1905

Pro Thr Gly Val Ser His Ala Ala Ala Leu Lys Ser Ser Asp Arg
    1910                1915                1920

Pro Ala Asp Leu Leu Thr Ile Ser Leu Phe Tyr Met Ala Ile Ile
    1925                1930                1935

Ser Tyr Tyr Asn Ile Asn His Ile Arg Val Gly Pro Ile Pro Pro
    1940                1945                1950

Asn Pro Pro Ser Asp Gly Ile Ala Gln Asn Val Gly Ile Ala Ile
    1955                1960                1965

Thr Gly Ile Ser Phe Trp Leu Ser Leu Met Glu Lys Asp Ile Pro
    1970                1975                1980

Leu Tyr Gln Gln Cys Leu Ala Val Ile Gln Gln Ser Phe Pro Ile
    1985                1990                1995

Arg Trp Glu Ala Val Ser Val Lys Gly Gly Tyr Lys Gln Lys Trp
    2000                2005                2010

Ser Thr Arg Gly Asp Gly Leu Pro Lys Asp Thr Arg Ile Ser Asp
    2015                2020                2025

Ser Leu Ala Pro Ile Gly Asn Trp Ile Arg Ser Leu Glu Leu Val
    2030                2035                2040

Arg Asn Gln Val Arg Leu Asn Pro Phe Asn Glu Ile Leu Phe Asn
    2045                2050                2055

Gln Leu Cys Arg Thr Val Asp Asn His Leu Lys Trp Ser Asn Leu
    2060                2065                2070

Arg Arg Asn Thr Gly Met Ile Glu Trp Ile Asn Arg Arg Ile Ser
    2075                2080                2085

Lys Glu Asp Arg Ser Ile Leu Met Leu Lys Ser Asp Leu His Glu
    2090                2095                2100

Glu Asn Ser Trp Arg Asp
    2105

<210> SEQ ID NO 6
<211> LENGTH: 13455
<212> TYPE: DNA
<213> ORGANISM: Artificial Sequence
<220> FEATURE:
<223> OTHER INFORMATION: Synthetic DNA encoding VSV-rp30

<400> SEQUENCE: 6
acgaagacaa acaaaccatt attatcatta aaaggctcag gagaaacttt aacagtaatc      60
aaaatgtctg ttacagtcaa gagaatcatt gacaacacag tcgtagttcc aaaacttcct     120
gcaaatgagg atccagtgga atacccggca gattacttca aaaatcaaa ggagattcct     180 ctttacatca atactacaaa aagtttgtca gatctaagag atatgtcta ccaaggcctc     240 aaatccggaa atgtatcaat catacatgtc aacagctact tgtatggagc attaaaggac     300
atccggggta agttggataa agattggtca agtttcggaa taaacatcgg gaaagcaggg     360
gatacaatcg gaatatttga ccttgtatcc ttgaaagccc tggacggcgt acttccagat     420
```

```
ggagtatcgg atgcttccag aaccagcgca gatgacaaat ggttgccttt gtatctactt    480
ggcttataca gagtgggcag aacacaaatg cctgaataca gaaaaaagct catggatggg    540
ctgacaaatc aatgcaaaat gatcaatgaa cagtttgaac ctcttgtgcc agaaggtcgt    600
gacattttg atgtgtgggg aaatgacagt aattacacaa aaattgtcgc tgcagtggac     660
atgttcttcc acatgttcaa aaacatgaa tgtgcctcgt tcagatacgg aactattgtt    720
tccagattca aagattgtgc tgcattggca acatttggac acctctgcaa ataaccgga    780
atgtctacag aagatgtaac gacctggatc ttgaaccgag aagttgcaga tgaaatggtc    840
caaatgatgc ttccaggcca agaaattgac aaggccgatt catacatgcc ttatttgatc    900
gactttggat tgtcttctaa gtctccatat tcttccgtca aaaaccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgccg acttggcaca acagttttgt gttggagata caaatacac tccagatgat   1140
agtaccggag gattgacgac taatgcaccg ccacaaggca gagatgtggt cgaatggctc   1200
ggatggtttg aagatcaaaa cagaaaaccg actcctgata tgatgcagta tgcgaaaaga   1260
gcagtcatgt cactgcaagg cctaagagag aagacaattg gcaagtatgc taagtcagaa   1320
tttgacaaat gacccctataa ttctcagatc acctattata tattatgcta catatgaaaa   1380
aaactaacag atatcatgga taatctcaca aaagttcgtg agtatctcaa gtcctattct   1440
cgtctggatc aggcggtagg agagatagat gagatcgaag cacaacgagc tgaaaagtcc   1500
aattatgagt tgttccaaga ggatggagtg aagagcata ctaagccctc ttattttcag    1560
gcagcagatt attctgacac agaatctgaa ccagaaattg aagacaatca aggcttgtat   1620
gcaccagatc cagaagctga gcaagttgaa ggctttatac aggggccttt agatgactat   1680
gcagatgagg aagtggatgt tgtatttact tcggactgga acagcctga gcttgaatct    1740
gacgagcatg gaaagacctt acggttgaca ttgccagagg gtttaagtgg agagcagaaa   1800
tcccagtggc tttcgacgat taaagcagtc gtgcaaagtg ccaaatactg gaatctggca   1860
gagtgcacat ttgaagcatc gggagaaggg gtcattatga aggagcgcca gataactccg   1920
gatgtatata aggtcactcc agtgatgaac acacatccgt cccaatcaga agcagtatca   1980
gatgtttggt ctctctcaaa gacatccatg actttccaac caagaaagc aagtcttcag    2040
cctctcacca tatccttgga tgaattgttc tcatctagag gagagttcat ctctgtcgga   2100
ggtgacggac gaatgtctca taaagaggcc atcctgctcg gcctgagata caaaaagttg   2160
tacaatcagg cgagagtcaa atattctctg tagactatga aaaaagtaa cagatatcac    2220
gatctaagtg ttatcccaat ccattcatca tgagttcctt aaagaagatt ctcggtctga   2280
agggaaagg taagaaatct aagaaattag ggatcgcacc ccccccttat gaagaggaca    2340
ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga acgtcccctt ctacaaaatc ttggcttttt   2580
tgggttcttc taatctaaag gccactccag cggtattggc agatcaaggt caaccagagt   2640
atcacgctca ctgcgaaggc agggcttatt tgccacatag gatggggaag acccctccca   2700
tgctcaatgt accagagcac ttcagaagac cattcaatat aggtctttac aagggaacga   2760
ttgagctcac aatgaccatc tacgatgatg agtcactgga agcagctcct atgatctggg   2820
```

```
atcatttcaa ttcttccaaa tttttctgatt tcagagagaa ggccttaatg tttggcctga    2880
ttgtcgagaa aaaggcatct ggagcgtggg tcctggactc tatcggccac ttcaaatgag    2940
ctagtctaac ttctagcttc tgaacaatcc ccggtttact cagtctcccc taattccagc    3000
ctctcgaaca actaatatcc tgtcttttct atccctatga aaaaaactaa cagagatcga    3060
tctgtttacg cgtcactatg aagtgccttt tgtacttagc cttttttattc attggggtga    3120 attgcaagtt caccatagtt tttccacaca accaaaaagg aaactggaaa aatgttcctt    3180
ctaattacca ttattgcccg tcaagctcag atttaaattg gcataatgac ttaataggca    3240
cagccttaca agtcaaaatg cccaagagtc acaaggctat tcaagcagac ggttggatgt    3300
gtcatgcttc caaatgggtc actacttgtg atttccgctg gtatggaccg aagtatataa    3360
cacattccat ccgatccttc actccatctg tagaacaatg caaggaaagc attgaacaaa    3420
cgaaacaagg aacttggctg aatccaggct tccctcctca aagttgtgga tatgcaactg    3480
tgacggatgc cgaagcagtg attgtccagg tgactcctca ccatgtgctg gttgatgaat    3540
acacaggaga atgggttgat tcacagttca tcaacggaaa atgcagcaat tacatatgcc    3600
ccactgtcca taactctaca acctggcatt ctgactataa ggtcaaaggg ctatgtgatt    3660
ctaacctcat ttccatggac atcaccttct tctcagagga cggagagcta tcatccctgg    3720
gaaaggaggg cacagggttc agaagtaact actttgctta tgaaactgga ggcaaggcct    3780
gcaaaatgca atactgcaag cattggggag tcagactccc atcaggtgtc tggttcgaga    3840
tggctgataa ggatctcttt gctgcagcca gattccctga atgcccagaa gggtcaagta    3900
tctctgctcc atctcagacc tcagtggatg taagtctaat tcaggacgtt gagaggatct    3960
tggattattc cctctgccaa gaaacctgga gcaaaatcag agcgggtctt ccaatctctc    4020
cagtggatct cagctatctt gctcctaaaa acccaggaac cggtcctgct ttcaccataa    4080
tcaatggtac cctaaaatac tttgagacca gatacatcag agtcgatatt gctgctccaa    4140
tcctctcaag aatggtcgga atgatcagtg aactaccac agaaagggaa ctgtgggatg    4200
actgggcacc atatgaagac gtggaaattg gacccaatgg agttctgagg accagttcag    4260
gatataagtt tccttatac atgattggac atggtatgtt ggactccgat cttcatctta    4320
gctcaaaggc tcaggtgttc gaacatcctc acattcaaga cgctgcttcg caacttcctg    4380
atgatgagag tttatttttt ggtgatactg ggctatccaa aaatccaatc gagcttgtag    4440
aaggttggtt cagtagttgg aaaagctcta ttgcctcttt tttctttatc atagggttaa    4500
tcattggact attcttggtt ctccgagttg gtatccatct ttgcattaaa ttaaagcaca    4560
ccaagaaaag acagatttat acagacatag agatgaaccg acttggaaag taactcaaat    4620
cctgctaggt atgaaaaaa ctaacagata tcacgctcga gactatgaag tgcctttgt    4680 acttagcctt tttattcatt ggggtgaatt gcaagttcac catagttttt ccacacaacc    4740
aaaaaggaaa ctgaaaaat gttccttcta attaccatta ttgcccgtca agctcagatt    4800
taaattggca taatgactta ataggcacag ccttacaagt caaaatgccc aagagtcaca    4860
aggctattca agcagacggt tggatgtgtc atgcttccaa atgggtcact acttgtgatt    4920
tccgctggta tggaccgaag tatataacac attccatccg atccttcact ccatctgtag    4980
aacaatgcaa ggaaagcatt gaacaaacga acaaggaac ttggctgaat ccaggcttcc    5040
ctcctcaaag ttgtggatat gcaactgtga cggatgccga agcagtgatt gtccaggtga    5100
ctcctcacca tgtgctggtt gatgaataca caggagaatg ggttgattca cagttcatca    5160
acggaaaatg cagcaattac atatgcccca ctgtccataa ctctacaacc tggcattctg    5220
```

-continued

```
actataaggt caaagggcta tgtgattcta acctcatttc catggacatc accttcttct    5280
cagaggacgg agagctatca tccctgggaa aggagggcac agggttcaga agtaactact    5340
ttgcttatga aactggaggc aaggcctgca aaatgcaata ctgcaagcat ggggagtca     5400
gactcccatc aggtgtctgg ttcgagatgg ctgataagga tctctttgct gcagccagat    5460
tccctgaatg cccagaaggg tcaagtatct ctgctccatc tcagacctca gtggatgtaa    5520
gtctaattca ggacgttgag aggatcttgg attattccct ctgccaagaa acctggagca    5580
aaatcagagc gggtcttcca atctctccag tggatctcag ctatcttgct cctaaaaacc    5640
caggaaccgg tcctgctttc accataatca atggtaccct aaaatacttt gagaccagat    5700
acatcagagt cgatattgct gctccaatcc tctcaagaat ggtcggaatg atcagtggaa    5760
ctaccacaga aagggaactg tgggatgact gggcaccata tgaagacgtg gaaattggac    5820
ccaatggagt tctgaggacc agttcaggat ataagtttcc tttatacatg attggacatg    5880
gtatgttgga ctccgatctt catcttagct caaaggctca ggtgttcgaa catcctcaca    5940
ttcaagacgc tgcttcgcaa cttcctgatg atgagagttt attttttggt gatactgggc    6000
tatccaaaaa tccaatcgag cttgtagaag gttggttcag tagttggaaa agctctattg    6060
cctcttttt ctttatcata gggttaatca ttggactatt cttggttctc cgagttggta    6120
tccatctttg cattaaatta aagcacacca agaaaagaca gatttataca gacatagaga    6180
tgaaccgact tggaaagatg gtgagcaagg gcgaggagct gttcaccggg gtggtgccca    6240
tcctggtcga gctggacggc gacgtaaacg gccacaagtt cagcgtgtcc ggcgagggcg    6300
agggcgatgc cacctacggc aagctgaccc tgaagttcat ctgcaccacc ggcaagctgc    6360
ccgtgccctg gcccaccctc gtgaccaccc tgacctacgg cgtgcagtgc ttcagccgct    6420
accccgacca catgaagcag cacgacttct tcaagtccgc catgcccgaa ggctacgtcc    6480
aggagcgcac catcttcttc aaggacgacg gcaactacaa gacccgcgcc gaggtgaagt    6540
tcgagggcga caccctggtg aaccgcatcg agctgaaggg catcgacttc aaggaggacg    6600
gcaacatcct ggggcacaag ctggagtaca actacaacag ccacaacgtc tatatcatgg    6660
ccgacaagca gaagaacggc atcaaggtga acttcaagat ccgccacaac atcgaggacg    6720
gcagcgtgca gctcgccgac cactaccagc agaacacccc catcggcgac ggccccgtgc    6780
tgctgcccga caaccactac ctgagcaccc agtccgccct gagcaaagac cccaacgaga    6840
agcgcgatca catggtcctg ctggagttcg tgaccgccgc cgggatcact ctcggcatgg    6900
acgagctgta caagtaagct agccagattc ttcatgtttg accaaatca acttgtgata     6960
ccatgctcaa agaggcctca attatatttg agttttaat ttttatgaaa aaaactaaca     7020
gcaatcatga agtccacga ttttgagacc gacgagttca atgatttcaa tgaagatgac     7080
tatgccacaa gagaattcct gaatcccgat gagcgcatga cgtacttgaa tcatgctgat    7140
tacaacctga attctcctct aattagtgat gatattgaca atttaatcag gaaattcaat    7200
tctcttccaa ttccctcgat gtgggatagt aagaactggg atggagttct tgagatgtta    7260
acgtcatgtc aagccaatcc catcccaaca tctcagatgc ataaatggat gggaagttgg    7320
ttaatgtctg ataatcatga tgccagtcaa gggtatagtt tttacatga agtggacaaa     7380
gaggcagaaa taacatttga cgtggtggag accttcatcc gcggctgggg caacaaacca    7440
attgaataca tcaaaaagga aagatggact gactcattca aaattctcgc ttatttgtgt    7500
caaaagtttt tggacttaca caagttgaca ttaatcttaa atgctgtctc tgaggtggaa    7560
ttgctcaact tggcgaggac tttcaaaggc aaagtcagaa gaagttctca tggaacgaac    7620
```

```
atatgcagga ttagggttcc cagcttgggt cctacttta tttcagaagg atgggcttac    7680
ttcaagaaac tttatattct aatggaccga aactttctgt taatggtcaa agatgtgatt    7740
atagggagga tgcaaacggt gctatccatg gtatgtagaa tagacaacct gttctcagag    7800
caagacatct tctcccttct aaatatctac agaattggag ataaaattgt ggagaggcag    7860 ggaattttt cttatgactt gattaaaatg gtggaaccga tatgcaactt gaagctgatg    7920
aaattagcaa gagaatcaag gcctttagtc ccacaattcc ctcattttga aaatcatatc    7980
aagacttctg ttgatgaagg ggcaaaaatt gaccgaggta taagattcct ccatgatcag    8040
ataatgagtg tgaaaacagt ggatctcaca ctggtgattt atggatcgtt cagacattgg    8100
ggtcatcctt ttatagatta ttacactgga ctagaaaaat tacattccca agtaaccatg    8160
aagaaagata ttgatgtgtc atatgcaaaa gcacttgcaa gtgatttagc tcggattgtt    8220
ctatttcaac agttcaatga tcataaaaag tggttcgtga atggagactt gctccctcat    8280
gatcatccct ttaaaagtca tgttaaagaa aatacatggc ccacagctgc tcaagttcaa    8340
gattttggag ataaatggca tgaacttccg ctgattaaat gttttgaaat acccgactta    8400
ctagacccat cgataatata ctctgacaaa agtcattcaa tgataggtc agaggtgttg    8460 aaacatgtcc gaatgaatcc gaacactcct atccctagta aaaggtgtt gcagactatg    8520 ttggacacaa aggctaccaa ttggaaagaa tttcttaaag agattgatga aagggctta    8580 gatgatgatg atctaattat tggtcttaaa ggaaaggaga gggaactgaa gttggcaggt    8640
agatttttct ccctaatgtc ttggaaattg cgagaatact tgtaattac cgaatatttg    8700 ataaagactc atttcgtccc tatgttttaaa ggcctgacaa tggcggacga tctaactgca    8760
gtcattaaaa agatgttaga ttcctcatcc ggccaaggat tgaagtcata tgaggcaatt    8820
tgcatagcca atcacattga ttacgaaaaa tggaataacc accaaaggaa gttatcaaac    8880
ggcccagtgt tccgagttat gggccagttc ttaggttatc catccttaat cgagagaact    8940 catgaattt ttgagaaaag tcttatatac tacaatggaa gaccagactt gatgcgtgtt    9000
cacaacaaca cactgatcaa ttcaacctcc caacgagttt gttggcaagg acaagagggt    9060
ggactggaag gtctacggca aaaaggatgg agtatcctca atctactggt tattcaaaga    9120
gaggctaaaa tcagaaacac tgctgtcaaa gtcttggcac aaggtgataa tcaagttatt    9180
tgcacacagt ataaaacgaa gaaatcgaga acgttgtag aattacaggg tgctctcaat    9240
caaatggttt ctaataatga gaaaattatg actgcaatca aaatagggac agggaagtta    9300
ggacttttga taaatgacga tgagactatg caatctgcag attacttgaa ttatggaaaa    9360
ataccgattt tccgtggagt gattagaggg ttagagacca agagatggtc acgagtgact    9420
tgtgtcacca atgaccaaat acccacttgt gctaatataa tgagctcagt ttccacaaat    9480
gctctcaccg tagctcattt tgctgagaac ccaatcaatg ccatgataca gtacaattat    9540
tttgggacat ttgctagact cttgttgatg atgcatgatc ctgctcttcg tcaatcattg    9600
tatgaagttc aagataagat accgggcttg cacagttcta ctttcaaata cgccatgttg    9660
tatttggacc cttccattgg aggagtgtcg ggcatgtctt tgtccaggtt tttgattaga    9720
gccttcccag atcccgtaac agaaagtctc tcattctgga gattcatcca tgtacatgct    9780
cgaagtgagc atctgaagga gatgagtgca gtatttggaa accccgagat agccaagttt    9840
cgaataactc acatagacaa gctagtagaa gatccaacct ctctgaacat cgctatggga    9900
atgagtccag cgaacttgtt aaagactgag gttaaaaaat gcttaatcga atcaagacaa    9960
accatcagga accaggtgat taaggatgca accatatatt tgtatcatga agaggatcgg   10020
```

```
ctcagaagtt tcttatggtc aataaatcct ctgttccctg gattttaag tgaattcaaa   10080 tcaggcactt ttttgggagt cgcagacggg ctcatcagtc tatttcaaaa ttctcgtact   10140
attcggaact cctttaagaa aaagtatcat agggaattgg atgatttgat tgtgaggagt   10200
gaggtatcct ctttgacaca tttagggaaa cttcatttga aagggggatc atgtaaaatg   10260
tggacatgtt cagctactca tgctgacaca ttaagataca aatcctgggg ccgtacagtt   10320
attgggacaa ctgtacccca tccattagaa atgttgggtc cacaacatcg aaaagagact   10380
ccttgtgcac catgtaacac atcagggttc aattatgttt ctgtgcattg tccagacggg   10440
atccatgacg tctttagttc acggggacca ttgcctgctt atctagggtc taaaacatct   10500
gaatctacat ctattttgca gccttgggaa agggaaagca aagtcccact gattaaaaga   10560
gctacacgtc ttagagatgc tatctcttgg tttgttgaac ccgactctaa actagcaatg   10620
actatacttt ctaacatcca ctctttaaca ggcgaagaat ggaccaaaag gcagcatggg   10680
ttcaaaagaa cagggtctgc ccttcatagg ttttcgacat ctcggatgag ccatggtggg   10740
ttcgcatctc agagcactgc agcattgacc aggttgatgg caactacaga caccatgagg   10800
gatctgggag atcagaattt cgacttttta ttccaagcaa cgttgctcta tgctcaaatt   10860
accaccactg ttgcaagaga cggatggatc accagttgta cagatcatta tcatattgcc   10920
tgtaagtcct gtttgagacc catagaagag atcaccctgg actcaagtat ggactacacg   10980
cccccagatg tatcccatgt gctgaagaca tggaggaatg gggaaggttc gtggggacaa   11040
gagataaaac agatctatcc tttagaaggg aattggaaga atttagcacc tgctgagcaa   11100
tcctatcaag tcggcagatg tataggtttt ctatatggag acttggcgta tagaaaatct   11160
actcatgccg aggacagttc tctatttcct ctatctatac aaggtcgtat tagaggtcga   11220
ggtttcttaa aagggttgct agacggatta atgagagcaa gttgctgcca agtaatacac   11280
cggagaagtc tggctcattt gaagaggccg gccaacgcag tgtacggagg tttgatttac   11340
ttgattgata aattgagtgt atcacctcca ttcctttctc ttactagatc aggacctatt   11400
agagacgaat tagaaacgat tccccacaag atcccaacct cctatccgac aagcaaccgt   11460
gatatggggg tgattgtcag aaattacttc aaataccaat gccgtctaat tgaaaaggga   11520
aaatacagat cacattattc acaattatgg ttattctcag atgtcttatc catagacttc   11580
attggaccat tctctatttc caccaccctc ttgcaaatcc tatacaagcc atttttatct   11640
gggaaagata agaatgagtt gagagagctg gcaaatcttt cttcattgct aagatcagga   11700
gaggggtggg aagacataca tgtgaaattc ttcaccaagg acatattatt gtgtccagag   11760
gaaatcagac atgcttgcaa gttcgggatt gctaaggata ataataaaga catgagctat   11820 ccccttggg gaagggaatc cagagggaca attacaacaa tccctgttta ttatacgacc   11880
accccttacc caaagatgct agagatgcct ccaagaatcc aaaatcccct gctgtccgga   11940
atcaggttgg gccaattacc aactggcgct cattataaaa ttcggagtat attacatgga   12000
atgggaatcc attacaggga cttcttgagt tgtggagacg gctccggagg gatgactgct   12060
gcattactac gagaaaatgt gcatagcaga ggaatattca atagtctgtt agaattatca   12120
gggtcagtca tgcgaggcgc ctctcctgag cccccccagtg ccctagaaac tttaggagga   12180
gataaatcga gatgtgtaaa tggtgaaaca tgttgggaat atccatctga cttatgtgac   12240
ccaaggactt gggactattt cctccgactc aaagcaggct tggggcttca aattgattta   12300
attgtaatgg atatggaagt tcgggattct tctactagcc tgaaaattga gacgaatgtt   12360
agaaattatg tgcaccggat tttggatgag caaggagttt aatctacaa gacttatgga   12420
```

```
acatatattt gtgagagcga aaagaatgca gtaacaatcc ttggtcccat gttcaagacg    12480
gtcgacttag ttcaaacaga atttagtagt tctcaaacgt ctgaagtata tatggtatgt    12540
aaaggtttga agaaattaat cgatgaaccc aatcccgatt ggtcttccat caatgaatcc    12600
tggaaaaacc tgtacgcatt ccagtcatca gaacaggaat tgccagagc aaagaaggtt    12660 agtacatact ttaccttgac aggtattccc tcccaattca ttcctgatcc ttttgtaaac    12720
attgagacta tgctacaaat attcggagta cccacgggtg tgtctcatgc ggctgcctta    12780
aaatcatctg atagacctgc agatttattg accattagcc tttttttatat ggcgattata    12840 tcgtattata acatcaatca tatcagagta ggaccgatac ctccgaaccc cccatcagat    12900
ggaattgcac aaaatgtggg gatcgctata actggtataa gcttttggct gagtttgatg    12960
gagaaagaca ttccactata tcaacagtgt ttagcagtta ccagcaatc attcccgatt    13020 aggtgggagg ctgtttcagt aaaaggagga tacaagcaga agtggagtac tagaggtgat    13080
gggctcccaa aagatacccg aatttcgac tccttggccc caatcgggaa ctggatcaga    13140
tctctggaat tggtccgaaa ccaagttcgt ctaaatccat tcaatgagat cttgttcaat    13200
cagctatgtc gtacagtgga taatcatttg aaatggtcaa atttgcgaag aaacacagga    13260
atgattgaat ggatcaatag acgaatttca aaagaagacc ggtctatact gatgttgaag    13320
agtgacctac acgaggaaaa ctcttggaga gattaaaaaa tcatgaggag actccaaact    13380
ttaagtatga aaaaacttt gatccttaag accctcttgt ggttttatt ttttatctgg    13440 ttttgtggtc ttcgt                                                    13455

<210> SEQ ID NO 7
<211> LENGTH: 798
<212> TYPE: DNA
<213> ORGANISM: Artificial Sequence
<220> FEATURE:
<223> OTHER INFORMATION: Synthetic DNA encoding VSV-rp30  mutant P
      protein

<400> SEQUENCE: 7
atggataatc tcacaaaagt tcgtgagtat ctcaagtcct attctcgtct ggatcaggcg      60
gtaggagaga tagatgagat cgaagcacaa cgagctgaaa agtccaatta tgagttgttc     120
caagaggatg gagtggaaga gcatactaag ccctcttatt ttcaggcagc agatgattct     180
gacacagaat ctgaaccaga aattgaagac aatcaaggct tgtatgcacc agatccagaa     240
gctgagcaag ttgaaggctt tatacagggg cctttagatg actatgcaga tgaggaagtg     300
gatgttgtat ttacttcgga ctggaaacag cctgagcttg aatctgacga gcatggaaag     360
accttacggt tgacattgcc agagggttta agtggagagc agaaatccca gtggctttcg     420
acgattaaag cagtcgtgca aagtgccaaa tactggaatc tggcagagtg cacatttgaa     480
gcatcgggag aagggtcat tatgaaggag cgccagataa ctccggatgt atataaggtc     540
actccagtga tgaacacaca tccgtcccaa tcagaagcag tatcagatgt ttggtctctc     600
tcaaagacat ccatgacttt ccaacccaag aaagcaagtc ttcagcctct caccatatcc     660
ttggatgaat tgttctcatc tagaggagag ttcatctctg tcggaggtga cggacgaatg     720
tctcataaag aggccatcct gctcggcctg agatacaaaa agttgtacaa tcaggcgaga     780
gtcaaatatt ctctgtag                                                  798

<210> SEQ ID NO 8
<211> LENGTH: 265
<212> TYPE: PRT
<213> ORGANISM: Vesicular stomatitis virus
```

<400> SEQUENCE: 8

| | | | | | | | | | | | | | | |
|---|---|---|---|---|---|---|---|---|---|---|---|---|---|---|
|Met|Asp|Asn|Leu|Thr|Lys|Val|Arg|Glu|Tyr|Leu|Lys|Ser|Tyr|Ser|Arg|
|1| | | |5| | | | |10| | | | |15|

Leu Asp Gln Ala Val Gly Glu Ile Asp Glu Ile Glu Ala Gln Arg Ala
              20                  25                  30
Glu Lys Ser Asn Tyr Glu Leu Phe Gln Glu Asp Gly Val Glu Glu His
          35                  40                  45
Thr Lys Pro Ser Tyr Phe Gln Ala Ala Asp Asp Ser Asp Thr Glu Ser
     50                  55                  60
Glu Pro Glu Ile Glu Asp Asn Gln Gly Leu Tyr Ala Pro Asp Pro Glu
65                  70                  75                  80
Ala Glu Gln Val Glu Gly Phe Ile Gln Gly Pro Leu Asp Asp Tyr Ala
                 85                  90                  95
Asp Glu Glu Val Asp Val Val Phe Thr Ser Asp Trp Lys Gln Pro Glu
              100                 105                 110
Leu Glu Ser Asp Glu His Gly Lys Thr Leu Arg Leu Thr Leu Pro Glu
          115                 120                 125
Gly Leu Ser Gly Glu Gln Lys Ser Gln Trp Leu Ser Thr Ile Lys Ala
     130                 135                 140
Val Val Gln Ser Ala Lys Tyr Trp Asn Leu Ala Glu Cys Thr Phe Glu
145                 150                 155                 160
Ala Ser Gly Glu Gly Val Ile Met Lys Glu Arg Gln Ile Thr Pro Asp
                165                 170                 175
Val Tyr Lys Val Thr Pro Val Met Asn Thr His Pro Ser Gln Ser Glu
            180                 185                 190
Ala Val Ser Asp Val Trp Ser Leu Ser Lys Thr Ser Met Thr Phe Gln
        195                 200                 205
Pro Lys Lys Ala Ser Leu Gln Pro Leu Thr Ile Ser Leu Asp Glu Leu
    210                 215                 220
Phe Ser Ser Arg Gly Glu Phe Ile Ser Val Gly Gly Asp Gly Arg Met
225                 230                 235                 240
Ser His Lys Glu Ala Ile Leu Leu Gly Leu Arg Tyr Lys Lys Leu Tyr
                245                 250                 255
Asn Gln Ala Arg Val Lys Tyr Ser Leu
            260                 265

<210> SEQ ID NO 9
<211> LENGTH: 6330
<212> TYPE: DNA
<213> ORGANISM: Artificial sequence
<220> FEATURE:
<223> OTHER INFORMATION: Synthetic DNA encoding VSV-rp30  L protein

<400> SEQUENCE: 9

```
atggaagtcc acgattttga gaccgacgag ttcaatgatt tcaatgaaga tgactatgcc      60
acaagagaat tcctgaatcc cgatgagcgc atgacgtact tgaatcatgc tgattacaac     120
ctgaattctc ctctaattag tgatgatatt gacaatttaa tcaggaaatt caattctctt     180
ccaattccct cgatgtggga tagtaagaac tgggatggag ttcttgagat gttaacgtca     240
tgtcaagcca atcccatccc aacatctcag atgcataaat ggatgggaag ttggttaatg     300
tctgataatc atgatgccag tcaagggtat agtttttttac atgaagtgga caaagaggca     360
gaaataacat tgacgtggt ggagaccttc atccgcggct ggggcaacaa accaattgaa     420
tacatcaaaa aggaaagatg gactgactca ttcaaaattc tcgcttattt gtgtcaaaag     480
```

```
tttttggact tacacaagtt gacattaatc ttaaatgctg tctctgaggt ggaattgctc    540
aacttggcga ggactttcaa aggcaaagtc agaagaagtt ctcatggaac gaacatatgc    600
aggattaggg ttcccagctt gggtcctact tttatttcag aaggatgggc ttacttcaag    660
aaactttata ttctaatgga ccgaaacttt ctgttaatgg tcaaagatgt gattataggg    720
aggatgcaaa cggtgctatc catggtatgt agaatagaca acctgttctc agagcaagac    780
atcttctccc ttctaaatat ctacagaatt ggagataaaa ttgtggagag cagggaaat     840 ttttcttatg acttgattaa aatggtggaa ccgatatgca acttgaagct gatgaaatta    900
gcaagagaat caaggccttt agtcccacaa ttccctcatt ttgaaaatca tatcaagact    960
tctgttgatg aagggggcaaa aattgaccga ggtataagat tcctccatga tcagataatg   1020
agtgtgaaaa cagtggatct cacactggtg atttatggat cgttcagaca ttggggtcat   1080 cctttttatag attattacac tggactagaa aaattacatt cccaagtaac catgaagaaa   1140
gatattgatg tgtcatatgc aaaagcactt gcaagtgatt tagctcggat tgttctattt   1200
caacagttca atgatcataa aaagtggttc gtgaatggag acttgctccc tcatgatcat   1260
ccctttaaaa gtcatgttaa agaaaataca tggcccacag ctgctcaagt tcaagatttt   1320
ggagataaat ggcatgaact tccgctgatt aaatgttttg aaatacccga cttactagac   1380
ccatcgataa tatactctga caaaagtcat tcaatgaata ggtcagaggt gttgaaacat   1440
gtccgaatga atccgaacac tcctatccct agtaaaaagg tgttgcagac tatgttggac   1500
acaaaggcta ccaattggaa agaatttctt aaagagattg atgagaaggg cttagatgat   1560
gatgatctaa ttattggtct taaaggaaag gagagggaac tgaagttggc aggtagattt   1620
ttctccctaa tgtcttggaa attgcgagaa tactttgtaa ttaccgaata tttgataaag   1680
actcatttcg tccctatgtt taaaggcctg acaatggcgg acgatctaac tgcagtcatt   1740
aaaaagatgt tagattcctc atccggccaa ggattgaagt catatgaggc aatttgcata   1800
gccaatcaca ttgattacga aaaatggaat aaccaccaaa ggaagttatc aaacggccca   1860
gtgttccgag ttatgggcca gttcttaggt tatccatcct taatcgagag aactcatgaa   1920 tttttttgaga aaagtcttat atactacaat ggaagaccag acttgatgcg tgttcacaac   1980
aacacactga tcaattcaac ctcccaacga gtttgttggc aaggacaaga gggtggactg   2040
gaaggtctac ggcaaaaagg atggagtatc ctcaatctac tggttattca agagagggct   2100
aaaatcagaa acactgctgt caaagtcttg gcacaaggtg ataatcaagt tatttgcaca   2160
cagtataaaa cgaagaaatc gagaaacgtt gtagaattac agggtgctct caatcaaatg   2220
gtttctaata atgagaaaat tatgactgca atcaaaatag ggacagggaa gttaggactt   2280
ttgataaatg acgatgagac tatgcaatct gcagattact tgaattatgg aaaaataccg   2340
attttccgtg gagtgattag agggttagag accaagagat ggtcacgagt gacttgtgtc   2400
accaatgacc aaatacccac ttgtgctaat ataatgagct cagtttccac aaatgctctc   2460
accgtagctc attttgctga gaacccaatc aatgccatga tacagtacaa ttattttggg   2520
acatttgcta gactcttgtt gatgatgcat gatcctgctc ttcgtcaatc attgtatgaa   2580
gttcaagata agataccggg cttgcacagt tctactttca aatacgccat gttgtatttg   2640
gacccttcca ttggaggagt gtcgggcatg tcttttgtcca ggttttttgat tagagccttc   2700 ccagatcccg taacagaaag tctctcattc tggagattca tccatgtaca tgctcgaagt   2760
gagcatctga aggagatgag tgcagtattt ggaaacccccg atagccaa gtttcgaata    2820 actcacatag acaagctagt agaagatcca acctctctga acatcgctat gggaatgagt   2880
```

-continued

```
ccagcgaact tgttaaagac tgaggttaaa aaatgcttaa tcgaatcaag acaaaccatc    2940
aggaaccagg tgattaagga tgcaaccata tatttgtatc atgaagagga tcggctcaga    3000
agtttcttat ggtcaataaa tcctctgttc cctagatttt taagtgaatt caaatcaggc    3060
acttttttgg gagtcgcaga cgggctcatc agtctatttc aaaattctcg tactattcgg    3120
aactccttta agaaaaagta tcataggaa ttggatgatt tgattgtgag gagtgaggta    3180
tcctctttga cacatttagg gaaacttcat ttgagaaggg gatcatgtaa aatgtggaca    3240
tgttcagcta ctcatgctga cacattaaga tacaaatcct ggggccgtac agttattggg    3300
acaactgtac cccatccatt agaaatgttg ggtccacaac atcgaaaaga gactccttgt    3360
gcaccatgta acacatcagg gttcaattat gtttctgtgc attgtccaga cgggatccat    3420
gacgtcttta gttcacgggg accattgcct gcttatctag ggtctaaaac atctgaatct    3480
acatctattt tgcagccttg ggaaagggaa agcaaagtcc cactgattaa aagagctaca    3540
cgtcttagag atgctatctc ttggtttgtt gaacccgact ctaaactagc aatgactata    3600 cttctaaca tccactcttt aacaggcgaa gaatggacca aaaggcagca tgggttcaaa    3660
agaacagggt ctgcccttca taggttttcg acatctcgga tgagccatgg tgggttcgca    3720
tctcagagca ctgcagcatt gaccaggttg atggcaacta cagacaccat gagggatctg    3780
ggagatcaga atttcgactt tttattccaa gcaacgttgc tctatgctca aattaccacc    3840
actgttgcaa gagacggatg gatcaccagt tgtacagatc attatcatat gcctgtaag    3900 tcctgtttga gacccataga agagatcacc ctggactcaa gtatggacta cacgccccca    3960
gatgtatccc atgtgctgaa gacatggagg aatggggaag gttcgtgggg acaagagata    4020
aaacagatct atcctttaga agggaattgg aagaatttag cacctgctga gcaatcctat    4080
caagtcggca gatgtatagg tttctatat ggagacttgg cgtatagaaa atctactcat    4140
gccgaggaca gttctctatt tcctctatct atacaaggtc gtattagagg tcgaggtttc    4200 ttaaagggt tgctagacgg attaatgaga gcaagttgct gccaagtaat acaccggaga    4260
agtctggctc atttgaagag gccggccaac gcagtgtacg gaggtttgat ttacttgatt    4320
gataaattga gtgtatcacc tccattcctt tctcttacta gatcaggacc tattagagac    4380
gaattagaaa cgattcccca caagatccca acctcctatc cgacaagcaa ccgtgatatg    4440
ggggtgattg tcagaaatta cttcaaatac caatgccgtc taattgaaaa gggaaaatac    4500
agatcacatt attcacaatt atggttattc tcagatgtct tatccataga cttcattgga    4560
ccattctcta tttccaccac cctccttgcaa atcctataca agccatttt atctgggaaa    4620 gataagaatg agttgagaga gctggcaaat ctttcttcat tgctaagatc aggagagggg    4680
tgggaagaca tacatgtgaa attcttcacc aaggacatat tattgtgtcc agaggaaatc    4740
agacatgctt gcaagttcgg gattgctaag gataataata aagacatgag ctatcccct    4800 tggggaaggg aatccagagg gacaattaca acaatccctg tttattatac gaccaccct    4860 tacccaaaga tgctagagat gcctccaaga atccaaaatc ccctgctgtc cggaatcagg    4920
ttgggccaat taccaactgg cgctcattat aaaattcgga gtatattaca tggaatggga    4980
atccattaca gggacttctt gagttgtgga gacggctccg gagggatgac tgctgcatta    5040
ctacgagaaa atgtgcatag cagaggaata ttcaatagtc tgttagaatt atcagggtca    5100
gtcatgcgag gcgcctctcc tgagccccc agtgccctag aaactttagg aggagataaa    5160
tcgagatgtg taaatggtga acatgttggg gaatatccat ctgacttatg tgacccaagg    5220
acttgggact atttcctccg actcaaagca ggcttggggc ttcaaattga tttaattgta    5280
```

-continued

```
atggatatgg aagttcggga ttcttctact agcctgaaaa ttgagacgaa tgttagaaat    5340
tatgtgcacc ggattttgga tgagcaagga gttttaatct acaagactta tggaacatat    5400
atttgtgaga gcgaaaagaa tgcagtaaca atccttggtc ccatgttcaa gacggtcgac    5460
ttagttcaaa cagaatttag tagttctcaa acgtctgaag tatatatggt atgtaaaggt    5520
ttgaagaaat taatcgatga acccaatccc gattggtctt ccatcaatga atcctggaaa    5580
aacctgtacg cattccagtc atcagaacag gaatttgcca gagcaaagaa ggttagtaca    5640
tactttacct tgacaggtat tccctcccaa ttcattcctg atccttttgt aaacattgag    5700
actatgctac aaatattcgg agtacccacg ggtgtgtctc atgcggctgc cttaaaatca    5760
tctgatagac ctgcagattt attgaccatt agcctttttt atatggcgat tatatcgtat    5820
tataacatca atcatatcag agtaggaccg atacctccga acccccatc agatggaatt     5880 gcacaaaatg tggggatcgc tataactggt ataagctttt ggctgagttt gatggagaaa    5940
gacattccac tatatcaaca gtgtttagca gttatccagc aatcattccc gattaggtgg    6000
gaggctgttt cagtaaaagg aggatacaag cagaagtgga gtactagagg tgatgggctc    6060
ccaaaagata cccgaatttc agactccttg gccccaatcg ggaactggat cagatctctg    6120
gaattggtcc gaaaccaagt tcgtctaaat ccattcaatg agatcttgtt caatcagcta    6180
tgtcgtacag tggataatca tttgaaatgg tcaaatttgc gaagaaacac aggaatgatt    6240
gaatggatca atagacgaat ttcaaaagaa gaccggtcta tactgatgtt gaagagtgac    6300
ctacacgagg aaaactcttg gagagattaa                                     6330
```

<210> SEQ ID NO 10
<211> LENGTH: 2109
<212> TYPE: PRT
<213> ORGANISM: Vesicular stomatitis virus

<400> SEQUENCE: 10

```
Met Glu Val His Asp Phe Glu Thr Asp Glu Phe Asn Asp Phe Asn Glu
1               5                   10                  15

Asp Asp Tyr Ala Thr Arg Glu Phe Leu Asn Pro Asp Glu Arg Met Thr
            20                  25                  30

Tyr Leu Asn His Ala Asp Tyr Asn Leu Asn Ser Pro Leu Ile Ser Asp
        35                  40                  45

Asp Ile Asp Asn Leu Ile Arg Lys Phe Asn Ser Leu Pro Ile Pro Ser
    50                  55                  60

Met Trp Asp Ser Lys Asn Trp Asp Gly Val Leu Glu Met Leu Thr Ser
65                  70                  75                  80

Cys Gln Ala Asn Pro Ile Pro Thr Ser Gln Met His Lys Trp Met Gly
                85                  90                  95

Ser Trp Leu Met Ser Asp Asn His Asp Ala Ser Gln Gly Tyr Ser Phe
            100                 105                 110

Leu His Glu Val Asp Lys Glu Ala Glu Ile Thr Phe Asp Val Val Glu
        115                 120                 125

Thr Phe Ile Arg Gly Trp Gly Asn Lys Pro Ile Glu Tyr Ile Lys Lys
    130                 135                 140

Glu Arg Trp Thr Asp Ser Phe Lys Ile Leu Ala Tyr Leu Cys Gln Lys
145                 150                 155                 160

Phe Leu Asp Leu His Lys Leu Thr Leu Ile Leu Asn Ala Val Ser Glu
                165                 170                 175

Val Glu Leu Leu Asn Leu Ala Arg Thr Phe Lys Gly Lys Val Arg Arg
            180                 185                 190
```

```
Ser Ser His Gly Thr Asn Ile Cys Arg Ile Arg Val Pro Ser Leu Gly
        195                 200                 205
Pro Thr Phe Ile Ser Glu Gly Trp Ala Tyr Phe Lys Lys Leu Tyr Ile
    210                 215                 220
Leu Met Asp Arg Asn Phe Leu Leu Met Val Lys Asp Val Ile Ile Gly
225                 230                 235                 240
Arg Met Gln Thr Val Leu Ser Met Val Cys Arg Ile Asp Asn Leu Phe
                245                 250                 255
Ser Glu Gln Asp Ile Phe Ser Leu Leu Asn Ile Tyr Arg Ile Gly Asp
                260                 265                 270
Lys Ile Val Glu Arg Gln Gly Asn Phe Ser Tyr Asp Leu Ile Lys Met
            275                 280                 285
Val Glu Pro Ile Cys Asn Leu Lys Leu Met Lys Leu Ala Arg Glu Ser
    290                 295                 300
Arg Pro Leu Val Pro Gln Phe Pro His Phe Glu Asn His Ile Lys Thr
305                 310                 315                 320
Ser Val Asp Glu Gly Ala Lys Ile Asp Arg Gly Ile Arg Phe Leu His
                325                 330                 335
Asp Gln Ile Met Ser Val Lys Thr Val Asp Leu Thr Leu Val Ile Tyr
                340                 345                 350
Gly Ser Phe Arg His Trp Gly His Pro Phe Ile Asp Tyr Tyr Thr Gly
            355                 360                 365
Leu Glu Lys Leu His Ser Gln Val Thr Met Lys Lys Asp Ile Asp Val
    370                 375                 380
Ser Tyr Ala Lys Ala Leu Ala Ser Asp Leu Ala Arg Ile Val Leu Phe
385                 390                 395                 400
Gln Gln Phe Asn Asp His Lys Lys Trp Phe Val Asn Gly Asp Leu Leu
                405                 410                 415
Pro His Asp His Pro Phe Lys Ser His Val Lys Glu Asn Thr Trp Pro
            420                 425                 430
Thr Ala Ala Gln Val Gln Asp Phe Gly Asp Lys Trp His Glu Leu Pro
    435                 440                 445
Leu Ile Lys Cys Phe Glu Ile Pro Asp Leu Leu Asp Pro Ser Ile Ile
450                 455                 460
Tyr Ser Asp Lys Ser His Ser Met Asn Arg Ser Glu Val Leu Lys His
465                 470                 475                 480
Val Arg Met Asn Pro Asn Thr Pro Ile Pro Ser Lys Lys Val Leu Gln
                485                 490                 495
Thr Met Leu Asp Thr Lys Ala Thr Asn Trp Lys Glu Phe Leu Lys Glu
            500                 505                 510
Ile Asp Glu Lys Gly Leu Asp Asp Asp Leu Ile Ile Gly Leu Lys
    515                 520                 525
Gly Lys Glu Arg Glu Leu Lys Leu Ala Gly Arg Phe Phe Ser Leu Met
530                 535                 540
Ser Trp Lys Leu Arg Glu Tyr Phe Val Ile Thr Glu Tyr Leu Ile Lys
545                 550                 555                 560
Thr His Phe Val Pro Met Phe Lys Gly Leu Thr Met Ala Asp Asp Leu
                565                 570                 575
Thr Ala Val Ile Lys Lys Met Leu Asp Ser Ser Ser Gly Gln Gly Leu
            580                 585                 590
Lys Ser Tyr Glu Ala Ile Cys Ile Ala Asn His Ile Asp Tyr Glu Lys
    595                 600                 605
Trp Asn Asn His Gln Arg Lys Leu Ser Asn Gly Pro Val Phe Arg Val
610                 615                 620
```

```
Met Gly Gln Phe Leu Gly Tyr Pro Ser Leu Ile Glu Arg Thr His Glu
625                 630                 635                 640

Phe Phe Glu Lys Ser Leu Ile Tyr Tyr Asn Gly Arg Pro Asp Leu Met
                645                 650                 655

Arg Val His Asn Asn Thr Leu Ile Asn Ser Thr Ser Gln Arg Val Cys
            660                 665                 670

Trp Gln Gly Gln Glu Gly Gly Leu Gly Leu Arg Gln Lys Gly Trp
        675                 680                 685

Ser Ile Leu Asn Leu Leu Val Ile Gln Arg Glu Ala Lys Ile Arg Asn
    690                 695                 700

Thr Ala Val Lys Val Leu Ala Gln Gly Asp Asn Gln Val Ile Cys Thr
705                 710                 715                 720

Gln Tyr Lys Thr Lys Lys Ser Arg Asn Val Val Glu Leu Gln Gly Ala
                725                 730                 735

Leu Asn Gln Met Val Ser Asn Asn Glu Lys Ile Met Thr Ala Ile Lys
            740                 745                 750

Ile Gly Thr Gly Lys Leu Gly Leu Leu Ile Asn Asp Asp Glu Thr Met
        755                 760                 765

Gln Ser Ala Asp Tyr Leu Asn Tyr Gly Lys Ile Pro Ile Phe Arg Gly
770                 775                 780

Val Ile Arg Gly Leu Glu Thr Lys Arg Trp Ser Arg Val Thr Cys Val
785                 790                 795                 800

Thr Asn Asp Gln Ile Pro Thr Cys Ala Asn Ile Met Ser Ser Val Ser
                805                 810                 815

Thr Asn Ala Leu Thr Val Ala His Phe Ala Glu Asn Pro Ile Asn Ala
            820                 825                 830

Met Ile Gln Tyr Asn Tyr Phe Gly Thr Phe Ala Arg Leu Leu Met
        835                 840                 845

Met His Asp Pro Ala Leu Arg Gln Ser Leu Tyr Glu Val Gln Asp Lys
850                 855                 860

Ile Pro Gly Leu His Ser Ser Thr Phe Lys Tyr Ala Met Leu Tyr Leu
865                 870                 875                 880

Asp Pro Ser Ile Gly Gly Val Ser Gly Met Ser Leu Ser Arg Phe Leu
                885                 890                 895

Ile Arg Ala Phe Pro Asp Pro Val Thr Glu Ser Leu Ser Phe Trp Arg
            900                 905                 910

Phe Ile His Val His Ala Arg Ser Glu His Leu Lys Glu Met Ser Ala
        915                 920                 925

Val Phe Gly Asn Pro Glu Ile Ala Lys Phe Arg Ile Thr His Ile Asp
930                 935                 940

Lys Leu Val Glu Asp Pro Thr Ser Leu Asn Ile Ala Met Gly Met Ser
945                 950                 955                 960

Pro Ala Asn Leu Leu Lys Thr Glu Val Lys Lys Cys Leu Ile Glu Ser
                965                 970                 975

Arg Gln Thr Ile Arg Asn Gln Val Ile Lys Asp Ala Thr Ile Tyr Leu
            980                 985                 990

Tyr His Glu Glu Asp Arg Leu Arg  Ser Phe Leu Trp Ser  Ile Asn Pro
        995                 1000                1005

Leu Phe  Pro Arg Phe Leu Ser  Glu Phe Lys Ser Gly  Thr Phe Leu
    1010                1015                1020

Gly Val  Ala Asp Gly Leu Ile  Ser Leu Phe Gln Asn  Ser Arg Thr
    1025                1030                1035

Ile Arg  Asn Ser Phe Lys Lys  Lys Tyr His Arg Glu  Leu Asp Asp
```

```
            1040                1045                1050

Leu Ile Val Arg Ser Glu Val Ser Ser Leu Thr His Leu Gly Lys
    1055                1060                1065

Leu His Leu Arg Arg Gly Ser Cys Lys Met Trp Thr Cys Ser Ala
    1070                1075                1080

Thr His Ala Asp Thr Leu Arg Tyr Lys Ser Trp Gly Arg Thr Val
    1085                1090                1095

Ile Gly Thr Thr Val Pro His Pro Leu Glu Met Leu Gly Pro Gln
    1100                1105                1110

His Arg Lys Glu Thr Pro Cys Ala Pro Cys Asn Thr Ser Gly Phe
    1115                1120                1125

Asn Tyr Val Ser Val His Cys Pro Asp Gly Ile His Asp Val Phe
    1130                1135                1140

Ser Ser Arg Gly Pro Leu Pro Ala Tyr Leu Gly Ser Lys Thr Ser
    1145                1150                1155

Glu Ser Thr Ser Ile Leu Gln Pro Trp Glu Arg Glu Ser Lys Val
    1160                1165                1170

Pro Leu Ile Lys Arg Ala Thr Arg Leu Arg Asp Ala Ile Ser Trp
    1175                1180                1185

Phe Val Glu Pro Asp Ser Lys Leu Ala Met Thr Ile Leu Ser Asn
    1190                1195                1200

Ile His Ser Leu Thr Gly Glu Glu Trp Thr Lys Arg Gln His Gly
    1205                1210                1215

Phe Lys Arg Thr Gly Ser Ala Leu His Arg Phe Ser Thr Ser Arg
    1220                1225                1230

Met Ser His Gly Gly Phe Ala Ser Gln Ser Thr Ala Ala Leu Thr
    1235                1240                1245

Arg Leu Met Ala Thr Thr Asp Thr Met Arg Asp Leu Gly Asp Gln
    1250                1255                1260

Asn Phe Asp Phe Leu Phe Gln Ala Thr Leu Leu Tyr Ala Gln Ile
    1265                1270                1275

Thr Thr Thr Val Ala Arg Asp Gly Trp Ile Thr Ser Cys Thr Asp
    1280                1285                1290

His Tyr His Ile Ala Cys Lys Ser Cys Leu Arg Pro Ile Glu Glu
    1295                1300                1305

Ile Thr Leu Asp Ser Ser Met Asp Tyr Thr Pro Pro Asp Val Ser
    1310                1315                1320

His Val Leu Lys Thr Trp Arg Asn Gly Glu Gly Ser Trp Gly Gln
    1325                1330                1335

Glu Ile Lys Gln Ile Tyr Pro Leu Glu Gly Asn Trp Lys Asn Leu
    1340                1345                1350

Ala Pro Ala Glu Gln Ser Tyr Gln Val Gly Arg Cys Ile Gly Phe
    1355                1360                1365

Leu Tyr Gly Asp Leu Ala Tyr Arg Lys Ser Thr His Ala Glu Asp
    1370                1375                1380

Ser Ser Leu Phe Pro Leu Ser Ile Gln Gly Arg Ile Arg Gly Arg
    1385                1390                1395

Gly Phe Leu Lys Gly Leu Leu Asp Gly Leu Met Arg Ala Ser Cys
    1400                1405                1410

Cys Gln Val Ile His Arg Arg Ser Leu Ala His Leu Lys Arg Pro
    1415                1420                1425

Ala Asn Ala Val Tyr Gly Gly Leu Ile Tyr Leu Ile Asp Lys Leu
    1430                1435                1440
```

-continued

```
Ser Val Ser Pro Pro Phe Leu Ser Leu Thr Arg Ser Gly Pro Ile
    1445            1450               1455

Arg Asp Glu Leu Glu Thr Ile Pro His Lys Ile Pro Thr Ser Tyr
    1460            1465               1470

Pro Thr Ser Asn Arg Asp Met Gly Val Ile Val Arg Asn Tyr Phe
    1475            1480               1485

Lys Tyr Gln Cys Arg Leu Ile Glu Lys Gly Lys Tyr Arg Ser His
    1490            1495               1500

Tyr Ser Gln Leu Trp Leu Phe Ser Asp Val Leu Ser Ile Asp Phe
    1505            1510               1515

Ile Gly Pro Phe Ser Ile Ser Thr Thr Leu Leu Gln Ile Leu Tyr
    1520            1525               1530

Lys Pro Phe Leu Ser Gly Lys Asp Lys Asn Glu Leu Arg Glu Leu
    1535            1540               1545

Ala Asn Leu Ser Ser Leu Leu Arg Ser Gly Glu Gly Trp Glu Asp
    1550            1555               1560

Ile His Val Lys Phe Phe Thr Lys Asp Ile Leu Leu Cys Pro Glu
    1565            1570               1575

Glu Ile Arg His Ala Cys Lys Phe Gly Ile Ala Lys Asp Asn Asn
    1580            1585               1590

Lys Asp Met Ser Tyr Pro Pro Trp Gly Arg Glu Ser Arg Gly Thr
    1595            1600               1605

Ile Thr Thr Ile Pro Val Tyr Tyr Thr Thr Pro Tyr Pro Lys
    1610            1615               1620

Met Leu Glu Met Pro Pro Arg Ile Gln Asn Pro Leu Leu Ser Gly
    1625            1630               1635

Ile Arg Leu Gly Gln Leu Pro Thr Gly Ala His Tyr Lys Ile Arg
    1640            1645               1650

Ser Ile Leu His Gly Met Gly Ile His Tyr Arg Asp Phe Leu Ser
    1655            1660               1665

Cys Gly Asp Gly Ser Gly Gly Met Thr Ala Ala Leu Leu Arg Glu
    1670            1675               1680

Asn Val His Ser Arg Gly Ile Phe Asn Ser Leu Leu Glu Leu Ser
    1685            1690               1695

Gly Ser Val Met Arg Gly Ala Ser Pro Glu Pro Ser Ala Leu
    1700            1705               1710

Glu Thr Leu Gly Gly Asp Lys Ser Arg Cys Val Asn Gly Glu Thr
    1715            1720               1725

Cys Trp Glu Tyr Pro Ser Asp Leu Cys Asp Pro Arg Thr Trp Asp
    1730            1735               1740

Tyr Phe Leu Arg Leu Lys Ala Gly Leu Gly Leu Gln Ile Asp Leu
    1745            1750               1755

Ile Val Met Asp Met Glu Val Arg Asp Ser Ser Thr Ser Leu Lys
    1760            1765               1770

Ile Glu Thr Asn Val Arg Asn Tyr Val His Arg Ile Leu Asp Glu
    1775            1780               1785

Gln Gly Val Leu Ile Tyr Lys Thr Tyr Gly Thr Tyr Ile Cys Glu
    1790            1795               1800

Ser Glu Lys Asn Ala Val Thr Ile Leu Gly Pro Met Phe Lys Thr
    1805            1810               1815

Val Asp Leu Val Gln Thr Glu Phe Ser Ser Ser Gln Thr Ser Glu
    1820            1825               1830

Val Tyr Met Val Cys Lys Gly Leu Lys Lys Leu Ile Asp Glu Pro
    1835            1840               1845
```

Asn Pro Asp Trp Ser Ser Ile Asn Glu Ser Trp Lys Asn Leu Tyr
        1850                1855                1860

Ala Phe Gln Ser Ser Glu Gln Glu Phe Ala Arg Ala Lys Lys Val
    1865                1870                1875

Ser Thr Tyr Phe Thr Leu Thr Gly Ile Pro Ser Gln Phe Ile Pro
    1880                1885                1890

Asp Pro Phe Val Asn Ile Glu Thr Met Leu Gln Ile Phe Gly Val
    1895                1900                1905

Pro Thr Gly Val Ser His Ala Ala Leu Lys Ser Ser Asp Arg
    1910                1915                1920

Pro Ala Asp Leu Leu Thr Ile Ser Leu Phe Tyr Met Ala Ile Ile
    1925                1930                1935

Ser Tyr Tyr Asn Ile Asn His Ile Arg Val Gly Pro Ile Pro Pro
    1940                1945                1950

Asn Pro Pro Ser Asp Gly Ile Ala Gln Asn Val Gly Ile Ala Ile
    1955                1960                1965

Thr Gly Ile Ser Phe Trp Leu Ser Leu Met Glu Lys Asp Ile Pro
    1970                1975                1980

Leu Tyr Gln Gln Cys Leu Ala Val Ile Gln Gln Ser Phe Pro Ile
    1985                1990                1995

Arg Trp Glu Ala Val Ser Val Lys Gly Gly Tyr Lys Gln Lys Trp
    2000                2005                2010

Ser Thr Arg Gly Asp Gly Leu Pro Lys Asp Thr Arg Ile Ser Asp
    2015                2020                2025

Ser Leu Ala Pro Ile Gly Asn Trp Ile Arg Ser Leu Glu Leu Val
    2030                2035                2040

Arg Asn Gln Val Arg Leu Asn Pro Phe Asn Glu Ile Leu Phe Asn
    2045                2050                2055

Gln Leu Cys Arg Thr Val Asp His Leu Lys Trp Ser Asn Leu
    2060                2065                2070

Arg Arg Asn Thr Gly Met Ile Glu Trp Ile Asn Arg Arg Ile Ser
    2075                2080                2085

Lys Glu Asp Arg Ser Ile Leu Met Leu Lys Ser Asp Leu His Glu
    2090                2095                2100

Glu Asn Ser Trp Arg Asp
    2105

<210> SEQ ID NO 11
<211> LENGTH: 26
<212> TYPE: DNA
<213> ORGANISM: Artificial Sequence
<220> FEATURE:
<223> OTHER INFORMATION: Synthetic RT-Oligonucleotide

<400> SEQUENCE: 11
acgaagacaa acaaaccatt attatc                                          26

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
gatatggtga gaggctgaag ac                                              22

```
<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
ccagtgatga acacacatcc                                                 20

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
agtctcgagc gtgatatctg ttag                                            24

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
ctcaaatcct gctaggtatg                                                 20

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
gacttccatg attgctgtta g                                               21

<210> SEQ ID NO 17
<211> LENGTH: 29
<212> TYPE: DNA
<213> ORGANISM: Artificial Sequence
<220> FEATURE:
<223> OTHER INFORMATION: Synthetic primer

<400> SEQUENCE: 17
ttcaaggacg acgacggcaa ctacaagac                                       29

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
accctcttgt ccttgccaac                                                 20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
```
cttaatcgag agaactcatg                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
gatctgtttt atctcttgtc                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
gactcaagta tggactacac                                               20

<210> SEQ ID NO 22
<211> LENGTH: 19
<212> TYPE: DNA
<213> ORGANISM: Artificial Sequence
<220> FEATURE:
<223> OTHER INFORMATION: Synthetic primer

<400> SEQUENCE: 22
acgaagacca caaaaccag                                                19

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
aaaaccctgc cttccacttc                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
caaacctgct gtagtaagag                                               20

<210> SEQ ID NO 25
<211> LENGTH: 22
<212> TYPE: DNA
<213> ORGANISM: Artificial Sequence
<220> FEATURE:
<223> OTHER INFORMATION: Synthetic primer

<400> SEQUENCE: 25
ctagtctaac ttctagcttc tg                                            22

<210> SEQ ID NO 26
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 26
ttcaggacgt tgagaggatc                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
aacagatcga tctctgttag                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
ggagcaagat agctgagatc                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
ttccatccga tccttcactc                                               20

<210> SEQ ID NO 30
<211> LENGTH: 21
<212> TYPE: DNA
<213> ORGANISM: Artificial Sequence
<220> FEATURE:
<223> OTHER INFORMATION: Synthetic primer

<400> SEQUENCE: 30
attcaagacg ctgcttcgca a                                             21

<210> SEQ ID NO 31
<211> LENGTH: 21
<212> TYPE: DNA
<213> ORGANISM: Artificial Sequence
<220> FEATURE:
<223> OTHER INFORMATION: Synthetic primer

<400> SEQUENCE: 31
gagcttttcc aactactgaa c                                             21

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
gtgataccat gctcaaagag                                               20
```

```
<210> SEQ ID NO 33
<211> LENGTH: 19
<212> TYPE: DNA
<213> ORGANISM: Artificial Sequence
<220> FEATURE:
<223> OTHER INFORMATION: Synthetic primer

<400> SEQUENCE: 33
cctttagtcc cacaattcc                                                    19

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
gatccactgt tttcacactc                                                   20

<210> SEQ ID NO 35
<211> LENGTH: 21
<212> TYPE: DNA
<213> ORGANISM: Artificial Sequence
<220> FEATURE:
<223> OTHER INFORMATION: Synthetic primer

<400> SEQUENCE: 35
cgaacttgtt aaagactgag g                                                 21

<210> SEQ ID NO 36
<211> LENGTH: 20
<212> TYPE: DNA
<213> ORGANISM: Artificial Sequence
<220> FEATURE:
<223> OTHER INFORMATION: Synthetic primer

<400> SEQUENCE: 36
ggaacagagg atttattgac                                                   20

<210> SEQ ID NO 37
<211> LENGTH: 21
<212> TYPE: DNA
<213> ORGANISM: Artificial Sequence
<220> FEATURE:
<223> OTHER INFORMATION: Synthetic primer

<400> SEQUENCE: 37
gaatcaggtt gggccaatta c                                                 21

<210> SEQ ID NO 38
<211> LENGTH: 20
<212> TYPE: DNA
<213> ORGANISM: Artificial Sequence
<220> FEATURE:
<223> OTHER INFORMATION: Synthetic primer

<400> SEQUENCE: 38
agccgtctcc acaactcaag                                                   20

<210> SEQ ID NO 39
<211> LENGTH: 20
<212> TYPE: DNA
<213> ORGANISM: Artificial Sequence
<220> FEATURE:
<223> OTHER INFORMATION: Synthetic primer

<400> SEQUENCE: 39
```

```
cacttctgct tgtatcctcc                                           20

<210> SEQ ID NO 40
<211> LENGTH: 21
<212> TYPE: DNA
<213> ORGANISM: Artificial Sequence
<220> FEATURE:
<223> OTHER INFORMATION: Synthetic primer

<400> SEQUENCE: 40
gagcgcacca tcttcttcaa g                                         21

<210> SEQ ID NO 41
<211> LENGTH: 19
<212> TYPE: DNA
<213> ORGANISM: Artificial Sequence
<220> FEATURE:
<223> OTHER INFORMATION: Synthetic primer

<400> SEQUENCE: 41
tgtcgccctc gaacttcag                                            19
```

COMPOSITIONS AND METHODS OF USE OF AN ONCOLYTIC VESICULAR STOMATITIS VIRUS

CROSS REFERENCE TO RELATED APPLICATIONS

This application claims priority to and benefit of U.S. Provisional Patent Application No. 61/143,236 filed on Jan. 8, 2009, and where permissible is incorporated by reference in its entirety.

GOVERNMENT SUPPORT

The United States government has certain rights in this invention by virtue of National Institutes of Health Grant Numbers 5RO1CA124737-03 and 5RO1AI048854-09 to Anthony N. van den Pol.

FIELD OF THE INVENTION

The present application is generally related to oncolytic vesicular stomatitis viruses and compositions and methods of use for treatment of cancer.

BACKGROUND OF THE INVENTION

There are many different types of cancers and means of treating the cancers. The most typical way of treating cancer is through the use of chemotherapeutic agents that selectively target the more rapidly proliferating tumor cells relative to the host cells. These have serious side effects, including death of normal cells, mucositis, nausea, and may give rise to drug resistant tumor cells. Antibodies and antibody targeted therapeutics are a desirable alternative to chemotherapeutics since they are more selective, but are limited to the few tumors expressing antigens that can be effectively targeted. Drugs that inhibit angiogenesis are another approach having fewer side effects, but have been found to only limit tumor growth, not kill existing tumors.

Viruses are an alternative approach for combating cancer. One approach to treating tumors is to use replication-incompetent viral vectors to deliver genes to the tumor. Replication-incompetent viruses have value in delivering genes to the area of the tumor that might then alter the general environment near the tumor, making it less hospitable to the tumor. There are a number of interesting strategies based on viral vectors, including delivery of suicide genes such as HSV-tk or ricin, genes that reduce vascular proliferation, restore cell cycle control and encourage apoptosis such as p53, or stimulate an immune response (IL-12, interferon, tumor necrosis factor). One problem with replication incompetent viruses is that, even with direct injection into a tumor, the number of cells infected in a solid tumor is generally quite small, averaging about 7% of the total tumor cell population (Puumalainen ei al., *Adv Exp Med Biol,* 451:505-509 (1998); Rainov and Ren, *Acta Neurochir Suppl,* 88:113-123 (2003)). Thus with viruses that do not replicate, it has not been possible to infect a substantial percentage of the tumor cells.

A primary advantage of conditional replication competent viruses is that they infect and kill tumor cells, and then their new viral progeny are released to kill additional tumor cells. In contrast to replication incompetent viral vectors that only infect a small number of tumor cells, a small injection of replication competent VSV or Sindbis virus can lead to a rapid and complete intratumoral spread of the virus. Beneficially, due to local self-amplification, replication competent viruses may be effective with one single application, whereas repetitive injections have to be applied for the less effective replication incompetent agents. A number of viruses have been shown to have oncolytic potential, including recombinant herpes, adeno, polio and alpha viruses. Myxoma virus was effective in killing medulloblastoma, and infection was increased in combination with Rapamycin (Lun, et al., *Cancer Res.,* 67(18):8818-8827 (2007). Herpes simplex virus has been rendered conditionally replication-competent for tumors by inserting mutations in several HSV genes. Oncolytic adenovirus agents specifically restrict their replication to p53 deficient tumor cells, and retrovirus to tumors with activated Ras-signaling pathways (Chiocca, *Nat. Rev. Cancer,* 2: 938-950 (2002); Rainov and Ren, *Acta Neurochir Suppl,* 88:113-123 (2003)). These strategies are restricted to defined mutations of the tumor. Oncolytic viruses that are not strictly dependent on a single gene mutation are therefore desirable to treat cancers that exhibit a heterogenous array of genetic aberrations.

One replication competent virus with oncolytic potential is vesicular stomatitis virus (VSV) (Lun, et al. *J. Nat. Can. Instit.,* 98(21): 1546-1557 (2006), Wu, et al., *Clin. Cancer Res.,* 14(4):1218-1227 (2008), Ozduman, et al., *J. Virol.,* 83(22):11540-11549 (2009), Wollmann, et al., *J. Virol,* (2009 Epub; 2010 J. Virology 84(3). VSV is an RNA virus that uses a negative strand RNA to encode its genome. Although some viruses may express over a hundred different genes, VSV with its 11-12 kilobase genome encodes five structural genes, N, P, M, G, and L, encoding proteins that each may have multiple functions. The virus envelope consists of a host cell-derived lipid bilayer that contains several hundred copies of viral glycoprotein spikes (G-protein) and forms a characteristic bullet shape. The nucleocapsid protein N forms a tight complex with the helical coiled non-segmented RNA genome and the viral matrix protein M bridges the gap between nucleocapsid and viral envelope. A complex formed by the phosphoprotein P and the large polymerase L facilitates viral polymerase activity. Phosphorylation is thought to play a role in the function of the of P protein, for example, unphosphorylated P is much less active in supporting viral transcription at low concentrations (Spadafora et al., *J. Virol.,* 70(7): 45-38-4548 (1996)).

VSV binds to the cell membrane, becomes internalized, and then replicates in the cell cytoplasm. VSV replicates fairly quickly, about 6 hours for progeny virus to bud from the plasma membrane of the infected cell. A single infected cell can release many VSV progeny, although some of the progeny are defective particles. VSV blocks the ability of infected cells to transport mRNA out of the nucleus (VSV M-protein blocks nuclear pores), and usurps the host cell translational mechanisms to synthesize primarily viral gene products. VSV is found around the world. Many mammals, including humans, can be infected by the virus which is probably spread by biting flies (de Mattos et al. In Fields of Virology, pp. 1245-1277, (Knipe, et al., Eds) (2001)). Humans show only modest symptoms, or none, with infection which clears as the immune system eliminates the virus. In some rural regions of central America, the majority of adults show seropositivity with antisera against VSV with few symptoms detectable (Tesh, et al., *Am. J. Epidemiol.,* 90:255-261, (1969)). Replication competent VSVs are in human clinical trials as a carrier virus to generate immune responses against more dangerous viruses, including HIV, influenza, and papilloma viruses cloned into the VSV genome (Roberts, et al., *J. Virol.,* 73:3723-32 (1999); Roberts, et al., *J. Virol.,* 78: 3196-3199 (2004); Okuma et al., J. Virol. 346(1):86-97 (2006); Rose et al., Cell, 106:539-549 (2001)).

VSV has demonstrated potential as an oncolytic virus. In a battery of in vitro and in vivo tests, VSV showed the greatest promise among nine replication competent viruses including Sindbis, human and mouse cytomegalovirus, pseudorabies virus, the parvoviruses MVMi and MVMp, and others that have been described as having oncolytic potential (Wollmann et al, *J. Virol.*, 79(10): 6005-6022 (2005)). Normal cells possess innate mechanisms to reduce or block viral infections. VSV replication can be attenuated or blocked by cellular interferon (IFN). Defects in this system are thought to contribute to the oncolytic activity of VSV (Wollmann, et al., *J. Virol.*, 81(3):1479-1491 (2007)). In addition to destroying glioblastoma cells, VSV has also shown promise outside the brain as an anti-cancer agent in recent experimental studies on various solid tumors, for example carcinoma of colon (Stojdl et al., *Cancer Cell*, 4:263-275 (2003)), breast (Ebert et al., *Cancer Gene Ther*, 12:350-358 (2005)), prostate (Ahmed et al., *Virology*, 330:34-49 (2004)) and liver (Shinozaki et al, 2005) or hematological malignancies such as leukemia (Lichty et al., 2004b).

To further enhance the potential selectivity of VSVs for brain cancer cells, a recombinant wildtype-based VSV expressing a gene coding for green fluorescent protein (GFP), VSV-G/GFP (7,30), was grown for many generations on human glioblastoma cancer cells using a protocol that enhanced viral fitness based on viral internalization, replication, and cell selectivity. This cell-adapted propagation resulted in a virus that displayed an enhanced rate of infection and replication on the U-87MG glioblastoma line used to grow the virus and was named VSV-rp30 (Wollmann et al, *J. Virol.*, 79(10): 6005-6022 (2005), Ozduman, et al., *J. of Neurosci.*, 28(8): 1882-1893 (2008)). Identification of the differences between VSV-rp30 and less effective VSV viruses, such as the parent strain, would provide an avenue for development of a range of oncolytic viruses with improved oncolytic potential for anti-cancer therapeutics.

It is an object of the invention to provide isolated oncolytic VSV virus with enhanced oncolytic potential, compared to naturally occurring wild strains.

It is a further object of the invention to provide mutant VSVs with an increased replicative capacity in cancer cells relative to normal cells.

It is another object of the invention to provide a viral composition effective to reduce tumor burden.

It is another object of the invention to provide methods for making and using the viral compositions for treating cancer.

SUMMARY OF THE INVENTION

Oncolytic VSV viruses have been developed as a strategy for combating cancer, where the virus selectively infect, and kill, tumor cells. Mutant VSV that have one or more mutations in the nucleic acid sequence encoding the viral genome, specifically, mutations in the P and/or L proteins enhance the oncolytic potential, of the virus. Some viruses have more than one mutation. For example, a virus can have mutations of both the L and P proteins. An exemplary virus is VSV-rp30. In some embodiments, viruses are modified to include one or more targeting or therapeutic proteins. In other embodiments viral genes are substituted or rearranged to modulate infectivity and replication frequency of the virus.

Pharmaceutical compositions containing virus and one or more excipients may be systemically or locally administered. For example, compositions are administered for the treatment of benign or malignant tumors. In a preferred embodiment, administration of the virus reduces one or more symptoms of a tumor. Preferred routes of administration include intratumoral, intravenous, and intraarterial injection, and intranasal delivery.

Administration of the disclosed compositions containing oncolytic viruses may be coupled with surgical, radiologic, other therapeutic approaches to treatment of cancer. For example, co-administration of virus with an immunosuppressant will preferentially reduce or inhibit the subject's immune response, extending the infective half-life of the virus. Compositions containing virus can also be co-administered with traditional cancer treatments such as chemotherapy.

Methods of manufacturing virus are disclosed. Additional mutant VSV viruses exhibiting desired properties can be developed by applying selective pressure, or through directed or random mutagenesis.

BRIEF DESCRIPTION OF THE DRAWINGS

FIG. 2 is a schematic comparing VSV genomes, as indicated. The five viral genes are labeled, N, P, M, G and L. Additional genes including Green Fluorescent Protein (GFP) and G/GFP fusion are also indicated. Mutations are identified with an arrow head. S126L indicates a serine to leucine substitution as codon 126 of the P protein, and D223Y indicates an aspartic acid to tyrosine substitution at codon 223 of the L protein of VSV-rp30. M51 indicates a deletion of the methionine at position 51 of the M protein, and CT9 indicates deletion of all but 9 of the 27 amino acids of the C-terminal cytoplasmic tail in VSV-M51/CT9.

FIGS. 7A, 7B and 7C are a schematized general outline of VSV oncolysis in the SCID mouse brain tumor model. After intravenous injection (7A), VSV-rp30 infection starts at few scattered foci (7B) around the brain tumor vasculature and spreads to infect the entire tumor (7C).

FIG. 8 is a bar graph illustrating tumor area (%) as a function of time post-infection. Tumor infectivity (% of tumor GFP-positive) is represented by vertical bars from the bottom up: left hand bar (diagonal hatching) represents the parent virus VSV-G/GFP and the right hand bar (open) represents the mutant virus VSV-rp30 for each time point (24, 48, 72 hours, left to right). Intact tumor (%) infected with each virus is represented by vertical bars from the top down (stippled). The space (vertical hatching) between each top and bottom bar represents tumor debris (%)

DETAILED DESCRIPTION OF THE INVENTION

I. Definitions

Figure 1A:
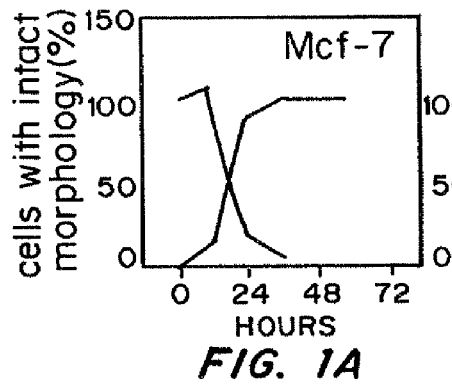
FIGS. 1A, 1B, 1C, 1D, and 1E are graphs illustrating VSV-rp30 oncolysis of five tumor cell lines: (1A) Mcf-7 human breast cancer cells, (1B) T47-D human breast cancer cells, (1C) BT-474 human breast cancer cells, (1D) A-549 human lung cancer cells, and (1E) Calu-1 human lung cancer cells. Each graph illustrates the % infected cells (line rising from bottom left to top right), and cells with intact morphology (line falling from top left to bottom right), as a function of time (hours).
Figure 1B:
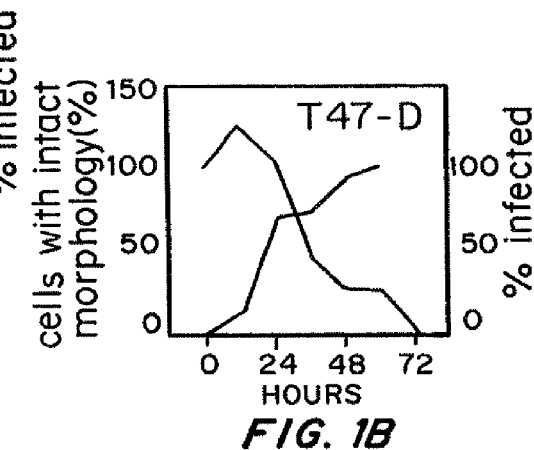
Figure 1C:
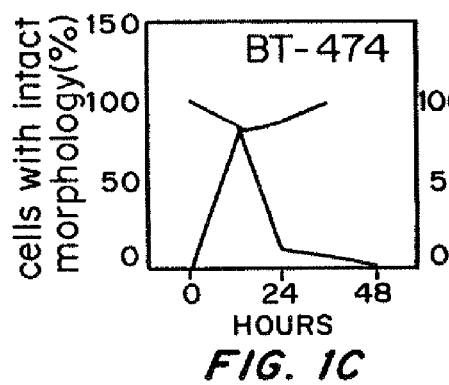
Figure 1D:
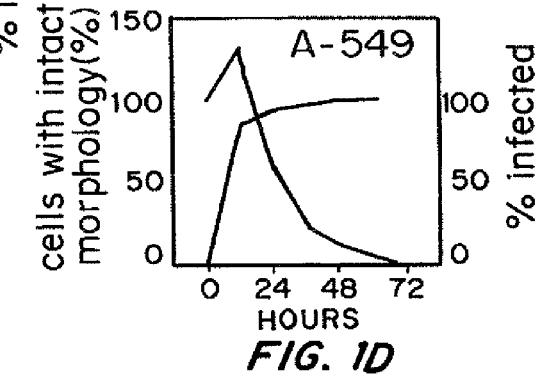
Figure 1E:
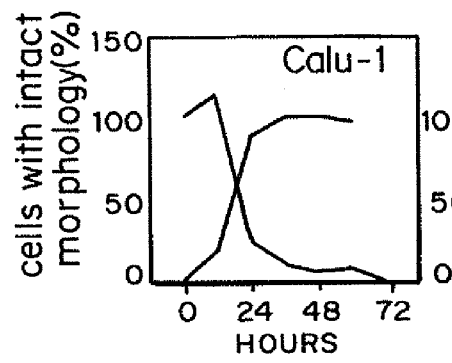

As used herein the term "isolated" is meant to describe a compound of interest (e.g., either a polynucleotide or a polypeptide) that is in an environment different from that in which the compound naturally occurs e.g. separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. With respect to nucleic acids, the term "isolated" includes any non-naturally-occurring nucleic acid sequence, since such non-naturally-occurring sequences are not found in nature and do not have immediately contiguous sequences in a naturally-occurring genome.

As used herein, the term "nucleic acid(s)" refers to any nucleic acid containing molecule, including, but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. In accordance with standard nomenclature, nucleic acid sequences are denominated by either a three letter, or single letter code as indicated as follows: adenine (Ade, A), thymine (Thy, T), guanine (Gua, G) cytosine (Cyt, C), uracil (Ura, U).

As used herein, the term "polynucleotide" refers to a chain of nucleotides of any length, regardless of modification (e.g., methylation).

The term "gene" refers to a nucleic acid (e.g., DNA or RNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion thereof. The term also encompasses the coding region of a structural gene and the sequences located adjacent to the coding region on both the 5' and 3' ends for a distance of about 1 kb on either end such that the gene corresponds to the length of the full-length mRNA. The term "gene" encompasses both cDNA and genomic forms of a gene, which may be made of DNA, or RNA. A genomic form or clone of a gene may contain the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "nucleic acid molecule encoding," refers to the order or sequence of nucleotides along a strand of nucleotides. The order of these nucleotides determines the order of amino acids along the polypeptide (protein) chain. The nucleotide sequence thus codes for the amino acid sequence As used herein, the term "polypeptide" refers to a chain of amino acids of any length, regardless of modification (e.g., phosphorylation or glycosylation). In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, a "variant," "mutant," or "mutated" polynucleotide contains at least one polynucleotide sequence alteration as compared to the polynucleotide sequence of the corresponding wild-type or parent polynucleotide. A "variant," "mutant," or "mutated" polypeptide contains at least one amino acid sequence alteration as compared to the amino acid sequence of the corresponding wild-type, or parent polypeptide. Mutations may be natural, deliberate, or accidental.

As used herein, a "nucleic acid sequence alteration" can be, for example, a substitution, a deletion, or an insertion of one or more nucleotides. An "amino acid sequence alteration" can be, for example, a substitution, a deletion, or an insertion of one or more amino acids.

As used herein, a "vector" is a replicon, such as a plasmid, phage, or cosmid, into which another DNA segment may be inserted so as to bring about the replication of the inserted segment. The vectors described herein can be expression vectors.

As used herein, the term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease, and the treatment being effected.

As used herein, the terms "neoplastic cells," "neoplasia," "tumor," "tumor cells," "cancer" and "cancer cells," (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign.

As used herein, the terms "VSV-rp30" and "VSV-rp30a" are used interchangeably, and refer to a mutant VSV with improved oncolytic potential compared to the parent strain VSV-G/GFP.

II. Compositions

A. Viruses

The viruses disclosed herein may be "native" or naturally-occurring viruses, or engineered viruses, such as recombinant viruses. Mutations are introduced into the viral genome to provide viruses with enhanced selectivity and cytolytic activity for cells of interest, such as cancer cells.

1. Oncolytic Viruses

The present invention includes mutant VSV that have one or more mutations in the nucleic acid sequence encoding the viral genome. The mutations may reduce or inhibit post translational phosphorylation of viral proteins, or may work well due to other independent mechanisms. Changes in post translational phosphorylation of viral proteins, such as the P and/or L proteins, may increase the specificity or infectivity of oncolytic viruses. Increasing the specificity or infectivity of a virus for one or more types of cancers compared to normal cells increases the oncolytic potential of the virus.

A protein kinase is an enzyme that modifies proteins by covalently adding phosphate groups to them in a chemical reaction known as phosphorylation. Phosphorylation can cause a functional change of the phosphorylated protein, such changing enzyme activity, cellular location, or association with other proteins. The amino acids serine, threonine, and tyrosine, and sometimes others such as histidine, can be phosphorylated in the presence of a kinase. Cells contain a number of kinases, and each kinase may be capable of phosphorylating one or more amino acids. For example, some kinases phosphorylate serine and threonine, while others phosphorylate serine, theronine, and tyrosine. Changes in the nucleic acid sequence of viral genes, have the potential to increase or decrease the post translational phosphorylation of viral proteins, by increasing or decreasing the number of amino acids that can be phosphorylated. Mutations altering the phosphorylation of viral proteins will become apparent when viral genes are translated in the presence of kinases, such as cellular kinases.

In some embodiments, the mutant virus has one or more mutations in at least one codon in the viral genome encoding a phosphorylation site. In some viruses, the mutation is designed to inhibit phosphorylation of at least one phosphorylation site. For example, the mutation can result in amino acid insertions, deletions, and/or substitutions, introduced at the phosphorylation sites in order to block phosphorylation. The mutation can result in substitution of at least one serine, threonine, and/or tyrosine, amino acid by an amino acid, such as alanine. The mutation can result in amino acid insertions, deletions, and/or substitutions that reduce or inhibit phosphorylation of a serine, threonine, or tyrosine by sterically blocking kinase activity.

Mutations may promote or increase post translational phosphorylation of viral proteins in the presence of a kinase. In one embodiment, the mutant virus has one or more mutations in at least one codon in the viral genome encoding an amino acid that is not phosphorylated, such that the substituted amino acid can be phosphorylated in the presence of a kinase. Substitutions may be made at any amino acid such that phosphorylation of the viral protein is increased. The mutation can be a substitution from any amino acid that can not be phosphorylated, to an amino acid that can be phosphorylated, such as an alanine to a serine, threonine, or tyrosine. The mutation can result in amino acid insertions, deletions, and/or substitutions introduced adjacent to phosphorylation sites in order to increase or promote phosphorylation in the presence of kinase. For example, removal of amino acids that sterically block phosphorylation of another amino acid may be replaced or deleted. Mutations in one or more codons in the viral genome resulting in the substitution of one phosphorylation site or another phosphorylation site are also considered. For example a serine can be replaced by threonine. Substitution of the amino acid at phosphorylation sites may increase, decrease, or otherwise alter the phosphorylation of viral proteins by presenting an alternative substrate for the available cellular kinases.

In one embodiment, one or more mutations in at least one codon in the viral genome of a self-replicating VSV genome alters the phosphorylation of the P protein, the L protein, or a combination thereof. Non-limiting illustrations of mutations that alter the phosphorylation of the P protein, and the L protein are described in the examples below.

VSV-G/GFP is an oncolytic VSV virus with a genome encoded by nucleic acid SEQ ID 1 which is a cDNA sense strand.

The P protein of VSV-G/GFP (SEQ ID NO: 3) is encoded by the nucleic acids between 1396-2193 of SEQ ID NO: 1 (SEQ ID NO: 2). The L protein of VSV-G/GFP (SEQ ID NO: 5) is encoded by the nucleic acids between 7027-13356 of SEQ ID NO:1 (SEQ ID NO: 4). The L protein has an amino acid SEQ ID NO: 5.

In the preferred embodiment the virus has a mutation in codon 126 of SEQ ID NO: 3 encoding the P protein. In one embodiment the mutation in codon 126 of SEQ ID NO: 3 results in replacement of the serine (S), with another amino acid such alanine (A), arginine (R), asparagine (N), aspartic acid (D), cysteine (C), glutamine (Q), glutamic acid (E), glycine (G), histidine H), isoleucine (I), leucine (L), lysine (K), methionine (M), phenylalanine (F), proline (P), tryptophan (W), or valine (V). In an alternative embodiment, the mutation in codon 126 of SEQ ID 3, results in replacement of the serine (S) with a leucine (L) (S126L substitution). In the most preferred embodiment, the mutation is a C1772T mutation in nucleic acid SEQ ID NO: 1.

In another embodiment the virus has a mutation in codon 223 of SEQ ID NO: 5 encoding the L protein. In one embodiment the mutation in codon 223 results in a replacement of the aspartic acid (D) with a serine (5), threonine (T), or tyrosine (Y). In a further embodiment the mutation in codon 223 results in a replacement of the aspartic acid (D) in VSV-G/GFP with a tyrosine (Y) (D223Y substitution). In a preferred embodiment, the mutation is a G7693T mutation that appears in nucleic acid SEQ ID NO: 1.

Some viruses have more than one mutation. For example, a virus can have mutations that result in a change of both the L and P proteins. This mutation may or may not alter phosphorylation state. A virus can have mutations that result in a decrease in the phosphorylation of both the P and L proteins. Mutations of more than one nucleic acid are also possible, and may result in altered phosphorylation of both the P and L proteins at the same time. For example, a virus can have mutations that result in an increase in phosphorylation of the P protein and a decrease in the phosphorylation of the L protein. In a preferred embodiment, the composition includes a virus with a decrease in phosphorylation of the P protein and an increase in the phosphorylation of the L protein. In the most preferred embodiment, the composition includes a VSV with both a S126L substitution in the P protein encoded by SEQ ID NO: 3 and a D223Y substitution in the L protein encoded by SEQ ID NO 5.

In preferred embodiments, the virus is VSV-rp30 encoded by SEQ ID NO: 6 which is a cDNA sense strand VSV-rp30 was generated by growing VSV for many generations on glioblastoma cells, and the resultant virus displayed enhanced infection of the U87 glioblastoma line on which the virus had been cell-adapted, and on other glioblastoma lines (Wollmann et al, *J. Virol.*, 79(10): 6005-6022 (2005)). The resulting change in phenotype was achieved by combining VSV's inherent potential to adapt to different hosts with the application of selective pressure during viral propagation. Sequencing VSV-rp30 identified two amino acid-altering mutations. One mutation is in the P protein encoded by nucleic acid SEQ ID NO: 7,

```
atggataatctcacaaaagttcgtgagtatctcaagtcctattctcgtct ggatcaggcggtaggagagatagatgagatcgaagcacaacgagctgaaa agtccaattatgagttgttccaagaggatggagtggaagagcatactaa gccctcttattttcaggcagcagatgattctgacacagaatctgaaccag aaattgaagacaatcaaggcttgtatgcaccagatccagaagctgagcaa gttgaaggctttatacaggggcctttagatgactatgcagatgaggaagt ggatgttgtatttacttcggactggaaacagcctgagcttgaatctgacg agcatggaaagaccttacggttgacattgccagagggtttaagtggagag cagaaatcccagtggctttcgacgattaaagcagtcgtgcaaagtgccaa atactggaatctggcagagtgcacatttgaagcatcgggagaagggtca
```

-continued
```
ttatgaaggagcgccagataactccggatgtatataaggtcactccagtg atgaacacacatccgtcccaatcagaagcagtatcagatgtttggtctct ctcaaagacatccatgactttccaacccaagaaagcaagtcttcagcctc tcaccatatccttggatgaattgttctcatctagaggagagttcatctct gtcggaggtgacggacgaatgtctcataaagaggccatcctgctcggcct gagatacaaaaagttgtacaatcaggcgagagtcaaatattctctgtag,
``` and amino acid sequence

```
                                                (SEQ ID NO: 8)
mdnltkvreylksysrldqavgeideieaqraeksnyelfqedgveehtk psyfqaaddsdtesepeiednqglyapdpeaeqvegfiqgplddyadeev dvvftsdwkqpelesdehgktlrltlpeglsgeqksqwlstikavvqsak ywnlaectfeasgegvimkerqitpdvykvtpvmnthpsqseavsdvwsl sktsmtfqpkkaslqpltisldelfssrgefisvggdgrmshkeaillgl rykklynqarvkysl.
```

Another mutation is in the L protein encoded by nucleic acid SEQ ID NO: 9, and by amino acid SEQ ID NO: 10.

2. Gene Switching and Rearrangement

VSV is highly immunogenic, and a substantial B and T cell response from the adaptive immune system will ultimately limit VSV infection, which is good from the perspective that it will halt runaway long-lasting viral infections. A virus that shows enhanced selectivity, and a faster rate of infection, will have a greater likelihood of eliminating cancer cells before the virus is eliminated by the immune system. However, the use of VSV against cancer cells does not have to be restricted to a single application. By molecular substitution of the G-protein for enhancing immune responses against foreign genes expressed by VSV, one could switch the original Indiana G protein of the virus with the G protein from VSV New Jersey or Chandipura, allowing a slightly different antigen presentation, and reducing the initial response of the adaptive immune system to second or third oncolytic inoculations with VSV.

It also may be desirable to rearrange the VSVrp30 genome. For example, shifting the L-gene to the sixth position, by rearrangement or insertion of an additional gene upstream, can result in attenuated L-protein synthesis and a slight reduction in replication (Dalton and Rose, Virology, 279(2):414-21 (2001)), an advantage when considering treatment of the brain. Additional examples of attenuating VSV viruses by gene shifting, gene truncations, gene deletions, and combinations thereof, are described in Wollmann, et al., *J. Virol.*, (2009) Epub; *J. Virol.* 84(3): (2010))

3. Viruses Engineered to Express Targeting or Therapeutic Proteins

Viruses may be modified to express one or more targeting or therapeutic proteins, separately or as a part of other expressed proteins. The viral genome of VSV has the capacity to accommodate additional genetic material. At least two additional transcription units, totaling 4.5 kb, can be added to the genome, and methods for doing so are known in the art. The added genes are stably maintained in the genome upon repeated passage (Schnell, et al., *EMBO Journal*, 17:1289-1296 (1998); Schnell, et al., *PNAS*, 93: 11359-11365 (1996); Schnell, et al., *Journal of Virology*, 70:2318-2323 (1996); Kahn, et al., *Virology*, 254, 81-91 (1999)).

Viruses can be engineered to include one or more additional genes that target the virus to cells of interest, see for example U.S. Pat. No. 7,429,481. In preferred embodiments, expression of the gene results in expression of a ligand on the surface of the virus containing one or more domains that bind to antigens, ligands or receptors that are specific to tumor cells, or are upregulated in tumor cells compared to normal tissue. Appropriate targeting ligands will depend on the cell or cancer of interest and will be known to those skilled in the art.

For example, virus can be engineered to bind to antigens, ligands or receptors that are specific to tumor cells or tumor-associated neovasculature, or are upregulated in tumor cells or tumor-associated neovasculature compared to normal tissue.

a. Antigens, Ligands and Receptors to Target

1. Tumor-Specific and Tumor-Associated Antigens

In one embodiment the viral surface contains a domain that specifically binds to an antigen that is expressed by tumor cells. The antigen expressed by the tumor may be specific to the tumor, or may be expressed at a higher level on the tumor cells as compared to non-tumor cells. Antigenic markers such as serologically defined markers known as tumor associated antigens, which are either uniquely expressed by cancer cells or are present at markedly higher levels (e.g., elevated in a statistically significant manner) in subjects having a malignant condition relative to appropriate controls, are known.

Tumor-associated antigens may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melonoma associated antigens, etc.) (see, e.g., U.S. Pat. No. 6,699,475; Jager, et al., *Int. J. Cancer*, 106:817-20 (2003); Kennedy, et al., *Int. Rev. Immunol.*, 22:141-72 (2003); Scanlan, et al. *Cancer Immun.*, 4:1 (2004)).

Genes that encode cellular tumor associated antigens include cellular oncogenes and proto-oncogenes that are aberrantly expressed. In general, cellular oncogenes encode products that are directly relevant to the transformation of the cell, so these antigens are particularly preferred targets for immunotherapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene. Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. J. Med.*, 309:883 (1983); Lloyd, et al., *Int. J. Canc.*, 71:842 (1997). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.*, 36:755 (1997); Sarandakou, et al., *Eur. J. Gynaecol. Oncol.*, 19:73 (1998); Meier, et al., *Anticancer Res.*, 17(4B):2945 (1997); Kudoh, et al., *Gynecol. Obstet. Invest.*, 47:52 (1999)). Elevated serum CA125 may also accompany neuroblastoma (e.g., Hirokawa, et al., *Surg. Today*, 28:349 (1998), while elevated CEA and SCC, among others, may accompany colorectal cancer (Gebauer, et al., *Anticancer Res.*, 17(4B):2939 (1997)).

The tumor associated antigen mesothelin, defined by reactivity with monoclonal antibody K-1, is present on a majority of squamous cell carcinomas including epithelial ovarian, cervical, and esophageal tumors, and on mesotheliomas (Chang, et al., *Cancer Res.*, 52:181 (1992); Chang, et al., *Int. J. Cancer*, 50:373 (1992); Chang, et al., *Int. J. Cancer*, 51:548 (1992); Chang, et al., *Proc. Natl. Acad. Sci. USA*, 93:136 (1996); Chowdhury, et al., *Proc. Natl. Acad. Sci. USA*, 95:669 (1998)). Using MAb K-1, mesothelin is detectable only as a cell-associated tumor marker and has not been found in soluble form in serum from ovarian cancer patients, or in medium conditioned by OVCAR-3 cells (Chang, et al., *Int. J. Cancer*, 50:373 (1992)). Structurally related human mesothelin polypeptides, however, also include tumor-associated antigen polypeptides such as the distinct mesothelin related antigen (MRA) polypeptide, which is detectable as a naturally occurring soluble antigen in biological fluids from patients having malignancies (see WO 00/50900).

A tumor antigen may include a cell surface molecule. Tumor antigens of known structure and having a known or described function, include the following cell surface receptors: HER1 (GenBank Accession NO: U48722), HER2 (Yoshino, et al., *J. Immunol.*, 152:2393 (1994); Disis, et al., Canc. Res., 54:16 (1994); GenBank Ace. Nos. X03363 and M17730), HER3 (GenBank Ace. Nos. U29339 and M34309), HER4 (Plowman, et al., *Nature*, 366:473 (1993); GenBank Ace. Nos. L07868 and T64105), epidermal growth factor receptor (EGFR) (GenBank Acc. Nos. U48722, and KO3193), vascular endothelial cell growth factor (GenBank NO: M32977), vascular endothelial cell growth factor receptor (GenBank Acc. Nos. AF022375, 1680143, U48801 and X62568), insulin-like growth factor-1 (GenBank Ace. Nos. X00173, X56774, X56773, X06043, European Patent No. GB 2241703), insulin-like growth factor-II (GenBank Ace. Nos. X03562, X00910, M17863 and M17862), transferrin receptor (Trowbridge and Omary, *Proc. Nat. Acad. USA*, 78:3039 (1981); GenBank Acc. Nos. X01060 and M11507), estrogen receptor (GenBank Acc. Nos. M38651, X03635, X99101, U47678 and M12674), progesterone receptor (GenBank Ace. Nos. X51730, X69068 and M15716), follicle stimulating hormone receptor (FSH-R) (GenBank Ace. Nos. Z34260 and M65085), retinoic acid receptor (GenBank Ace. Nos. L12060, M60909, X77664, X57280, X07282 and X06538), MUC-1 (Barnes, et al., *Proc. Nat. Acad. Sci. USA*, 86:7159 (1989); GenBank Ace. Nos. M65132 and M64928) NY-ESO-1 (GenBank Acc. Nos. AJ003149 and U87459), NA 17-A (PCT Publication NO: WO 96/40039), Melan-A/MART-1 (Kawakami, et al., *Proc. Nat. Acad. Sci. USA*, 91:3515 (1994); GenBank Ace. Nos. U06654 and U06452), tyrosinase (Topalian, et al., *Proc. Nat. Acad. Sci. USA*, 91:9461 (1994); GenBank Ace. NO: M26729; Weber, et al., *J. Clin. Invest*, 102:1258 (1998)), Gp-100 (Kawakami, et al., *Proc. Nat. Acad. Sci. USA*, 91:3515 (1994); GenBank Ace. NO: S73003, Adema, et al., *J. Biol. Chem.*, 269:20126 (1994)), MAGE (van den Bruggen, et al., *Science*, 254:1643 (1991)); GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Ace. NO: U19180; U.S. Pat. Nos. 5,683,886 and 5,571,711), GAGE (GenBank Am. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Ace. Nos. X86175, U90842, U90841 and X86174), carcinoembryonic antigen (CEA, Gold and Freedman, *J. Exp. Med.*, 121:439 (1985); GenBank Acc. Nos. M59710, M59255 and M29540), and PyLT (GenBank Acc. Nos. J02289 and J02038); p97 (melanotransferrin) (Brown, et al., *J. Immunol.*, 127:539-46 (1981); Rose, et al., *Proc. Natl. Acad. Sci. USA*, 83:1261-61 (1986)).

Additional tumor associated antigens include prostate surface antigen (PSA) (U.S. Pat. Nos. 6,677,157; 6,673,545); β-human chorionic gonadotropin β-HCG) (McManus, et al., *Cancer Res.*, 36:3476-81 (1976); Yoshimura, et al., *Cancer*, 73:2745-52 (1994); Yamaguchi, et al., *Br. J. Cancer*, 60:382-84 (1989): Alfthan, et al., *Cancer Res.*, 52:4628-33 (1992)); glycosyltransferase β-1,4-N-acetylgalactosaminyltransferases (GalNAc) (Hoon, et al., *Int. J. Cancer*, 43:857-62 (1989); Ando, et al., *Int. J. Cancer*, 40:12-17 (1987); Tsuchida, et al., *J. Natl. Cancer*, 78:45-54 (1987); Tsuchida, et al., *J. Natl. Cancer*, 78:55-60 (1987)); NUC18 (Lehmann, et al., *Proc. Natl. Acad. Sci. USA*, 86:9891-95 (1989); Lehmann, et al., *Cancer Res.*, 47:841-45 (1987)); melanoma antigen gp75 (Vijayasardahi, et al., *J. Exp. Med.*, 171:1375-80 (1990); GenBank Accession NO: X51455); human cytokeratin 8; high molecular weight melanoma antigen (Natoli, et al., *Cancer*, 59:55-63 (1987); keratin 19 (Datta, et al., *J. Clin. Oncol.*, 12:475-82 (1994)).

Tumor antigens of interest include antigens regarded in the art as "cancer/testis" (CT) antigens that are immunogenic in subjects having a malignant condition (Scanlan, et al., *Cancer Immun.*, 4:1 (2004)). CT antigens include at least 19 different families of antigens that contain one or more members and that are capable of inducing an immune response, including, but not limited to, MAGEA (CT1); BAGE (CT2); MAGEB (CT3); GAGE (CT4); SSX (CT5); NY-ESO-1 (CT6); MAGEC(CT7); SYCP1 (C8); SPANXB1 (CT11.2); NA88 (CT18); CTAGE (CT21); SPA17 (CT22); OY-TES-1 (CT23); CAGE (CT26); HOM-TES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but are not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-1), gp100 (Pmel 17), tyrosinase, TRP-1, TRP-2, MAGE-1, MAGE-3, BAGE, GAGE-1, GAGE-2, p15 (58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (Ep-CAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Other tumor-associated and tumor-specific antigens are known to those of skill in the art and are suitable for targeting by the disclosed fusion proteins.

2. Antigens Associated with Tumor Neovasculature

Oncolytic viral therapeutics can be more effective in treating tumors by targeting to blood vessels of the tumor. Tumor-associated neovasculature provides a readily accessible route through which protein therapeutics can access the tumor. In one embodiment the viral proteins contain a domain that specifically binds to an antigen that is expressed by neovasculature associated with a tumor.

The antigen may be specific to tumor neovasculature or may be expressed at a higher level in tumor neovasculature when compared to normal vasculature. Exemplary antigens that are over-expressed by tumor-associated neovasculature as compared to normal vasculature include, but are not limited to, VEGF/KDR, Tie2, vascular cell adhesion molecule (VCAM), endoglin and $\alpha_5\beta_3$ integrin/vitronectin. Other antigens that are over-expressed by tumor-associated neovasculature as compared to normal vasculature are known to those of skill in the art and are suitable for targeting by the disclosed fusion proteins.

3. Chemokines/Chemokine Receptors

In another embodiment, the fusion proteins contain a domain that specifically binds to a chemokine or a chemokine receptor. Chemokines are soluble, small molecular weight (8-14 kDa) proteins that bind to their cognate G-protein coupled receptors (GPCRs) to elicit a cellular response, usually directional migration or chemotaxis. Tumor cells secrete and respond to chemokines, which facilitate growth that is achieved by increased endothelial cell recruitment and angiogenesis, subversion of immunological surveillance and maneuvering of the tumoral leukocyte profile to skew it such that the chemokine release enables the tumor growth and metastasis to distant sites. Thus, chemokines are vital for tumor progression.

Based on the positioning of the conserved two N-terminal cysteine residues of the chemokines, they are classified into four groups: CXC, CC, CX3C and C chemokines. The CXC chemokines can be further classified into ELR+ and ELR− chemokines based on the presence or absence of the motif 'glu-leu-arg (ELR motif)' preceding the CXC sequence. The CXC chemokines bind to and activate their cognate chemokine receptors on neutrophils, lymphocytes, endothelial and epithelial cells. The CC chemokines act on several subsets of dendritic cells, lymphocytes, macrophages, eosinophils, natural killer cells but do not stimulate neutrophils as they lack CC chemokine receptors except murine neutrophils. There are approximately 50 chemokines and only 20 chemokine receptors, thus there is considerable redundancy in this system of ligand/receptor interaction.

Chemokines elaborated from the tumor and the stromal cells bind to the chemokine receptors present on the tumor and the stromal cells. The autocrine loop of the tumor cells and the paracrine stimulatory loop between the tumor and the stromal cells facilitate the progression of the tumor. Notably, CXCR2, CXCR4, CCR2 and CCR7 play major roles in tumorigenesis and metastasis. CXCR2 plays a vital role in angiogenesis and CCR2 plays a role in the recruitment of macrophages into the tumor microenvironment. CCR7 is involved in metastasis of the tumor cells into the sentinel lymph nodes as the lymph nodes have the ligand for CCR7, CCL21. CXCR4 is mainly involved in the metastatic spread of a wide variety of tumors.

b. Molecular Classes of Targeting Domains

1. Ligands and Receptors

In one embodiment, tumor or tumor-associated neovasculature targeting domains are ligands that bind to cell surface antigens or receptors that are specifically expressed on tumor cells or tumor-associated neovasculature or are overexpressed on tumor cells or tumor-associated neovasculature as compared to normal tissue. Tumors also secrete a large number of ligands into the tumor microenvironment that affect tumor growth and development. Receptors that bind to ligands secreted by tumors, including, but not limited to, growth factors, cytokines and chemokines, including the chemokines discussed above, are suitable for use in the disclosed fusion proteins. Ligands secreted by tumors can be targeted using soluble fragments of receptors that bind to the secreted ligands. Soluble receptor fragments are fragments of polypeptides that may be shed, secreted or otherwise extracted from the producing cells and include the entire extracellular domain, or fragments thereof.

2. Single Polypeptide Antibodies

In another embodiment, tumor or tumor-associated neovasculature targeting domains are single polypeptide antibodies that bind to cell surface antigens or receptors that are specifically expressed on tumor cells or tumor-associated neovasculature or are overexpressed on tumor cells or tumor-associated neovasculature as compared to normal tissue. Single domain antibodies are described above with respect to coinhibitory receptor antagonist domains.

3. Fc Domains

In another embodiment, tumor or tumor-associated neovasculature targeting domains are Fc domains of immunoglobulin heavy chains that bind to Fc receptors expressed on tumor cells or on tumor-associated neovasculature. As defined herein, the Fc region includes polypeptides containing the constant region of an antibody excluding the first constant region immunoglobulin domain. Thus Fc refers to the last two constant region immunoglobulin domains of IgA, IgD, and IgG, and the last three constant region immunoglobulin domains of IgE and IgM. In a preferred embodiment, the Fc domain is derived from a human or murine immunoglobulin. In a more preferred embodiment, the Fc domain is derived from human IgG1 or murine IgG2a including the $C_H2$ and $C_H3$ regions.

4. Therapeutic Proteins

Viruses can also be engineered to include one or more additional genes that encode a therapeutic protein. Suitable therapeutic proteins, such as cytokines or chemokines, are known in the art. Preferred cytokines include, but are not limited to, granulocyte macrophage colony stimulating factor (GM-CSF), tumor necrosis factor alpha (TNFα), tumor necrosis factor beta (TNFβ), macrophage colony stimulating factor (M-CSF), interleukin-1 (IL-1), interleukin-2 (IL-2), interleukin-4 (IL-4), interleukin-5 (IL-5), interleukin-6 (IL-6), interleukin-10 (IL-10), interleukin-12 (IL-12), interleukin-15 (IL-15), interleukin-21 (IL-21), interferon alpha (IFNα), interferon beta (IFNβ), interferon gamma (IFNγ), and TGIF, and variants and fragments thereof.

Suitable chemokines include, but are not limited to, an alpha-chemokine or a beta-chemokine, including, but not limited to, a C5a, interleukin-8 (IL-8), monocyte chemotactic protein 1 alpha (MIP1α), monocyte chemotactic protein 1 beta (MIP1β), monocyte chemoattractant protein 1 (MCP-1), monocyte chemoattractant protein 3 (MCP-3), platelet activating factor (PAFR), N-formyl-methionyl-leucyl-[$^3$H]phenylalanine (FMLPR), leukotriene B$_4$, gastrin releasing peptide (GRP), RANTES, eotaxin, lymphotactin, IP10, I-309, ENA78, GCP-2, NAP-2 and MGSA/gro, and variants and fragments thereof.

B. Pharmaceutical Carriers

Pharmaceutical compositions containing virus may be for systemic or local administration, such as intratumoral. Dosage forms for administration by parenteral (intramuscular (IM), intraperitoneal (IP), intravenous (IV) or subcutaneous injection (SC)), or transmucosal (nasal, vaginal, pulmonary, or rectal) routes of administration can be formulated.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. Therapeutically effective amounts of the viruses disclosed herein cause a reduction in tumor progression of reduction of tumor burden.

For the compositions disclosed herein and nucleic acids encoding the same, appropriate dosage levels for treatment of various conditions in various patients, can be determined by a person skilled in the art, considering the therapeutic context, age, and general health of the recipient. The selected dosage depends upon the desired therapeutic effect, on the route of administration, and on the duration of the treatment desired. Active virus can also be measured in terms of plaque-forming units (PFU). A plaque-forming unit can be defined as areas of cell lysis (CPE) in monolayer cell culture, under overlay conditions, initiated by infection with a single virus particle. Generally dosage levels of virus between $10^2$ and $10^{12}$ PFU are administered to humans. Virus is typically administered in a liquid suspension, in a volume ranging between 10 µl and 100 ml depending on the route of administration. Generally, dosage and volume may be lower for intratumoral injection, than systemic administration or infusion. The dose may be administered once or multiple times. Typically the dose will be 100 µl administered intratumorly in multiple doses, while systemic or regional administration via subcutaneous, intramuscular, intra-organ, or intravenous administration will be from 10 to 100 ml.

The term "pharmaceutically acceptable" means a nontoxic material that does not interfere with the effectiveness of the biological activity of the active ingredients. The term "pharmaceutically-acceptable carrier" means one or more compatible solid or liquid fillers, diluents or encapsulating substances which are suitable for administration to a human or other vertebrate animal. The term "carrier" refers to an organic or inorganic ingredient, natural or synthetic, with which the active ingredient is combined to facilitate the application.

Pharmaceutical compositions may be formulated in a conventional manner using one or more physiologically acceptable carriers including excipients and auxiliaries which facilitate processing of the active compounds into preparations which can be used pharmaceutically. The compositions may be administered in combination with one or more physiologically or pharmaceutically acceptable carriers, thickening agents, co-solvents, adhesives, antioxidants, buffers, viscosity and absorption enhancing agents and agents capable of adjusting osmolarity of the formulation. Proper formulation is dependent upon the route of administration chosen. If desired, the compositions may also contain minor amount of nontoxic auxiliary substances such as wetting or emulsifying agents, dyes, pH buffering agents, or preservatives. The formulations should not include membrane disrupting agents which could kill or inactivate the virus.

1. Formulations for Local or Parenteral Administration

In a preferred embodiment, compositions including oncolytic virus disclosed herein, are administered in an aqueous solution, by parenteral injection. Injection includes, but it not limited to, local, intratumoral, intravenous, intraperitoneal, intramuscular, or subcutaneous. The formulation may also be in the form of a suspension or emulsion. In general, pharmaceutical compositions are provided including effective amounts of virus, and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as anti-oxidants (e.g., ascorbic acid, sodium metabisulfite), and preservatives and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. A preferred solution is phosphate buffered saline or sterile saline.

2. Formulations for Mucosal Administration

In some embodiments, the compositions are formulated for mucosal administration, such as through nasal, pulmonary, or buccal delivery.

Mucosal formulations may include one or more agents for enhancing delivery through the nasal mucosa. Agents for enhancing mucosal delivery are known in the art, see for example U.S. Patent Application No. 20090252672 to Eddington, and U.S. Patent Application No. 20090047234 to Touitou. Acceptable agents include, but are not limited to, chelators of calcium (EDTA), inhibitors of nasal enzymes (boro-leucin, aprotinin), inhibitors of muco-ciliary clearance (preservatives), solubilizers of nasal membrane (cyclodextrin, fatty acids, surfactants) and formation of micelles (surfactants such as bile acids, Laureth 9 and taurodehydrofusidate (STDHF)). Compositions may include one or more absorption enhancers, including surfactants, fatty acids, and chitosan derivatives, which can enhance delivery by modulation of the tight junctions (TJ) (B. J. Aungst, et al., *J. Pharm. Sci.* 89(4):429-442 (2000)). In general, the optimal absorption enhancer should possess the following qualities: its effect should be reversible, it should provide a rapid permeation enhancing effect on the cellular membrane of the mucosa, and it should be non-cytotoxic at the effective concentration level and without deleterious and/or irreversible effects on the cellular membrane, virus membrane, or cytoskeleton of the TJ.

C. Kits

Dosage units include virus in a pharmaceutically acceptable carrier for shipping and storage and/or administration. Active virus should be shipped and stored using a method consistent with viability such as in cooler containing dry ice so that cells are maintained below 4° C., and preferably below −20° C. VSV virus should not be lyophilized. Components of the kit may be packaged individually and can be sterile. In one embodiment, a pharmaceutically acceptable carrier containing an effective amount of virus is shipped and stored in a sterile vial. The sterile vial may contain enough virus for one or more doses. Virus may be shipped and stored in a volume suitable for administration, or may be provided in a concentrated titer that is diluted prior to administration. In another embodiment, a pharmaceutically acceptable carrier containing an effective amount of virus can be shipped and stored in a syringe.

Typical concentrations of viral particles in the sterile saline, phosphate buffered saline or other suitable media for the virus is in the range of $10^8$ to $10^9$ with a maximum of $10^{12}$. Dosage units should not contain membrane disruptive agents nor should the viral solution be frozen and dried (i.e., lyophilized), which could kill the virus.

Kits containing syringes of various capacities or vessels with deformable sides (e.g., plastic vessels or plastic-sided vessels) that can be squeezed to force a liquid composition out of an orifice are provided. The size and design of the syringe will depend on the route of administration. For example, in one embodiment, a syringe for administering virus intratumorally, is capable of accurately delivering a smaller volume (such as 1 to 100 μl). Typically, a larger syringe, pump or catheter will be used to administer virus systemically.

The kits optionally include one or more of the following: bioactive agents, media, excipients and one or more of: a syringe, a bandage, a disinfectant, a local anesthetic, an analgesic agent, surgical thread, scissors, a sterile fluid, and a sterile vessel. Kits for intranasal administration may optionally contain a delivery device for facilitating intranasal delivery, such as a nasal sprayer. The kits are generally provided in a container, e.g., a plastic, cardboard, or metal container suitable for commercial sale. Any of the kits can include instructions for use.

III. Methods of Use

A. Subjects to be treated

In general, the compositions are useful for targeting and destroying a cell or cells of interest. In a preferred embodiment, the cells of interest are cancer cells. For example, compositions are useful as therapeutic compositions, which can be used to treat benign or malignant tumors.

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The compositions and method described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth. The examples below demonstrate that the VSV virus disclosed herein are oncolytic to tumors in vivo.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. The disclosed compositions are particularly effective in treating carcinomas. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, cancers such as vascular cancer such as multiple myeloma, adenocarcinomas and sarcomas, of bone, bladder, brain, breast, cervical, colo-rectal, esophageal, kidney, liver, lung, nasopharangeal, pancreatic, prostate, skin, stomach, and uterine. In some embodiments, the disclosed compositions are used to treat multiple cancer types concurrently. The compositions can also be used to treat metastases or tumors at multiple locations. As shown in the examples below, the oncolytic virus VSV-rp30 is particularly effective in treating gliomas (including astrocytomas) in the brain, as well as bone, breast, prostate, colon, and lung cancers. It can also infect and kill pancreatic and stem cells from brain cancer. In some embodiments, the composition is used to treat lung or breast cancer carcinomas, which are the source of many brain cancers. In a preferred embodiment, a composition containing an oncolytic VSV such as VSV-rp30 is used for treating glioblastoma.

VSV has a good oncolytic profile in part by taking advantage of defects in the innate cellular anti-viral defense system, which is a common feature in malignancies, including colon, breast, prostate, liver, and leukemia. Reduction in interferon-related antiviral defenses enhance infection of cancer cells by VSVrp30. Activation of the interferon pathway protects normal human brain cells from VSV infection while maintaining the vulnerability of human glioblastoma cells to viral destruction (Wollmann, et al. *J. Virol.*, 81(3): 1479-1491 (2007)). In some embodiments, the disclosed compositions and methods are used to treat a population of cells with defects in the interferon system. In preferred embodiments, the cells with a defective interferon system or defective antiviral defense system are tumor cells that are susceptible to VSV infection and destruction in the presence of exogenous interferons such as IFN-α, or IFN-α/β pathway inducer polyriboinosinic polyribocytidylic acid [poly(I:C)].

B. Methods of Administration

Any acceptable method known to one of ordinary skill in the art may be used to administer a formulation to the subject. Preferably, administration of the formulations may be accomplished by any acceptable method which allows an effective amount of the oncolytic virus to reach their target. As generally used herein, an "effective amount" is that amount which is able to induce a desired result in a treated subject. The desired results will depend on the disease or condition to be treated. For example, in treating a subject with a tumor, in one embodiment, an effective amount of the composition reduces or stops tumor progression or at least reduces one or more symptoms of the tumor. Symptoms of cancer may be physical, such as tumor burden, or biological such as proliferation of cancer cells. The actual effective amounts of virus can vary according to factors including the specific virus administered, the particular composition formulated, the mode of administration, and the age, weight, condition of the subject being treated, as well as the route of administration and the disease or disorder.

The particular mode of administration selected will depend upon factors such as the particular formulation, the severity of the state of the subject being treated, and the dosage required to induce an effective response. The administration may be localized (i.e., to a particular region, physiological system, tissue, organ, or cell type) or systemic. The compositions can be administered by a number of routes including, but not limited to, injection: intravenous, intraarterial, intraperitoneal, intramuscular, or subcutaneous, or to a mucosal surface (oral, sublingual or buccal, nasal, rectal, vaginal, pulmonary) and special means such as convection enhanced delivery. In a preferred embodiment, the oncolytic virus is administered in an aqueous solution, by parenteral injection. In one embodiment, the composition is injected locally at the site of treatment, such as a tumor. In some embodiments, the composition is delivered systemically, by injection into the circulatory system (i.e. intravenous) or an appropriate lymphoid tissue, such as the spleen, lymph nodes or mucosal-associated lymphoid tissue. The injections can be given at one, or multiple locations. In a preferred embodiment, one treatment is sufficient. In some embodiments, multiple treatments are required.

The composition can also be administered mucosally. One example of mucosal administration is intranasal delivery. Intranasal administration can result in systemic or local delivery of oncolytic virus. For example, following intranasal delivery, virus gain access to the CNS through the olfactory nerve, which projects to the glomeruli in the olfactory bulb of the brain (van den Pot et al., *J. Virol,* 76 1309-27 (2002)).

C. Combination Therapies

Administration of the disclosed compositions containing oncolytic viruses may be coupled with surgical, radiologic, other therapeutic approaches to treatment of cancer.

1. Surgery

The disclosed compositions and methods can be used as an adjunct to surgery. Surgery is a common treatment for many types of benign and malignant tumors. As it is often not possible to remove all the tumor cells from during surgery, the disclosed compositions containing oncolytic virus are particularly useful subsequent to resection of the primary tumor mass, and would be able to infect and destroy even dispersed tumor cells.

An additional situation where an oncolytic virus may be helpful is in regions where the tumor is either wrapped around critical vasculature, or in an area that is difficult to treat surgically. Widely disseminated metastatic carcinomas are also a potential target given the high efficiency of VSV against many systemic malignancies such as breast, prostate, liver or colon carcinomas or lymphomas (Stojdl et al, 2003; Ahmet et aL., 2000; Bbert et al, 2005; Shinozaki ei al, 2005; Lichty et al., 2004b).

In a preferred embodiment, the disclosed compositions and methods are used as an adjunct or alternative to neurosurgery. The compositions are particularly well suited to treat areas of the brain that is difficult to treat surgically, for instance high grade tumors of the brain stem, motor cortex, basal ganglia, or internal capsule. High grade gliomas in these locations are generally considered inoperable.

2. Therapeutic Agents

The viral compositions can be administered to a subject in need thereof alone or in combination with one or more additional therapeutic agents selected based on the condition, disorder or disease to be treated. A description of the various classes of suitable pharmacological agents and drugs may be found in Goodman and Gilman, *The Pharmacological Basis of Therapeutics*, (11th Ed., McGraw-Hill Publishing Co.) (2005).

Additional therapeutic agents include conventional cancer therapeutics such as chemotherapeutic agents, cytokines, chemokines, and radiation therapy. The majority of chemotherapeutic drugs can be divided into: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to, cisplatin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

Preferred chemotherapeutics will affect tumors or cancer cells, without diminishing the activity of the virus. For example, in a preferred embodiment, the additional therapeutic agent inhibits proliferation of cancer cells without affecting targeting, infectivity, or replication of the virus.

a. Immunosuppressants

It may be desirable to administer viral compositions in combination with an immunosuppressant. Oncolytic viruses such as VSV are highly immunogenic, and a substantial B and T cell response from the adaptive immune system would ultimately limit viral infection. An immunosuppressant attenuates the host immune response and prolongs viral infection. Immunosuppressants are known in the art and include glucocorticoids, cytostatics (such as alkylating agents, antimetabolites, and cytotoxic antibodies), antibodies (such as those directed against T-cell recepotors or Il-2 receptors), drugs acting on immunophilins (such as cyclosporine, tacrolimus, and sirolimus) and other drugs (such as interferons, opioids, TNF binding proteins, mycophenolate, and other small molecules such as fingolimod). The dosage ranges for immunosuppressant agents are known in the art. The specific dosage will depend upon the desired therapeutic effect, the route of administration, and on the duration of the treatment desired. For example, when used as an immunosuppressant, a cytostatic maybe administered at a lower dosage than when used in chemotherapy. Suitable immunosuppressants include, but are not limited to, FK506, prednisone, methylprednisolone, cyclophosphamide, thalidomide, azathioprine, and daclizumab, physalin B, physalin F, physalin G, secosteroids purified from *Physalis angulata* L., 15-deoxyspergualin, MMF, rapamycin and its derivatives, CCI-779, FR 900520, FR 900523, NK86-1086, depsidomycin, kanglemycin-C, spergualin, prodigiosin25-c, cammunomicin, demethomycin, tetranactin, tranilast, stevastelins, myriocin, gliotoxin, FR 651814, SDZ214-104, bredinin, WS9482, mycophenolic acid, mimoribine, misoprostol, OKT3, anti-IL-2 receptor antibodies, azasporine, leflunomide, mizoribine, azaspirane, paclitaxel, altretamine, busulfan, chlorambucil, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, etoposide, teniposide, vinblastine, vincristine, vinorelbine, procarbazine, asparaginase, pegaspargase, octreotide, estramustine, and hydroxyurea, and combinations thereof. Preferred immunosuppressants will preferentially reduce or inhibit the subject's immune response, without reducing or inhibiting the activity of the virus. For example, in a preferred embodiment, the additional therapeutic agent inhibits activation and/or proliferation without affecting targeting, infectivity, or replication of the virus.

b. Anticancer Agents

The compositions can be administered with an antibody or antigen binding fragment thereof specific for growth factor receptors or tumor specific antigens. Representative growth factors receptors include, but are not limited to, epidermal growth factor receptor (EGFR; HER1); c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II R/M-6-P receptor); insulin receptor related kinase (IRRK); platelet-derived growth factor receptor (PDGFR); colony-stimulating factor-1 receptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor receptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK; Cek5; Elk/Cek6; Cek7; Sek/Cek8; Cek9; Cek10; HEK11; 9 Ror1; Ror2; Ret; Axl; RYK; DDR; and Tie.

c. Therapeutic Proteins

It may be desirable to administer the disclosed compositions in combination with therapeutic proteins. VSV is an effective oncolytic virus, in-part, by taking advantage of defects in the interferon system. Administration of therapeutic proteins such as IFN-α, or IFN-α/β pathway inducer polyriboinosinic polyribocytidylic acid [poly(I:C)] are effective in protecting normal cells from the oncolytic activity, while leaving the tumor cells susceptible to infection and death (Wollmann, et al. *J. Virol.*, 81(3): 1479-1491 (2007), (Wollmann, et al., *J. Virol*, (2009)). Therefore, in some embodiments, the disclosed compositions are administered in combination with a therapeutic protein to reduce infectivity and death of normal cells. Suitable therapeutic proteins are described above.

d. Peripheral Immunization

It may be desirable to administer the disclosed compositions after peripheral immunization with the virus. Evidence suggests that peripheral activation of the systemic immune system can protect the brain from VSV damage (Ozduman, et al., *J. Virol.*, 83(22):11540-11549 (2009)). Immunization is carried out first, preferably by intranasal or intramuscular delivery, or combination thereof. Immunization is followed by administration of therapeutic compositions by intracranial injection.

IV. Methods of Manufacture

A. Engineering Recombinant VSV Viruses

The VSV genome is a single negative-sense, non-segmented stand of RNA that contains five genes (N, L, P, M, and G) and has a total size of 11.161 kb. Methods of engineering recombinant viruses by reconstituting VSV from DNA encoding a positive-sense stand of RNA are known in the art (Lawson, et al., *PNAS,* 92:4477-4481 (1995), Dalton and Rose, *Virology,* 279:414-421 (2001)). For example, recombinant DNA can be transcribed by T7 RNA polymerase to generate a full-length positive-strand RNA complimentary to the viral genome. Expression of this RNA in cells also expressing the VSV nucleocapsid protein and the two VSV polymerase subunits results in production of VSV virus (Lawson, et al., *PNAS,* 92:4477-4481 (1995)). In this way, VSV viruses can be engineered to express variant proteins, additional proteins, foreign antigens, targeting proteins, or therapeutic proteins using known cloning methods.

B. Creating Mutant VSV Virus

RNA viruses are prone to spontaneous genetic variation. The mutation rate of VSV is about $10^{-4}$ per nucleotide replicated, which is approximately one nucleotide change per genome (Drake, et al., *Proc. Natl. Acad. Sci. USA,* 96:13910-13913). Therefore, mutant VSV viruses exhibiting desired properties can be developed by applying selective pressure. Methods for adaption of VSV viruses through repeated passaging is described in the art. See, for example, Wollmann, et al., *J. Virol.,* 79(10): 6005-6022 (2005). Selective pressure can be applied by repeated passaging and enhanced selection to create mutant virus with desirable traits such as increased infectivity and oncolytic potential for a cell type of interest. The cell type of interest could be general, such as cancer cells, or specific such as glioblastoma cells. Mutant virus can also be selected based on reduced toxicity to normal cells. Methods of enhanced selection include, but are not limited to, short time for viral attachment to cells, collection of early viral progeny, and preabsorption of viral particles with high affinity of undesirable cells (such as normal cells). Mutations can be identified by sequencing the viral genome, for instance as described in Example 4 below.

DNA encoding the VSV genome can also be used as a substrate for random or site directed mutagenesis to develop VSV mutant viruses. Mutagenesis can be accomplished by a variety of standard, mutagenic procedures. Changes in single genes may be the consequence of point mutations that involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of nucleic acid replication or the movement of transposable genetic elements (transposons) within the genome. They also are induced following exposure to chemical or physical mutagens. Such mutation-inducing agents include ionizing radiations, ultraviolet light and a diverse array of chemicals such as alkylating agents and polycyclic aromatic hydrocarbons all of which are capable of interacting either directly or indirectly (generally following some metabolic biotransformations) with nucleic acids. The nucleic acid lesions induced by such environmental agents may lead to modifications of base sequence when the affected DNA is replicated or repaired and thus to a mutation. Mutation also can be site-directed through the use of particular targeting methods. Various types of mutagenesis such as random mutagenesis, e.g., insertional mutagenesis, chemical mutagenesis, radiation mutagenesis, in vitro scanning mutagenesis, random mutagenesis by fragmentation and reassembly, and site specific mutagenesis, e.g., directed evolution, are described in U.S. Patent Application No. 2007/0026012.

Mutant viruses can be prepared by site specific mutagenesis of nucleotides in the DNA encoding the protein, thereby producing DNA encoding the mutant. Techniques for making substitution mutations at predetermined sites in DNA having a known sequence are well known, for example M13 primer mutagenesis and PCR mutagenesis. Amino acid substitutions are typically of single residues, but can occur at a number of different locations at once. Insertions usually will be on the order of about from 1 to 10 amino acid residues; and deletions will range about from 1 to 30 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place.

EXAMPLES

Example 1

VSV-rp30 Kills Human Cancer Cells that can Cause Brain Tumors

Materials and Methods

Cell Culture

U87MG human high-grade glioma cells and 411 mouse mammary carcinoma cells were obtained from American Type Culture Collection (Rockville, Md.). A549 and Calu-1 human lung carcinomas and T-47D, MCF-7, and 81474 human breast carcinoma cells were provided by the Yale Cancer Center (Yale University, New Haven, Conn.). U118MG glioma cells were provided by Dr. R. Matthews, Yale University. Primary human glioblastoma cultures were established from tissue derived from two patients undergoing respective surgery. Nontumor primary human astrocytes were prepared as explant outgrowth cultures from human temporal lobectomy material, removed for intractable epilepsy, solely for the benefit of the patient, and the use was approved by the Yale University Human Investigation Committee. Astrocyte identity was confirmed by positive immunofluorescence for human glial fibrillary acidic protein. Cells were maintained in Minimal Essential Medium (Invitrogen, Carlsbad, Calif.) supplemented with 10% fetal bovine serum, 1% sodium pyruvate, 100 μM nonessential amino acids, and 25 mM HEPES buffer. For VSV susceptibility experiments, $2\times10^5$ cells were cultured in six-well plates and infected with VSVrp30a at a multiplicity of infection (MOI) of 1. The total number of viable and infected cells was counted at 12 h intervals in 15 high-magnification microscopic fields.

Results

To test the tumor cell tropism, VSVrp30a was tested on five human carcinoma lines, selected by the fact that lung and breast cancers are the most common sources for brain metastasis. All human cancer lines tested, including A549, Calu-1 lung carcinoma, and T-47D, MCF7, and BT-474 breast carcinoma, were infected and killed by VSVrp30a at an MOI of 1. All cells exhibited viral green fluorescence by 60 h after infection, and all cells, dividing and nondividing, in the culture dish were killed by 48-72 h after infection (FIG. 1). In addition, multiple cultures were established from tissue derived from resected glioblastoma surgery. These primary high-grade gliomas were grown in culture and infected with VSVrp30a at an MOI of 1. Complete infection and presence of cytopathic effects were observed within 36 h after virus application indicating that the oncolytic capacity of VSV seen on established glioma and other cancer cell lines could translate to tumor cells directly derived from human cancer patients.

Example 2

VSV-rp30 has Improved Oncolytic Potential

Materials and Methods
Viruses
VSV-G/GFP (additional G protein with GFP reporter fusion inserted at 5th gene position), VSV-M51/CT9 (M protein M51 mutation+G protein with cytoplasmic tail truncated to 9 amino acids) and VSV-1'GFP (GFP reporter inserted in $1^{st}$ gene position) were obtained from J. Rose (Yale University) and propagated using BHK-21 cells (FIG. 2). VSV-rp30 was generated from VSV-G/GFP through repeated passage and adaptation on U-87MG glioblastoma cells. The four VSVs used in the present study (VSV-G/GFP, VSV-rp30, VSV-M51/CT9 and VSV-1'GFP) were all derived from a recombinant version of the San Juan strain of Indiana serotype VSV, the genome of which consists of a single negative strand of RNA that encodes five genes, N, P, M, G and L, depicted on the top (VSV). (see FIG. 2). All four express enhanced GFP, a fluorescent reporter protein that enables the visualization of infected cells. VSV-G/GFP (G/GFP) incorporates a GFP reporter gene (shown in grey) encoding an additional copy of the G-protein with a C-terminal fusion of GFP. VSV-rp30 (RP30) is a glioblastoma cell-adapted variant of VSV-G/GFP that has been previously described to display increased oncolytic activity in glioblastoma cells. The P and L genes (shown in white) are the genes found to contain the mutations S126L and D223Y identified in the present study. VSV-M51/CT9 (M51/CT9) contains a GFP reporter gene (in grey) inserted between the G and L genes. The M gene (in white) has been modified to delete the methionine at position 51 of the M protein and the G gene (white) encodes a truncated version of the G protein that removes all but 9 of the 27 amino acids of the C-terminal cytoplasmic tail. Both of these mutations have previously been reported to result in attenuated viral propagation (Clarke et al., *J. Virol.*, 81: 2056-2064 (2007); Publicover et al., *J. Virol.*, 78: 9317-9324 (2004); Publicover et al., *J. Virol.*, 80: 7028-7036 (2006)). VSV-1'GFP (1'GFP) contains a GFP reporter gene (grey) inserted into the first position in the gene order, thus decreasing the level of transcription from the remaining five downstream genes and leading to attenuated viral propagation (Clarke et al., *J. Virol.*, 81: 2056-2064 (2007); Flanagan et al., *J. Virol.*, 75: 6107-6114 (2001); Ramsburg et al., *J. Virol.*, 79: 15043-15053 (2005)).

Cell Lines
The human glioblastoma tumor cell line U-87MG, the baby hamster kidney cell line BHK-21, and the embryonic mouse cell line NIFV3T3 were obtained from the American Type Culture Collection (ATCC) (Manassas, Va.). The human glioblastoma tumor cell lines U-118MG and U-373MG were provided by R. Matthews, Yale University. The human prostate tumor cell line DU-145 was provided by B. Gullen, Yale University. The human cell lines SJSA-I, BT-549, T-47D, HCT116, LS180, SfV480 and A549 and established from tumors of bone, breast, breast, colon, colon, colon and lung, respectively, were provided by S. Mella, Yale University Cancer Center. The primary human astrocyte culture was established from human brain tissue obtained in the course of epilepsy surgery, as described by Wollmann, et al., *J. Virol,* 81:1479-1491 (2007), with patient welfare being the sole basis for resection of brain tissue. All cell lines were propagated using MEM growth media consisting of minimum essential medium (Gibco, Carlsbad, Calif.) supplemented with 10% fetal bovine serum (Gibco) and 1% penicillin/streptomycin solution (Gibco) and housed in a humidified incubator at 37° C. supplied with 57% $CO_2$.

Plaque Size Assay
In order to compare VSV propagation among various cell types, a plaque size assay was devised. For each cell type, confluent cell monolayers were grown in six-well plates and triplicate wells were infected with each of the VSVs to be tested. Immediately prior to viral inoculation, media in all wells was aspirated and replaced with 0.9 ml of MEM growth medium followed by inoculation using 0.1 ml of serially diluted VSV generated previously and stored in MEM growth medium at −80° C. After inoculation, plates were placed back in the incubator for 1 hr to allow time for the virus to adsorb into the cell monolayer. The inoculation media was then aspirated and cell monolayers were overlaid with 2 ml of 0.5% (w/vol) agarose (Ultrapure GPG/LE; American Bioanalytical, Natick, Mass.) in MEM growth medium. After solidification of the agarose, plates were incubated at 37° C. in 5Vo $CO_2$ for 18-36 hr to allow time for plaque development. Since each of the VSVs expressed enhanced GFP as a reporter protein, fluorescent microscopic imaging was employed to visualize and measure individual GFP fluorescent plaques. The fluorescent imaging system consisted of an Olympus IX71 inverted microscope (Tokyo, Japan) fitted with an Olympus UPlanFl 4x objective and EGFP filter set. Images were captured using a SPOT-RT digital camera (Diagnostic Instruments, Sterling Heights, Mich.) and further processed using Adobe Photoshop 7.0 software (Adobe Systems, San Jose, Calif.). Fluorescent plaque diameter measurements were taken after VSV-G/GFP plaques had grown to between 0.5-1.5 mm in diameter. For each VSV tested, 30 plaques were randomly selected under fluorescent visualization and measured across their diameter to the nearest 0.05 mm. The mean VSV-G/GFP plaque diameter was used as the normalization factor for all plaque diameter measurements in each cell line (normalized mean VSV-G/GFP plaque diameter=100%). All uncertainties represent the standard error of the mean (SE) of normalized values. Statistical calculations were performed using InStat 3.0 software (GraphPad Software, La Jolla, Calif.). One-way analysis of variance (ANOVA) with post hoc Bonferroni multiple comparison tests were used to determine statistical significance. Comparisons between groups yielding a p-value<0.05 were considered significantly different.

Results
In order to more fully assess the relative differences in the growth characteristics of VSV-rp30 with respect to the parent VSV-G/GFP from which it was derived, a panel of eleven widely used cancer cell lines was assembled for use in a plaque size assay. These lines were established from tumors of a number of different types of common human adult cancers including bone, brain, breast, colon, lung and prostate. Additionally, two other GFP-expressing VSVs were included for comparison in the assay (VSVM5I/CT9 and VSV-1'GFP) that have been reported to display attenuated growth characteristics in vitro (Clarke et al., *J. Virol.*, 81: 2056-2064 (2007); Publicover et al., *J. Virol.*, 78: 9317-9324 (2004); Publicover et al., *J. Virol.*, 80: 7028-7036 (2006); Ramsburg et al., *J. Virol.*, 79: 15043-15053 (2005)). A diagram illustrating the genomic composition of each of the four VSVs assayed is shown in FIG. 2. Analysis of the average size of VSV-rp30 plaques relative to those produced by VSV-G/GFP indicated that VSV-rp30 plaques had a significantly larger diameter (165%±7 SE, p<0.001, n=30) than VSV-G/GFP plaques (100%±5 SE, n=30) and that both VSV-M51/CT9 and VSV-1'GFP plaques had significantly smaller diameters (55%±3 SE, p<0.001, n=30; 53%±4SE, p<0.001, n=30) respectively, than VSV-G/GFP plaques (FIG. 3).

Figure 3:
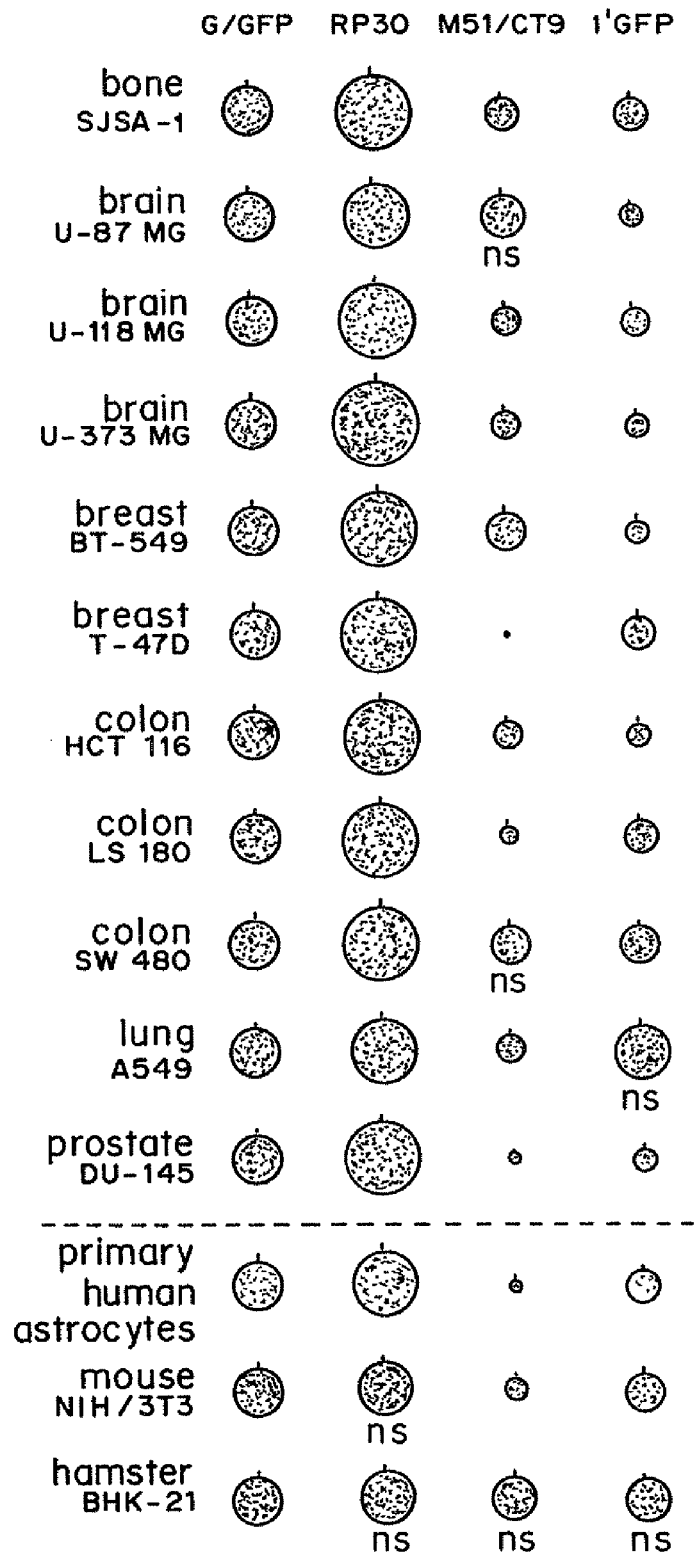
FIG. 3 is a chart illustrating the plaque size (diameter) that developed in the monolayer of 11 cancer cell lines (as labeled from top to bottom above the dotted line) and 3 non-cancer cell lines (as labeled from top to bottom below the dotted line) following infection with 4 different VSV viruses (as labeled from left to right). Each circle represents the mean of 30 randomly selected plaques measured across their diameter, then normalized with respect to the corresponding VSV-G/GFP mean plaque diameter. Small marks at the top of each circle represent standard error of the mean. "NS" indicates the only plaques that were not statistically different ($p<0.05$).

A similar analysis was performed for each of the 11 cancer cell lines (FIG. 3). Each circle represents the mean of 30 randomly selected plaques measured across their diameter, then normalized with respect to the corresponding VSV-G/GFP mean plaque diameter. The small marks at the top of each circle represent the standard error of the mean. VSV-rp30 plaques were significantly larger (p<0.001) than VSV-G/GFP plaques in all cancer cell lines tested. The VSV-rp30 plaques ranged in average diameter from a low of 137%±6 SE (p<0.001, n=30) in brain U-87MG cells to a high of 165% in the previously mentioned brain U-373MG cells. In 9 of 11 cancer lines, VSV-4 M5I/CT9 plaques were significantly smaller than VSV-G/GFP plaques and ranged in average diameter from a low of 10%±1 SE (p<0.001, n=30) in breast T-47D cells to a high of 83%±4 SE (n=30) in brain U-87MG cells. In 10 of 11 cancer lines, VSV-1'GFP plaques were also significantly smaller, ranging in diameter from a low of 39%±4 SE (p<0.001, n=30) in brain U-87MG cells to a high of 114%±5 SE (n=30) in lung A549 cells.

Three additional non-cancer-derived cell lines (primary human astrocytes, mouse NIH3T3 and hamster BHK-21 cells) were also tested in the assay (FIG. 3). The primary 12 human astrocyte cells displayed an average VSV-rp30 plaque diameter (118%±6 SE, n=30) that was marginally larger than that of VSV-G/GFP plaques (100%±5 SE, n=30), however, this difference achieved significance only at the p<0.05 level of confidence. Conversely, both VSV-MS1/CT9 and VSV-1'GFP plaques had significantly smaller diameters (19%±3 SE, p<0.001, n=30; 61%±5 SE, p<0.001, n=30, respectively). The mouse NIH/3T3 cells displayed an average VSV-rp30 plaque diameter (98%±6 SE, n=30) that was not significantly different from that of VSV-G/GFP (100%±7 SE, n=30), however, both VSV-MS1/CT9 and VSV-1'GFP plaques had significantly smaller diameters (41%±3 SE, p<0.001, n=30; 74%±6 SE, p<0.05, n=30, respectively). Finally, hamster BHK-21 cells displayed average VSV-rp30 (109%+3 SE, n=30), VSV-M51/CT9 (88%+4 SE, n=30), and VSV-1'GFP (93%±4 SE, n=30) plaque diameters that were not significantly different than that of VSV-G/GFP (100%±4 SE, n=30).

Taken together, these data indicate that VSV-rp30 plaques develop to become significantly larger than VSV-G/GFP plaques when grown on cancer-derived cells, in contrast to the little or no difference in size observed when grown on non-cancerous cells. Additionally, VSV-M51/CT9 and VSV-1'GFP plaques tend to be significantly smaller than VSV-G/GFP plaques in the majority of cell lines tested, independent of whether the cells are of a cancerous or non-cancerous origin.

The larger plaques associated with VSV-rp30 were indicative of a faster rate of infection and replication of this virus than the other VSVs tested here. This enhanced rate of infection may prove beneficial in treating cancer, as it would give VSV-rp30 a headstart in the race against the immune system. Although VSV-rp30 was more aggressive in infecting tumors, the relative efficacy of VSV-rp30 in infecting normal human astrocytes was reduced compared with the tumors; this is an attribute of VSV-rp30, as it suggests that the virus has a greater replication potential in tumor than in non-tumor tissue. Based on plaque size, VSV-rp30 displayed a mean 50% greater infection of all human cancer lines than the parent VSV-G/GFP, and showed a three-fold greater infection than VSV-CT9/M51 or VSV-1'GFP. In contrast, VSV-rp30 showed only a modest 9% greater infection on human non-cancer control cells.

Example 3

VSV-rp30 Exhibits Increased Oncolytic Activity

Materials and Methods

Plaque Cytotoxicity Labeling with Ethidium Homodimer

Assessments of cell death were performed on plaques after treatment with ethidium homodimer (EthD-1), an agent that yields a bright red fluorescence upon binding to the exposed nucleic acids of dead or damaged cells. EthD-1 (Molecular Probes, Eugene, Oreg.) was prepared in D-PBS at a 4 µM concentration according to the manufacturer's instructions and 1 ml was used to overlay the agar layer of infected cell monolayers on which plaques had been allowed to develop for 48 hrs. One well from each condition was overlaid with 1 ml of D-PBS alone as a negative EthD-1 control. After incubation for 30 minutes at 37° C., plaques were visualized with the fluorescent microscopic imaging system described above using either EGFP or Texas red filters. Under red fluorescent visualization, plaques were easily identifiable due to the greatly increased density of dead cells labeled by EthD-1. After confirming the location of the plaque using GFP fluorescence, the diameter of the red fluorescent EthD-1 labeled area of cell death associated with the plaque was measured. The diameters of these cytotoxic areas were normalized with respect to the corresponding mean VSV-G/GFP cytotoxic area diameter of each cell line tested. Thirty plaques from each condition were randomly selected and analyzed in this manner and statistical comparisons were performed as described above.

Results

Figure 4:
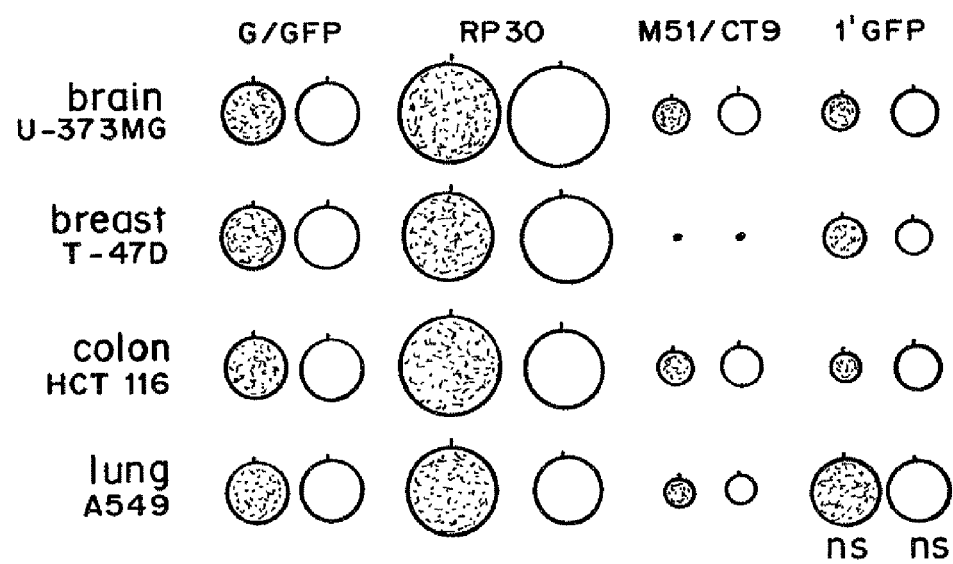
FIG. 4 is a chart illustrating the plaque size (stippled circles) compared to EthD-1 labeled cytotoxic areas (open circles) that developed in the monolayer of four cancer cell lines (as labeled from top to bottom) following infection with 4 different VSV viruses (as labeled from left to right). Measurements were collected and normalized as in FIG. 3.

To assess the oncolytic activity of VSV-rp30 relative to VSV-G/GFP, VSV10 M51/CT9 and VSV-1'GFP, plaque assays treated with ethidium homodimer were used to visualize the cell death associated with plaques. Ethidium homodimer (EthD-1) is an agent that yields a bright red fluorescence upon binding to the exposed nucleic acids of dead or damaged cells and is routinely used in assessments of cytotoxicity. Under red fluorescent illumination, VSV plaques were easily identifiable due to the greatly increased density of dead cells. Analysis of the cytotoxic areas associated with VSV plaques indicated that the relative size of the regions of enhanced cell death closely mirrored the GFP fluorescent plaque size in all four of the cancer cell lines tested (FIG. 4). Cytotoxic area measurements were collected and normalized as in FIG. 3. Unless otherwise indicated, all cytoxic areas differed significantly (p<0.05) in size from the corresponding VSV-G/GFP cytotoxic areas, with no statistically significant difference indicated by ns. Thus, VSV-rp30 not only propagates more quickly than VSV-G/GFP, overall, it yields a greater oncolytic effect than VSV-G/GFP as well. Additionally, VSV-M51/CT9 and VSV-PGFP both yielded less of an oncolytic effect than VSV-G/GFP, consistent with the smaller plaque size attendant to each of these viruses.

Example 4

Genotype of VSV-rp30

Materials and Methods

*VSV Genome Sequencing*

Viral genomic RNA was extracted from VSV-G/GFP and VSV-rp30 using the QIAamp Viral RNA Mini Kit (Qiagen, Valencia, Calif.). Reverse transcription of isolated VSV genomic RNA was performed using Thermo-X Reverse Transcriptase (Invitrogen, Carlsbad, Calif.) at a reaction temperature of 53.9° C. and an RT-oligo with the sequence, 5'-ACG AAG ACA AAC AAA CCA TTA TTA TC-3' (SEQ ID NO: 11) designed to anneal to the initial 26 bases of the 3'-end of the VSV genome. Full-length genomic VSV cDNA (13.5 kb) was then used as template in a series of 6 PCR reactions that generated overlapping products covering the entire genome and ranging in size from 2.0-2.7 kb. Primers were designed on the basis of the VSV-G/GFP sequence, SEQ ID NO: 1 (Genbank accession FJ478454). The primers, annealing temperatures and product sizes for these reactions were as follows. PCR 1: 1F=RT-oligo shown above (SEQ ID NO: 11), 1R 5'-GAT ATG GTG AGA GGC TGA AGA (SEQ ID NO: 12) 54.2° C.; 2054 bp. PCR 2: 2F 5'-CCA GTG ATG AAC ACA CAT CC-3' (SEQ ID NO: 13), 2R 5'-AGT CTC GAG CGT GAT ATC TGT TAG-3' (SEQ ID NO: 14); 54.3° C.; 2726 bp. PCR 3: 3F 5'-CTC AAA TCC TGC TAG GTA TG-3' (SEQ ID NO: 15), 3R 5'-GAC TTC CAT GAT TGC TGT TAG-3' (SEQ ID NO: 16); 54.2° C.; 2422 bp. PCR 4: 4F 5'-TTC AAG GAC GAC GAC GGC AAC TAC AAG AC-3' (SEQ ID NO: 17), 4R 5'-ACC CTC TTG TCC TTG CCA AC-3' (SEQ ID NO: 18); 54.3° C.; 2559 bp. PCR 5: 5F 5'-CTT AAT CGA GAG AAC TCA TG-3' (SEQ ID NO: 19), 5R 5'-GAT CTG TTT TAT CTC TTG TC-3' (SEQ ID NO: 20); 50.4° C.; 2131 bp. PCR 6: 6F 5'-GAC TCA AGT ATG GAC TAC AC-3' (SEQ ID NO: 21) 6R 5'-ACG AAG ACC ACA AAA CCA G-3' (SEQ ID NO: 22); 50.4° C.; 2496 bp. All PCR was performed using the Expand High Fidelity PCR Kit (Roche Diagnostics, Indianapolis, Ind.) and the reaction products were purified using the QiAquick PCR Purification Kit (Qiagen). Samples from all reactions were run on 0.8% agarose gels to confirm the presence of a single product of the appropriate molecular weight. Purified products were spectrophotometrically quantified, mixed with the appropriate sequencing primers and submitted to the W. M. Keck DNA Sequencing Facility (Yale University) for automated DNA sequencing. Sequencing of each PCR product was performed on both the sense and antisense DNA strands using the following primers. PCR 1: 1F (shown above, SEQ ID NO: 11), 960F 5'-AAA ACC CTG CCT TCC ACT TC-3' (SEQ ID NO: 23), 1040R 5'-CAA ACC TGC TGT AGT AAG AG-3' (SEQ ID NO: 24), 1R (shown above, SEQ ID NO: 12). PCR 2: 2F, (as shown above, SEQ ID NO: 13), 2962F 5'-CTA GTC TAA CTT CTA GCT TCT G-3' (SEQ ID NO: 25), 3959F 5'-TTC AGG ACG TTG AGA GGA TC-3' (SEQ ID NO: 26), 3047R 5'-AAC AGA TCG ATC TCT GTT AG-3' (SEQ ID NO: 27), 4026R 5'-GGA GCA AGA TAG CTG AGA TC-3' (SEQ ID NO: 28), 2R (shown above, SEQ ID NO: 14) PCR 3: 3F (shown above, SEQ ID NO: 15), 4971F 5'-TTC CAT CCG ATC CTT CAC TC-3' (SEQ ID NO: 29), 569IF 5'-ATT CAA GAC GCT GCT TCG CAA C-3' (SEQ ID NO: 30), 6035R 5'-GAG CTT TTC CAA CTA CTG AAC-3' (SEQ ID NO: 31), 3R, (SEQ ID NO: 16). PCR 4: 4F (shown above, SEQ ID NO: 17), 6974F 5'-GTG ATA CCA TGC TCA AAG AG-3' (SEQ ID NO: 32), 7960F 5'-CCT TTA GTC CCA CAA TTC C-3' (SEQ ID NO: 33) 8046R 5'-GAT CCA CTG TTT TCA CAC TC-3' (SEQ ID NO: 34), 4R (shown above, SEQ ID NO: 18). PCR 5: 5F (shown above, SEQ ID NO: 19), 9931F 5'-CGA ACT TGT TAA AGA CTG AGG-3' (SEQ ID NO: 35), 10038R 5'-GGA ACA GAG GAT TTA TTG AC-3' (SEQ ID NO: 36), 5R, (shown above, SEQ ID NO: 20). PCR 6: 6F (shown above, SEQ ID NO: 21), 11959F 5'-GAA TCA GGT TGG GCC AAT TAC-3' (SEQ ID NO: 37) 12024R 5'-AGC CGT CTC CAC AAC TCA AG-3' (SEQ ID NO: 38), 13045R 5'-CAC TTC TGC TTG TAT CCT CC-3' (SEQ ID NO: 39), 6R, (shown above, SEQ ID NO: 22). All oligonucleotides were synthesized by the Department of Pathology Oligonucleotide Synthesis Facility (Yale University School of Medicine). Inspection of sequence chromatographic data was performed using 4Peaks Version 1.6 software (Mek&Tosj.com) and base-call files were assembled and analyzed using DNA Strider Version 1.3fl4 software (Ch. Marek, Cedex, France). In general, any sequencing ambiguities that arose in one strand were easily resolved by inspection of sequence results from the complementary strand.

*VSV-rp30 Mutation Analysis with BsrD1*

Restriction digestions using BsrD1 (New England Biolabs, Beverly, Mass.) were performed on a 2.1 kb PCR product encompassing the site of the C1772T mutation identified in the gene for the P protein of VSV-rp30. This mutation creates a unique BsrD1 restriction site in the VSV-rp30 PCR product that is not present in the VSV-G/GFP product, and when cleaved, yields two smaller species of 1298 bp and 828 bp. The 2126 bp PCR product was amplified from VSV-G/GFP and VSV-rp30 cDNA using the same methods as described above and primers 960F and 3047R at an annealing temperature of 52° C. for 30 cycles. Products were purified and quantified as described above and 350 ng of each were included in restriction digestion reactions and control reactions (no enzyme) and incubated according to the manufacturer's instructions. Digestion products were run on 1.2% agarose gels stained with ethidium bromide.

Results

Figures 5A, 5B, 5C:
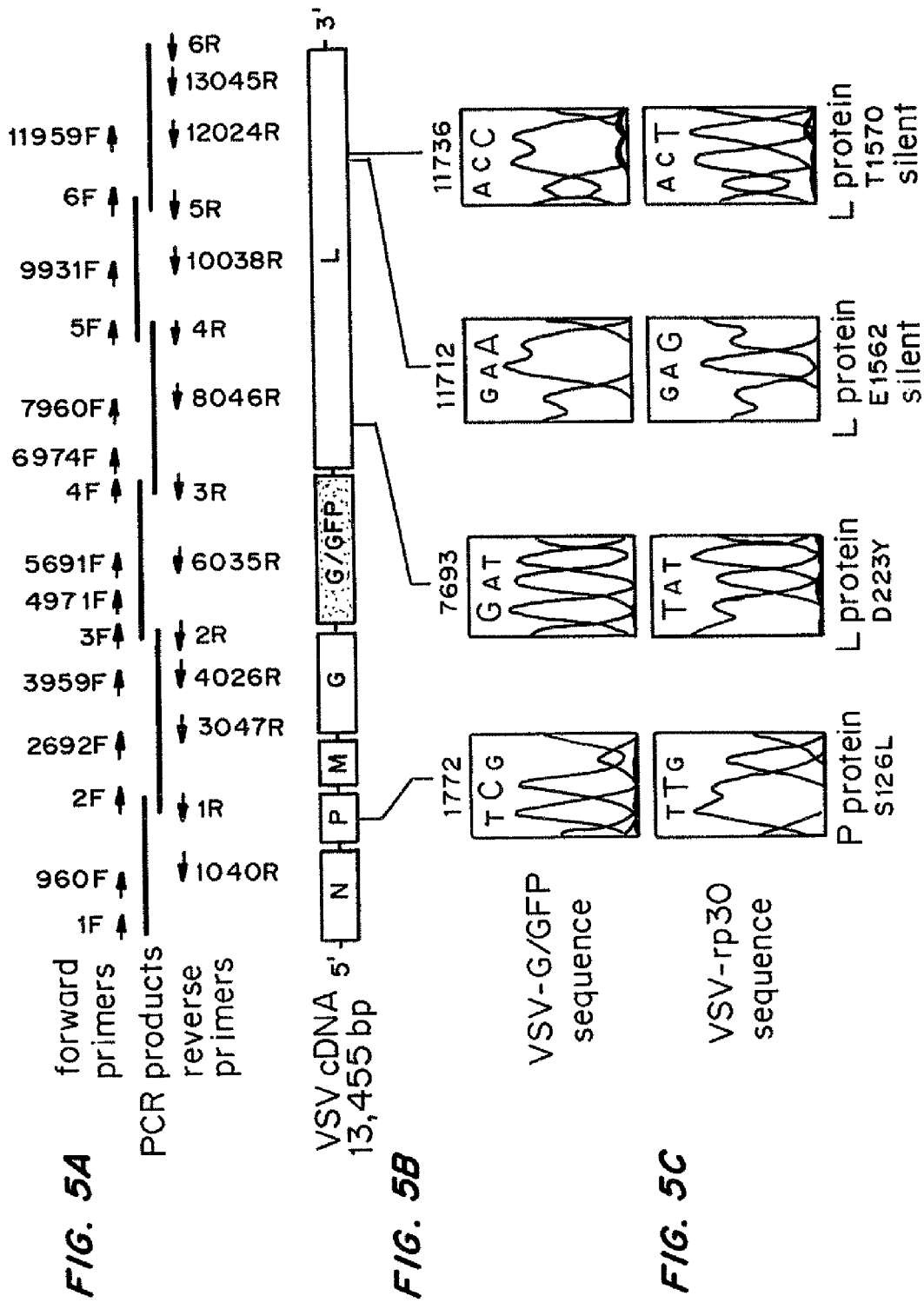
FIG. 5A is a diagram depicting the series of six overlapping PCR products derived from the amplification of the VSV genomic cDNA and used for sequencing. Sequencing primers are illustrated with arrows.
FIG. 5B is a schematic of the parent VSV-G/GFP genome, and illustrates the positions of the four mutations (C1772T, G7693T, A11712G, C11736) identified in the variant VSV-rp30.
FIG. 5C is a section of the sequencing chromatographs of both the parent, VSV-G/GFP (top) and mutated VSV-rp30 (bottom) codons.

The genotypic alterations were identified by sequencing the genomes of the parent VSV-G/GFP and glioblastoma cell-adapted VSV-rp30 viruses using RT-PCR and automated nucleotide sequencing (FIGS. 5A-C). Sequencing of the parent virus as a control showed an identical nucleotide sequence to that used in generating the virus, showing that the parent VSV had population stability, at least over the estimated minimum of 50 generations of viral progeny from the stock previously generated. The sequences of both viruses were found to be identical except for four point mutations located in the genes for the P protein (C1772T) and L protein (G7693T, A11712G, and C11736T) with nucleotide numbering according to SEQ ID NO: 1 (Genbank accession FJ478454)) (FIG. 5 A-C). The P and L proteins of VSV form an RNA polymerase complex that is responsible for both viral mRNA transcription and genome replication. Whereas the P protein itself has not been found to display enzymatic activity, it is believed to modulate L protein activity, with phosphorylation of serine and threonine residues located on P being important for this function.

Inspection of the sequence chromatograph data indicated that all of the detected VSV-rp30 mutations were represented by a single unambiguous chromatographic peak (FIG. 5C), suggesting that these mutations were present throughout the entire VSV-rp30 viral population. Since the C1772T mutation in SEQ ID NO: 1 results in the creation of a Bsr DI restriction site in VSV-rp30, the apparent homogeneity of this mutation within the viral population was determined by means of restriction digestion. Using a 2.1 kb PCR product encompassing the CI772T mutation site, Bsr DI application yielded a complete digestion of the VSV-rp30 amplified PCR product and no detectable digestion of VSV-G/GFP derived product.

Thus, there appears to be no detectable 'residual' parent VSV-G/GFP present in the VSV-rp30 population. Taken together these results indicate an absence of any detectable sequence heterogeneity within the VSV-rp30 population at the identified mutation sites.

The A117120 and C117361 mutations in SEQ ID NO: 1 were both found to be silent base substitutions appearing in the third position of codons 1562 and 1570 of the amino acid sequence of the L protein (SEQ ID NO: 5), respectively. Additionally, these silent mutations appear to be relatively comparable substitutions with respect to human codon usage frequencies (1562: GAA=29.0 vs GAG=39.6 per thousand codons and 1570: ACC=18.9 vs ACT=13.1 per thousand codons) (Codon Usage Database [http://www.kazusa.orjp/codon/]). Not only are both mutations silent, but they also result in comparable substitutions with respect to codon usage frequency. Thus, it is possible, but less likely that these mutations play a significant role in the enhanced oncolytic phenotype displayed by VSV-rp30.

The C1772T mutation of SEQ ID NO: 1 appears in the second position of codon 126 of the P protein and results in a replacement of the serine (S) in VSV-G/GFP (SEQ ID NO: 3) with a leucine (L) in VSV-rp30 (S126L) (SEQ ID NO: 8). A Genbank search (October 2008 [http://www.ncbi.nlm.nih.gov]) indicated that a number of Indiana serotype VSV strains have been identified that, like VSV-rp30, possess a leucine (L) at position 126 of the P protein, (SEQ ID NO: 8). These include strain 85CLB South America, strain 94GUB Central America, strain 98COE North America, strain Glasgow, and strain Mudd-Summers, with the P protein sequences of these strains available using Genbank accession numbers Q8B0H8, Q8B0H3, Q8B0I3, P04879, and P04880, respectively. The only Indiana serotype VSV strain found to possess a serine (S) at position 126 of the P protein, was the San Juan strain (Genbank accession P03520), the same strain from which VSV-G/GFP was originally recombinantly engineered (Lawson 1995). Thus, among the various strains of VSV that have been sequenced and are available on Genbank, the serine (S) at position 126 of the P protein (SEQ ID NO: 3) does not appear to be a residue that is strictly conserved. The oncolytic activity of the San Juan strain relative to the other Indiana serotype VSV strains is unknown.

The G7693T mutation of SEQ ID NO: 1 appears in the first position of codon 223 of the L protein and results in a replacement of the aspartic acid (D) in VSV-G/GFP (SEQ ID NO: 5) with a tyrosine (Y) in VSV-rp30 (D223Y) (SEQ ID NO: 10). A Genbank search (October 2008) indicated that the aspartic acid (D) at position 223 of the L protein (SEQ ID NO: 5) appears to be a highly conserved residue and is present among all the Indiana serotype VSV strains for which sequence data are available. Thus, the presence of a tyrosine (Y) at this site has not been previously reported and is apparently unique to VSV-rp30 (SEQ ID NO: 10).

Example 5

C1772T (S126L) and G7693T (D223Y) Mutations are Possible Targets for Cellular Kinases Both serine and tyrosine can act as potential phosphorylation sites for cellular kinases. Both VSV-rp30a amino acid alterations involved either a serine or a tyrosine. Phosphorylation events that target these sites may be one basis for the novel phenotype observed in VSV-rp30, specifically the loss of the serine at 126, (SEQ ID NO: 8) and the gain of the tyrosine at 223, (SEQ ID NO: 10), could remove and create, respectively serine and tyrosine kinase phosphorylation sites.

In order to investigate what (if any) serine or tyrosine kinases might recognize either of these mutated sites both the mutant and the wild-type P protein and L protein amino acid sequences were downloaded onto two bioinformatics servers located at the Center for Biological Sequence Analysis (CBS) at the Technical University of Denmark (www.cbs.dtu.dk). The first server (NetPhos 2.0) is a database that predicts the likelihood that any particular serine, threonine or tyrosine in a protein sequence is a target of phosphorylation. The second server (NetPhosK 1.0) makes predictions as to what specific kinases would be likely to recognize these sites. These servers indicated the following with respect to the mutant VSV-rp30 sites.

S126L in the P Protein

The serine that is lost at position 126 of the P protein in VSV-rp30 (SEQ ID NO: 8) is predicted to have a very high likelihood of acting as a substrate for phosphorylation and displayed a score of 0.997. Two kinases were predicted to recognize this site, i.e. cdk5 and RSK. Cdk5 is a cyclin-dependent kinase that is specific to neurons and has an axonal subcellular localization. The serines at positions 60 and 64 were predicted to be phosphorylation sites and displayed scores of 0.985 and 0.989, respectively. The sites at 60 and 64 were predicted to be recognized by casein kinase 2 (CK2), the kinase that has been empirically identified as the kinase responsible for phosphorylating these sites in VSV.

D223Y in the L Protein

The tyrosine that is gained at position 223 of the L protein in VSV-rp30 (SEQ ID NO: 10) is predicted to be phosphorylated with a score of 0.665. Three kinases were predicted to recognize this site, i.e. EGFR, Src and INSR. The EGFR kinase prediction is of particular interest since this kinase (epidermal growth factor receptor kinase) is one that has been found to be highly upregulated in glioblastomas. In fact, this particular kinase has emerged as a therapeutic target for the treatment of glioblastomas and a number of EGFR kinase inhibitors are currently undergoing clinical trials.

Example 6

Kinase Inhibitors Reduce VSV-rp30 Efficacy

Materials and Methods

Kinase Inhibitor Assay

The kinase inhibitors staurosporine, genistein and tyrphostin 51 were obtained from Sigma-Aldrich, St. Louis, Mo. (catalog numbers: 54400, G6649 and T7665, respectively) and used to prepare 3 mM, 100 mM and 100 mM stock solutions, respectively, in 100% DMSO. Stock solutions were aliquotted and stored in a lightproof container at −20° C. until use. Confluent U-373 cell monolayers in six-well plates were grown as described earlier. Thirty minutes prior to the start of the experiment, the cell monolayers were aspirated and washed once with 2 mls of PBS before replacing the media with 0.9 ml of low-serum MEM media (1% FBS).

Monolayers were then inoculated with either VSV-G/GFP or VSV-rp30 at a dilution selected to yield approximately 150 plaques per well and overlaid with 2 ml of agarose in low-serum MEM media as described earlier. After solidification of the agarose, a 0.5 ml volume of low-serum MEM media containing kinase inhibitor or vehicle (DMSO) at 5× the final concentration was overlaid onto the agarose. Plates were incubated at 37° C. in 5% $CO_2$ for 24 hrs and 30 plaques from each condition were randomly selected, fluorescently visualized, measured and statistically compared as described earlier.

The individual doses of each kinase inhibitor were prepared by first serially diluting the kinase inhibitor stock solution in DMSO, then adding a constant volume of inhibitor/DMSO solution or DMSO alone (vehicle) to the 0.5 ml volume of low-serum MEM media. In this manner, all conditions were exposed to the same concentration of vehicle, i.e. 0.03% DMSO in the genistein experiments and 0.01% DMSO in the staurosporine and tyrphostin 51 experiments.
Results An essential step in the replication cycle of VSV is the phosphorylation of the P protein by protein kinases expressed by the host cell (Batik and Banerjee, *Proc. Nat. Acad. Sci. USA* 89: 6570-6574 (1992); Das and Pattnaik, *J. Virol.*, 78: 6420-6430 (2004); Lenard, *Pharmacol. Ther.*, 83: 39-48 (1999). Additionally, a wide range of cancer cells have been shown to display aberrant protein phosphorylation activity and a variety of oncogenic mutations have been identified in kinase and phosphatase genes (Bardelli et al., *Science*, 300: 949 (2003); Parsons et al., *Nature*, 436: 792 (2005); Wang et al., *Science*, 304: 1164-1166 (2004). In order to investigate whether host cell phosphorylation activity might play a role in the enhanced propagation of VSV-rp30, three different kinase inhibitors (staurosporine, genistein and tyrphostin 51) were selected their effects on VSV-rp30 and VSV-G/GFP propagation in U-373MG cells using the plaque size assay (described earlier) were examined (FIG. 6 A-C). Staurosporine is a broad-spectrum inhibitor of serine, threonine, and tyrosine kinases. Staurosporine caused a significant attenuation of the difference in plaque size between VSV-rp30 and VSV-G/GFP at concentrations of 10 nM and 100 nM (FIG. 6 A). Genistein is a protein kinase inhibitor selective for tyrosine kinases (Akiyama et al., J. Biol. Chem., 262: 5592-5595 (1987). Genistein also significantly attenuated the difference in plaque size between VSV-rp30 and VSV-G/GFP at a concentration of 10 µM (FIG. 6 B). Finally, tyrphostin 51 is a tyrosine kinase inhibitor selective for the epidermal growth factor receptor tyrosine kinase (EGFR). In contrast to the effects of both staurosporine and genistein, tyrphostin 51 had no significant effect on the difference in plaque size between VSV-rp30 and VSV-G/GFP at concentrations up to 10 µM, the highest dose tested (FIG. 6C).

Figure 6A:
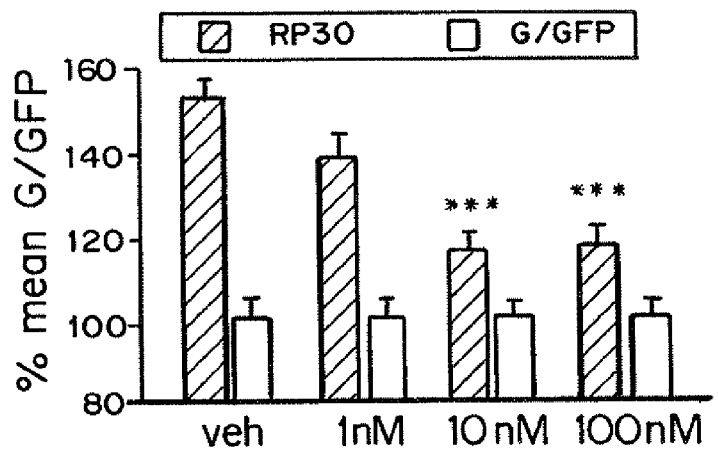
FIGS. 6A, 6B, and 6C are bar graphs illustrating the average plaque diameters (%) of VSV-rp30 plaques (hatched bars) relative to VSV-G/GFP plaques (open bars) on U-373MG cell monolayers after treatment of increasing concentrations (left to right), of different kinase inhibitors: (6A) Staurosporine (nM), (6B) Genistein (μM), and (6C) Tyrphostin 51 (μM).
Figure 6B:
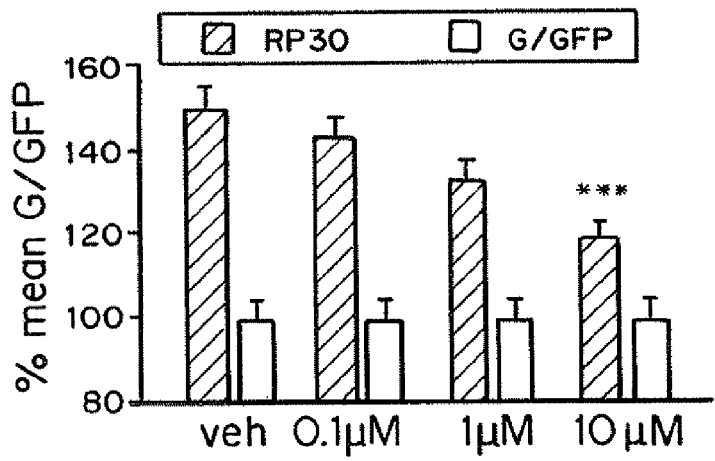
Figure 6C:
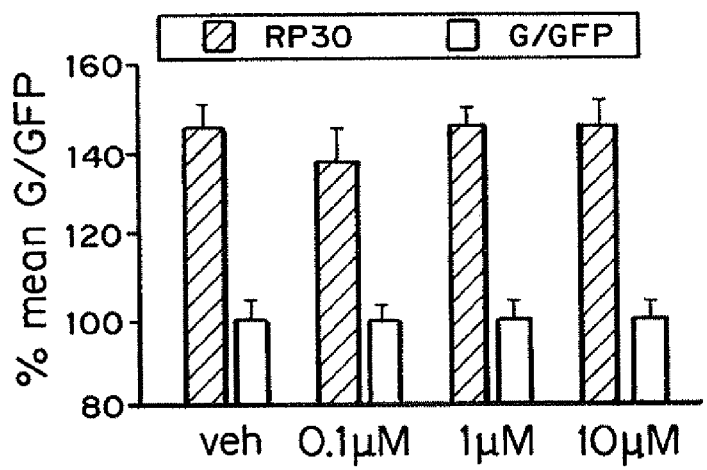

The wide-spectrum kinase inhibitors staurosporine and genistein both produced an attenuation of the enhanced replication of VSV-rp30 relative to VSV-G/GFP, whereas tyrphostin 51, an inhibitor specific to the epidermal growth factor receptor tyrosine kinase (EGFR), did not (FIGS. 6A-C). Taken together, these results suggest that the enhanced propagation (i.e. enhanced rate of infection) of VSV-rp30 relative to VSV-G/GFP in cancer cells may be due, in part, to the activity of one or more cellular kinases sensitive to staurosporine and genistein.

Example 7

Tumor Cells Stably Transfected with Red Fluorescent Protein Gene Reliably Form Tumors Materials and Methods
Transfection For stable transfection, RFP [tetrameric phosphorylated Discosoma red (pDsRed1)-N1 and monomeric pDsRedmonomer-C1], cyan fluorescent protein [phosphorylated cytomegalovirus (pCMV)-CFP], and blue fluorescent protein (pCMV-BFP) plasmids were used. pCMV-CFP and pCMV-BFP were generated by exchanging the RFP expression cassette from pDsRed monomer-C1 with CFP or BFP cassettes from pRSET/CFP (Invitrogen). Cells were transfected using Lipofectamine 2000 reagent (Invitrogen), enriched, and maintained with G418 (Sigma, St. Louis, Mo.). rU87 and rU118 cells were sorted for brightest fluorescence on a FACSvantage SE fluorescence-activated cell sorter (BD Biosciences, San Jose, Calif.). Growth characteristics were assessed using 3-(4,5-dimethylthiazol-2-yl)-2,5-diphenyl tetrazolium bromide (MTT) (Invitrogen) assay according to the instructions of the manufacturer. Optical density was read at 570 nm using a Dynatech (Alexandria, Va.) MR500 ELISA plate reader and corrected from background control.
Results To choose the optimum nontoxic fluorescent protein that would allow simultaneous imaging with GFP encoding virus, several different fluorescent proteins, including cyan (pCMV-CFP), blue (pCMV-BFP), and red (tetrameric pDsRed1-N1 and monomeric pDsRedmonomer-C1) were tested. BFP was subject to quick photobleaching, and CFP was not practical for use simultaneously with GFP-expressing VSV because of overlap in their fluorescent spectrum. Transfection of U87 high-grade glioma cells with tetrameric RFP resulted in toxicity in vitro. Stable transfection of U87MG or U118MG glioma cells with a plasmid encoding the monomeric DsRed protein resulted in bright red fluorescence and did not alter growth characteristics as demonstrated by MTT assay. Over a 24 h period, absorbance measurements increased by 89.8±33.2% in rU87 cells and by 103.8±32.5% in U87MG cells (statistically nonsignificant p=0.75, n=6, Student's t test), indicating that the red glioma cells were replicating at their usual rate. After selection in G418 and fluorescence-activated cell sorting, all tumor cells expressed red fluorescent protein. Bilateral brain injections of either rU87 or rU118 cells in SCID or nude mice yielded tumors in 100% (90 of 90) of injections. Ten days after injection, noninfected rU87 xenografts in SCID mice had a mean calculated volume of 7.13±5.76 mm3 (n=4; calculated as ellipsoid volume: 4/3 x y z). Horizontal and vertical radi x and y represent half of the horizontal and vertical diameters in the coronal section that harbored the largest tumor cross-section area. The anteroposterior radius z represents half the tumor craniocaudal length, calculated by multiplying section thickness with the number of sections where the tumor is present. Tumor xenografts grew predominantly by expansion, although in a number of cases tumor cells separated from the main tumor body and invading the surrounding parenchyma. Tumors grew with no spontaneous regression or hemorrhage until they reached a lethal size. For humane reasons, mice were killed at the onset of symptoms before tumor induced death.

Example 8

Intravenously Injected VSVrp30a Targets Multifocal Brain Tumors with High Selectivity Materials and Methods
Mouse Procedures Animal experiments and postoperative care were performed in accordance with institutional guidelines of the Yale University Animal Care and Use Committee. Immunodeficient homozygous CB17-SCID (CB17SC-M) and NCr-Nude mice (NCr-Foxn1nu) at an age of 4-5 weeks were obtained from Taconic Farms (Germantown, N.Y.). Animals were stereotactically grafted with $3\times10^5$ tumor cells bilaterally into the striatum (2 mmlateral, 0.4 mmrostral to bregma at 3 mmdepth) or cortex or with $1\times10^5$ cells unilaterally in the left olfactory bulb (0.75 mm lateral, 4.5 mm rostral to bregma at 1.5 mm depth). For cranial window experiments, a teardrop-shaped skin flap (with an anteroposterior axis along the parasagittal plane crossing the midpupillary line) was removed, and a 5-mm-wide round craniectomy was drilled under an operating microscope (Zeiss, Oberkochen, Germany). rU87 glioma cells, $5 \times 10^4$, were injected along a trajectory parallel to the cortex immediately below the pia mater. The craniotomy was covered with a round glass coverslip of 8 mm diameter and glued to the bone margins using cyanoacrylate. Animals were followed with daily measurements of weight, food and water consumption, and overall health and activity, and the cranial window animals were given parenteral antibiotics. During in vivo brain imaging, mice were lightly anesthetized to reduce movement, and the head was maintained in a horizontal position during image acquisition. Animals were killed with a pentobarbital overdose and perfused transcardially with 4% paraformaldehyde. For determination of blood-brain barrier integrity, 2% Evans Blue (Sigma) in 100 µl of sterile saline was injected intravenously 1 h before the animals were killed.

Viruses

Ten days after tumor grafting, 100 µl of medium containing virus ($10^7$ plaque forming units (PFU) of VSVrp30a, VSV-GFP, VSV-ΔG-GFP, or recombinant pseudorabies virus (PRV)-GFP or $10^{12}$ virions adeno-associated virus serotype 2 (AAV)-GFP was injected through the tail vein. VSV-GFP and VSV-ΔG-GFP were generously provided by Dr. J. K. Rose (Yale University). PRV-GFP strain 152 was kindly provided by Dr. L. W. Enquist (Princeton University, Princeton, N.J.) (Smith et al., *Proc Natl Acad Sci*, 97:9264-9269 (2000)) and AAV-GFP was kindly provided by Dr. K. R. Clark (Ohio State University, Columbus, Ohio). Details on the generation and characteristics of the tumor-adapted VSV-GFP isolate VSVrp30a were described previously (Wollmann et al, *J. Virol.*, 79(10): 6005-6022 (2005)). VSV, PRV, and AAV were all shown to infect glioma cells previously.

Results

It was shown that in animals bearing two subcutaneous tumors, intratumoral VSV injection into one tumor resulted in selective infection also in the second tumor on the contralateral side of the body. This strongly suggested vascular viral dissemination and led to the hypothesis that VSV could be delivered to brain tumors through the intravascular route. However, entry into brain tumors is more complex than elsewhere in the body because the blood-brain barrier can be a major obstacle, even for relatively small-sized chemical or biological agents (Pardridge, *Neuron*, 36:555-558 (2002)). The ability of intravenously administered VSV to target intracranial tumor xenografts was tested. In mice that were implanted with bilateral brain rU87 xenografts (n=9 animals, 18 tumors), intravenous injection of $10^7$ PFU of VSVrp30a through the tail vein consistently resulted in infection of the intracranial tumors. A single injection was sufficient to infect gliomas. After an injection of $10^7$ PFU, VSVrp30a infection was found in different regions inside the tumor, suggesting multiple sites of virus seeding. Infection inside the tumor started with a time lag after intravenous delivery but was found in all tumors analyzed after 24 h.

Example 9

VSVrp30a Replicates and Spreads within the Tumor Mass

Materials and Methods

VSV is a replication-competent virus and spreads within the tumor. Early in the course of infection in the non-infected areas, red tumor cells with intact cellular outlines were seen. Within the VSV-infected area, infected and dead tumor cells and debris were surrounded by VSV-infected cells with membranous GFP staining. The presence of newly infected cells at the boundary between killed and non-infected cells suggests that VSV spreads within the tumor. To document viral spread within the tumor mass, animals were killed 24, 48, and 72 h post-inoculation (HPI).

Results

Analyzing animals at different time points within the course of VSV infection and using serial histological sections through the tumor, it was found that the virus had spread from initially infected foci to encompass the whole tumor. In addition to the widespread infection and tumor cell killing inside the main tumor mass, tumor cells that were migrating into the normal brain at the tumor margin were also infected, with remarkable sparing of neighboring normal brain cells in immediate contact with the tumor. There was a remarkably high degree of selective infection of the brain tumors with relatively little infection of the surrounding normal brain; the ratio of infected tumor cells to infected normal brain cells was 10,000:1, or better.

Although most tumor xenografts grew by expansion, some isolated cell clusters of tumor cells remote from the main tumor bulk were observed. Of note, these distant cell conglomerates were also targeted by VSV. The course of VSV oncolysis in the brain is schematized in FIG. 7. The results demonstrated a continuously increasing area of infection in the tumor mass, resulting in tumor cell death, as indicated by the loss of cellular integrity and the appearance of small granular debris after viral infection. Six tumors were used for analysis of VSV and four for VSVrp30a infection at each time point. In animals killed early in the course of infection, areas of infected and killed tumor cells surrounded by other cells that appeared live at the time of death but with early signs of infection and expression of viral reporter gene were documented. Intact cellular outlines and homogeneous intracellular DsRed signal were used to distinguish healthy cells from dead or dying cells. In addition, DAPI counterstain showed nuclear breakdown commonly found in dead cells, and areas of dead cells showed small granular debris in the place of intact cells. The mean infected area in coronal brain sections with the largest tumor diameter increased from approximately 50 to 60% at 1 d post-inoculation (DPI) to what appeared to be infection of almost the entire tumor by 3 DPI (FIG. 8). As shown in the fractionated bar graph in FIG. 8, the proportion of viable tumor cells showing normal cellular and nuclear morphology decreased simultaneously.

Finally, the spread of infection was documented in real time using the cranial window animal model. In vitro, VSVrp30a was more effective at selective destruction of gliomas than the parental VSV-GFP. To determine whether this difference persisted in vivo, the relative abilities of the two VSVs to infect gliomas in the mouse brain were compared using the same concentration of virus inoculum. Both VSVrp30a (n=9 animals, 18 tumors) and VSV-GFP (n=9 animals, 18 tumors) successfully targeted the brain tumors after tail vein inoculation VSV-GFP. A high tumor selectivity of VSV infection was observed during the time period of our study. In animals implanted with multiple tumors, all brain tumors were infected simultaneously. VSV infection and resultant oncolysis were observed in all tumor masses regardless of the size and location.

Small and large tumors were infected at different localizations in the brain whether striatal, cortical, subventricular, or within the olfactory bulb. Tumors in the brain and periphery were also simultaneously infected (see below). In animals killed within the first 72 HPI, when the entire tumor mass was infected by VSVrp30a, no GFP expression in the brain parenchyma surrounding the tumor, choroids plexus, or in the leptomeninges was observed. After this period of high tumor-specific infection (72-96 HPI in our model), when the whole tumor bulk showed marked cytopathy, select periventricular groups of infected neurons and ependymal cells in immunodeficient mice were observed.

Example 10

VSVrp30a Infection Causes Tumor Cell Death

Materials and Methods
Immunocytochemistry
Cryosections were mounted and counterstained with 4,6-diamidino-2-phenylindole (DAPI) (Invitrogen). For cleaved caspase 3 immunocytochemistry, 20 µm sections were incubated with a 1:150 dilution of polyclonal rabbit cleaved caspase 3 antiserum (Cell Signaling Technology, Danvers, Mass.), followed by detection with a 1:200 dilution of biotinylated anti-rabbit antibody (Invitrogen) and ABC reagents detected with diaminobenzidine and hydrogen peroxide (Vector Laboratories, Burlingame, Calif.). For von Willebrand factor staining, a 1:500 dilution of polyclonal rabbit antibody (Abeam, Cambridge, Mass.) was used following the same procedure outlined above.
Imaging
Histological sections were studied either on an Olympus Optical (Tokyo, Japan) IX71 fluorescent microscope fitted with a SPOT-RT camera (Diagnostic Instruments, Sterling Heights, Mich.) or on an Olympus Optical Fluo-300 laser confocal microscope using Fluoview 300 software version 4.3. Corresponding phase-contrast, green, red, and blue fluorescence photomicrographs were fused and corrected for color and contrast using Adobe Photoshop 7 software (Adobe Systems, San Jose, Calif.). Several high-resolution pictures were used for montage of whole coronal sections.

Figure 9A:
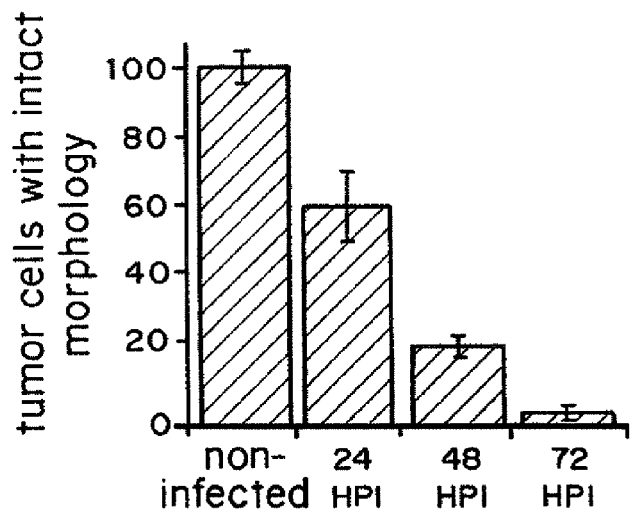
FIG. 9A is a bar graph illustrating the number of tumor cells with intact morphology as a function of hours post infection (HPI) with VSV-rp30.
Figure 9B:
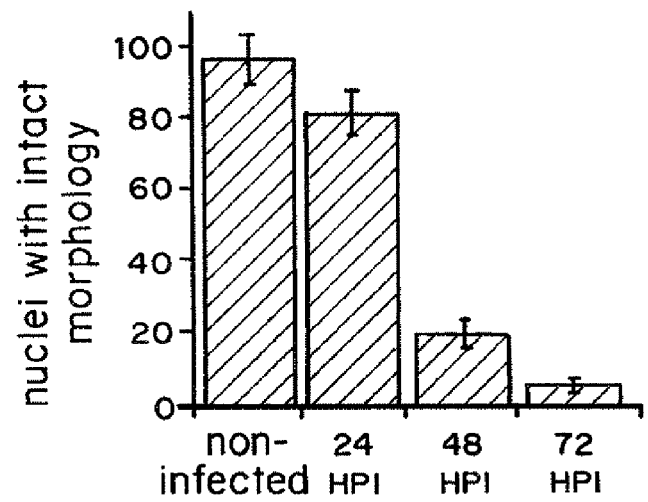
FIG. 9B is a bar graph illustrating the number tumor cell nuclei with intact morphology as a function of hours post infection (HPI) with VSV-rp30.
Figure 9C:
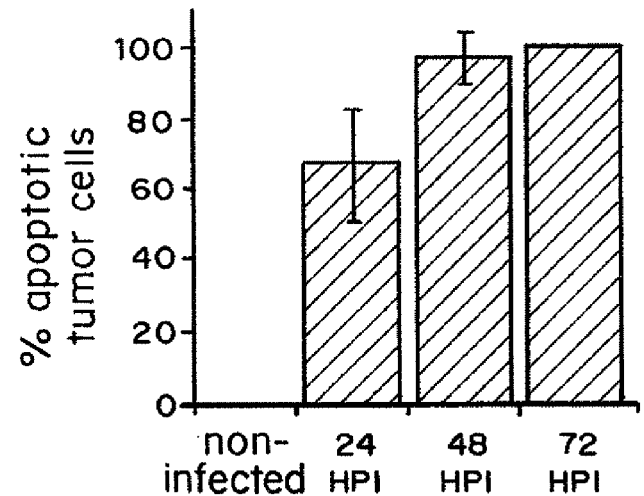
FIG. 9C is a bar graph illustrating the number of apoptotic tumor cells as a function of hours post infection (HPI) with VSV-rp30.

Tumor area calculations and cell and nuclear counting were done using NIH ImageJ software. Animals with cranial windows were imaged daily or more frequently under an Olympus Optical SZXZB12 stereo microscope and Olympus Optical Fluo-300 laser confocal microscope.
Results
VSV infection results in death of tumor cells in vitro. Similarly, VSVrp30a induced widespread tumor cell death in the brain in vivo. Such a fast and efficient elimination of the tumor is important because remaining resistant cells have the potential of repopulating the tumor mass, which is commonly observed in gliomas after conventional treatment. Widespread cell death was detected within the tumor mass. Cell death was indicated by loss of cellular outlines on confocal and light microscopy. Differential interference contrast (DIC) microscopy showed loss of cellular outlines and diffusion of intracellular tumor cell DsRed with fluorescent imaging and nuclear fragmentation assessed with DAPI staining. Infected tumors stained positively for the cellular apoptosis execution protein activated caspase 3. There was a statistically significant decrease in the number of cells with intact cellular ($p=0.0001$, ANOVA test) and nuclear morphology ($p=0.0001$, ANOVA test) and a statistically significant increase in the number of tumor cells immunostained positive for activated caspase 3 ($p=0.0001$, ANOVA test) after infection (FIGS. 9A-C).

Infected tumor cells underwent lysis several hours after expression of viral proteins. An important observation was that the mouse neovasculature and its cellular constituents, including endothelial cells, were not infected, as the intact vessel architecture was visible by DIC microscopy and the positive staining for the endothelial marker von Willebrand factor of these non-infected cells. Blood vessels appeared mostly undamaged even late in infection. After widespread tumor cell lysis, both viral GFP and tumor DsRed intensity decreased in the tumor mass, which can be attributed to loss of cellular integrity and resultant diffusion of intracellular content.

Example 11

Oncolytic Potential of VSVrp30a Generalizes to Human Glioma and Mammary Carcinoma VSVrp30a was adapted to human gliomas by passaging it on U87MG cells for many generations. Therefore, to test the hypothesis that the in vivo oncolytic potential of VSVrp30a was not restricted to the cell line on which it was developed, two other types of tumor implanted into the mouse brain were also tested. One of the cell types was U118MG, a cell line derived from high-grade human glioma but with different genetic anomalies than found in U87MG. The two glioma types have been shown to differ from each other in their p53 status, c-myc, and epidermal growth factor receptor and PDGF (platelet-derived growth factor) receptor overexpression; they share p14, p16 deletion, and low expression of multidrug resistance gene.

U118 cells were stably transfected and sorted using the same protocol used for U87MG cells and will be called rU118 herein. SCID mice bearing rU118 human glioblastoma xenografts (n=12 tumors) were killed 48 and 72 h (six tumors each) after a single intravenous injection of VSVrp30a; widespread selective infection, and apoptotic cell death was noted. There was no significant statistical difference in VSV induction of apoptosis between rU118 tumors and rU87 tumors 72 HPI ($p=0.1855$, Student's t test), suggesting that the virus targeted both types of glioma cells. A mouse mammary carcinoma, the 4T1 cell, was also tested. 4T1 cells were transiently transfected with the monomeric DsRed gene and injected into the brain and periphery 48 h after transfection. 4T1 mouse mammary carcinoma cells were used to create an animal model with simultaneous peripheral and multiple brain tumors to mimic the setting of a disseminated systemic cancer. VSVrp30a infected all cranial and subcutaneous flank grafts in SCID mice (n=2 mice) after a single intravenous injection.

Example 12

IV Delivery of VSV Efficiently Targets and Lyses Brain Xenografts in Nude Mice

Figure 10:
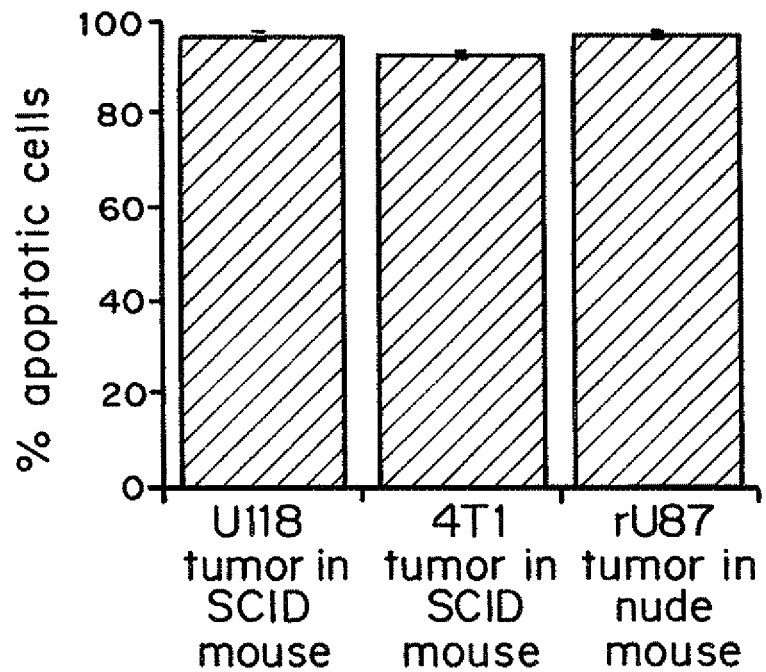
FIG. 10 is a bar graph illustrating virus induced killing as the percent of apoptotic cells in various tumor xenograft models infected with VSV-rp30 by intravenous injection. From left to right bars represent U118 (glioma) tumor in T- and B-deficient SCID mouse, 4T1 (mouse mammary carcinoma) tumor in SCID mouse, and rU87 (glioma) tumor in nude mouse.

Materials and Methods
SCID mice are deficient in both humoral and cellular immune defense. Nude mice, conversely, have an immune defect primarily affecting T-cells. To test whether the less compromised immune status would interfere with tumor targeting, striatal rU87 glioma xenografts were tested in NCr-Nude mice (n=6 tumors).
Results
Tumor xenografts were infected and destroyed with similar efficiency and kinetics in the nude mouse as earlier in the SCID mouse (FIG. 10). At 72 h after virus inoculation, there was no significant difference in dying cells revealed by activated caspase 3 immunostaining between rU87 tumors in SCID animals, rU118 tumors in SCID animals, and rU87 tumors in nude mice ($p=0.085$, ANOVA test) (FIG. 10). All brain tumors were similarly targeted by the virus.

After intravenous injection, selective viral infection was found in all tumors and tumor types, and in both SCID and nude mice on different genetic backgrounds, indicating a high efficiency of VSV-tumor targeting. A notable finding was the demonstration of simultaneous oncolytic infection in both subcutaneous flank and brain tumors in the same animal after a single systemic virus injection. In addition to demonstrating the efficiency of a systemic VSV-based therapy, this finding shows VSV infects widely metastatic cancers. Given the oncolytic activity of VSV against a range of cancer cells with diverse genetic defects (Stojdl et al., *Cancer Cell*, 4:263-275 (2003); Lichty et al., *Trends Mol Med*, 10:210-216 (2004); Barber, *Oncogene*, 24:7710-7719 (2005)), an intravenous injection of VSV can be used to target simultaneously both brain and peripheral metastases of a systemic cancer.

Direct intratumoral injection may be useful for some tumors. To date, such intratumoral injections of viruses have resulted in a very limited viral spread around the injection site (Pulkkanen and Yla-Herttuala, *Mol Ther*, 12:585-598 (2005)). The ability of VSV to infect multiple independent central and peripheral sites and spread in them is substantive, making it possible to treat disseminated disease and even target minute tumor colonies that are otherwise difficult to detect. Xenograft models are limited in that human gliomas often grow expansively rather than infiltratively in mice. Nonetheless, infiltrating cells were observed within the host brain, and these were targeted by VSV.

Example 13

Intranasal VSV Targets Olfactory Bulb Tumors

Materials and Methods

After intranasal inoculation, VSV can enter the CNS. Nasal mucosal infection results in infection of olfactory neurons, and VSV can gain access to the CNS through the olfactory nerve, which projects to the glomeruli in the olfactory bulb (van den Pol et al., *J. Virol*, 76:1309-1327 (2002)). The hypothesis that VSV could enter the brain along the olfactory nerve and target brain tumors in the olfactory bulb was tested. rU87 cells were stereotactically grafted into one of the two olfactory bulbs in SCID mice. Four days after tumor implantation, animals were inoculated in each nostril with 25 µl containing $2.5 \times 10^7$ PFU of VSVrp30a.

Results

VSV was transported to the periphery of both olfactory bulbs after intranasal inoculation and infected the olfactory nerve and the tumor but did not show much infection in deeper parts of the control contralateral bulb lacking tumor. SCID mice with VSV in the olfactory bulb survived VSV infection for 2 weeks. A long survival in this tumor model demonstrated that few tumor cells could be found in the bulb after the viral challenge. In animals killed 3 DPI (four tumors) or 5 DPI (six tumors), VSV infection was located within the tumor but not in the surrounding parenchyma or in the intact contralateral olfactory bulb. In nine additional mice killed 7, 10, 15, 16, or 17 d after virus inoculation, cellular debris indicative of a viral infection was found, but surviving tumor cells were not found, suggesting that the virus was successful in eliminating the tumor.

Although evidence was found of infected olfactory nerve fibers that could serve as entry to the CNS, there is still the possibility that VSV entered the blood circulation through intranasal application and might reach the olfactory bulb via the circulatory system. To address this question, peripheral sentinel tumors were placed into the flank of three animals simultaneously with olfactory tumor grafting. Seven days later, mice received $2.5 \times 10^7$ PFU VSVrp30a into each nostril. At 3 d after inoculation, both olfactory bulb and peripheral tumors were analyzed. No viral infection was found at the remote sentinel tumor, whereas strong GFP expression was evident at the nasal mucosa, olfactory nerve and bulb, and at the olfactory tumor graft, suggesting a direct path of VSVrp30a through the olfactory nerve route. This finding indicates that neural routes of VSV dissemination in brain can be exploited for targeting tumors in specific regions and facilitating of distant tumors or infiltrative tumor cells with minimal infection in normal brain parenchyma.

Example 14

Real-Time Microscopy of VSVrp30a Oncolysis in Cortical Glioma Xenografts

Materials and Methods

To study the kinetics of VSV oncolysis, a time-lapse in situ human brain tumor imaging model was used. rU87 cells were implanted subpially into the SCID mouse cortex (n=3) under a glass coverslip permanently mounted on a parasagittal craniectomy.

Results

Figure 11:
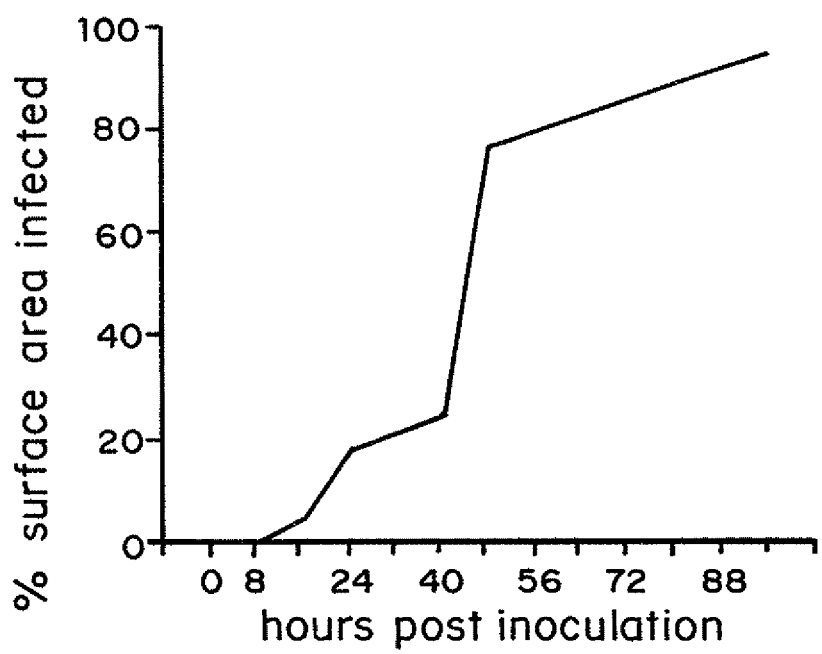
FIG. 11 is a line graph showing the percent surface area infected of glioma tumor in a mouse brain as a function of time following infection with VSV-rp30.
Figure 12A:
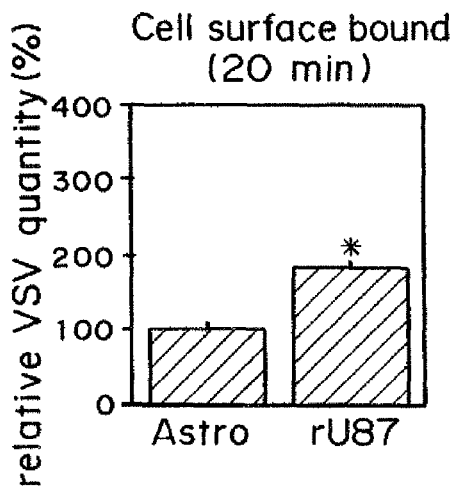
FIG. 12A is a bar graph illustrating the relative VSV quantity (%) cell surface bound to normal human astrocytes (Astro) or rU87 glioma cells 20 min after infection.
Figure 12B:
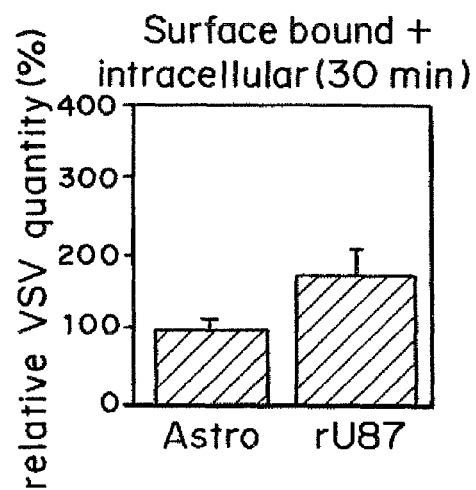
FIG. 12B is a bar graph illustrating the relative VSV quantity (%) cell surface bound and intracellular to/in normal human astrocytes (Astro) or rU87 glioma cells 30 min after infection.
Figure 12C:
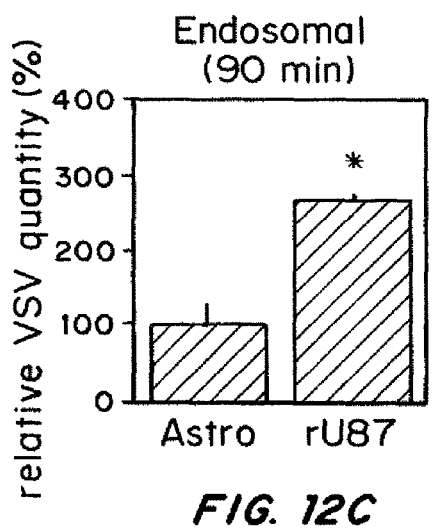
FIG. 12C is a bar graph illustrating the relative VSV quantity (%) in endosomes in normal human astrocytes (Astro) or rU87 glioma cells 90 min after infection.
Figure 12D:
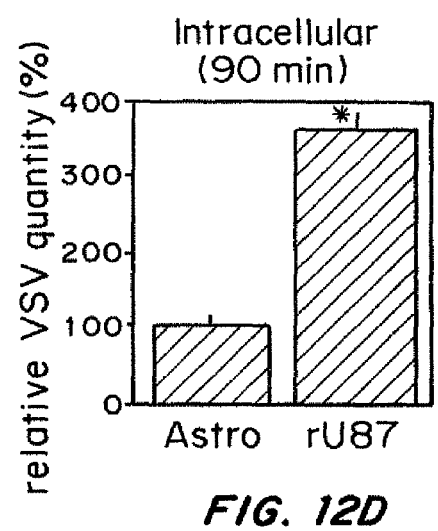
FIG. 12D is a bar graph illustrating the relative VSV quantity (%) in intracellular in normal human astrocytes (Astro) or rU87 glioma cells 90 min after infection.

By imaging tumor cells in the living animal brain using fluorescent and laser confocal microscopy, VSV infection as early as 16 HPI after tail vein injection of $10^7$ PFU of VSVrp30a could be detected (FIG. 11) and followed through viral infection over several days in the live brain. Tumor growth and infection were observed every 4-8 h over a course of 4 d. VSV infection spread through the whole tumor bulk within 96 h (FIG. 11); although multiple points of infection were seen, the majority of tumor cells appeared to be infected by a locally spreading VSV infection. Laser confocal microscopy gave a cellular or even subcellular resolution, making visible not only single cells but also their processes. Using this technique, it was found that VSV infected single infiltrating red tumor cells but not the surrounding normal brain tissue. Vascular patency and circulation appeared normal in tumor vessels within the infected area even at advanced stages of tumor cell lysis; in live real-time imaging, erythrocytes could be seen moving through the uninfected walls of the blood vessels within the tumor even when all surrounding tumor cells were infected and dying.

Example 15

Mechanism of VSV Tumor Targeting

Materials and Methods

The blood-brain barrier may be leaky in some types of tumors. In normal circumstances, VSV does not enter the CNS through the hematogenous route. Therefore, to explore what makes tumor xenografts permeable to VSV, blood-brain barrier integrity was tested in the xenograft neovasculature.

Results

Strong Evans Blue staining was detected within bilateral striatal tumors in SCID (n=4 tumors) and nude mice (n=2 tumors) 1 h after intravenous injection of the dye. On all sections, the Evans Blue stained area completely overlapped with the red tumor mass, indicating a uniform permeability of the tumor to dye. Control experiments were performed to address the effect of needle injury alone on Evans Blue leakage. Evans Blue leakage was observed only immediately after the injury. Ten days after injury, the same time given for tumor formation, no dye leakage could be observed. All brains showed dye leakage in circumventricular areas in which the blood-brain barrier is normally permissive for dye infiltration.

Sterile Needle Injury or Human Astrocyte Transplants do not Get Infected

Materials and Methods

To test the hypothesis that tumor targeting of VSV was not a consequence of nonspecific parenchymal brain damage at the injection site, bilateral sterile stab wounds were done using the same (Hamilton point style 2) needle at the same striatal coordinates (n=4 wounds).

Results

When the same amount of intravenous virus was injected 10 d after this needle injury, no viral GFP was detected within the brain. In parallel, the question of whether the virus targets human cells, or transplanted cells in general, rather than tumor cells specifically, was addressed. When human (n=4 injections) or mouse (n=4 injections) normal astrocytes were transplanted into the same coordinates used for tumor cells, no viral GFP expression was detected in the brain 72 h after intravenous virus injection.

Is Replication Essential for Infection

Materials and Methods

These data demonstrate that VSVrp30a does not enter the brain because of the injury of cell transplantation, nor does it target normal human or mouse cells transplanted into the brain. Infection of glioma xenografts appears specific for replication-competent VSV. To test whether replication was essential for effective tumor targeting, a recombinant replication deficient VSV (VSV-ΔG-GFP) was tested for its capacity to infect intracranial xenografts. This virus can infect cells but, because of the deletion of the VSV-G gene, cannot produce infectious progeny, resulting in only a single cycle of infection.

Results

Intravenous injection of $10^7$ PFUs of VSV-ΔG-GFP to animals with bilateral striatal tumors (n=2) did not result in tumor infection. As a positive control, GFP-expressing scattered cells were detected in the liver after intravenous injection of VSV-ΔG-GFP. To exclude the possibility that targeting of intracranial tumor xenografts by VSV was not the result of nonspecific viral entry, two other viruses that were previously shown to infect or lyse glioma cells in vitro was used. Intravenous injection of a replication-incompetent adenoassociated virus type 2 (AAV-GFP; n=2; 3 DPI) or a replication-competent pseudorabies virus (PRV-GFP; n=2; 2 DPI) did not result in infection of intracranial rU87 xenografts. All three of these viruses were shown previously to infect tumor cells in vitro, and this was reconfirmed in vitro for the stocks used in this study.

Example 16

VSV Binding to the Plasma Membrane and Virus Internalization is Greater in Glioma than in Normal Astrocytes Materials and Methods Virus Binding and Entry Experiments.

Binding, entry, and uncoating of VSVrp30a were compared in rU87 glioma cells and normal human astrocytes using quantitative RT-PCR. To assess membrane-bound fraction, cells were incubated at 4° C. with VSVrp30a for 20 min and washed five times before RNA extraction. To quantify intracellular virus, cells were trypsinized for 10 min and washed five times in PBS. VSV was pooled in the endosomal compartment by incubating for 90 min in the presence of 5 mM ammonium chloride (Sigma). Ammonium chloride blocks acidification of the endosome and therefore blocks viral uncoating into the cytoplasm. These experiments were done in triplicate using an MOI of 10.

Real-Time PCR for Viral GFP

RNA was extracted from cell lysates using RNeasy kit (Qiagen, Valencia, Calif.), and 1 μg of total RNA was reverse transcribed by random hexamer priming using the Super Script III reverse transcriptase kit (Invitrogen). This was followed by quantitative PCR using TaqMan gene expression assays (Applied Biosystems, Foster City, Calif.) for GFP and human glyceraldehyde-3-phosphate dehydrogenase (GAPDH). Primer sequences for GFP were as follows: sense, 5'-GAG CGC ACC ATC TTC TTC AAG-3' (SEQ ID NO: 40); antisense, 5'-TGT CGC CCT CGA ACT TCA G-3' (SEQ ID NO: 41).

Results

These data show that VSV selectively targets glioma in the brain, suggesting that some mechanism underlies the relative selectivity of the virus to the tumor. A correlation exists between VSV infection and various defects in the interferon system in tumor cells (Stojdl et al., *Nat Med,* 6:821-825 (2000); Balachandran et al., *J Virol,* 75:3474-3479 (2001)). A series of five different brain tumor cell lines and normal human control astrocytes was compared previously, and demonstrated an interferon-dependent selectivity of VSV for glial tumor cells over their nontumor counterpart (Wollmann et al., *J Virol,* 81:1479-1491 (2007)). However, antiviral defense may not exclusively account for the selectivity, and several additional mechanisms have been proposed (Wagner and Rose, Philadelphia Raven Press, (1996); Balachandran and Barber, *Cancer Cell,* 5:51-65 (2004); Barber, *Oncogene,* 24:7710-7719 (2005); Lyles and Rupprecht, Lippinscott Williams and Wilkins, 1363-1408 (2007). No specific receptor has been identified for VSV; after binding, the virion undergoes clathrin-mediated endocytosis, and, after acidification in the endosome, the uncoated virus enters the cytoplasm.

To test the hypothesis that VSVrp30a binds and enters tumor cells with a higher efficiency, viral binding and entry in rU87 glioma cells was compared to primary normal adult human astrocytes in vitro using quantitative PCR (FIG. 12). Viral quantity was normalized against cellular GAPDH. In separate quantitative PCR experiments, it was confirmed that GAPDH was expressed at comparable quantities in normal astrocytes and glioma cells. To test for the quantity of VSV that binds to cell surface, cells were incubated with virus at 4° C. After 20 min of incubation, the cells were washed five times with buffered medium before RNA extraction. Compared with human astrocytes, the quantity of cell-bound VSVrp30a at 20 min after infection appeared to be slightly (1.8 times) greater for rU87 glioma cells (statistically significant; p=0.005, n=6, Student's t test) (FIG. 12 A). A somewhat greater viral quantity in rU87 cells was again found when surface-bound plus intracellular VSVrp30a was quantified after a 30 min incubation at an MOI of 10 (p=0.05, n=6, Student's t test) (FIG. 12 B). It was next determined how efficiently the cells internalized VSV. For this purpose, cells were incubated with VSVrp30a at an MOI of 10 for 30 min and next incubated for another 1 h after changing the medium three times to eliminate unbound virus. At 90 min after infection, cells were washed five times with PBS and trypsinized, and intracellular VSV was quantified. Finally, to measure only the endosomal fraction, the same experiment was duplicated in the presence of ammonium chloride, which inhibits viral uncoating from the endosomes. At 90 min after infection, 2.6 times more virus in the endosomes and 3.6 times more virus intracellularly in rU87 cells compared with normal astrocytes (both statistically significant; p=0.001, n=6, and p=0.003, n=6, respectively, Student's t test) (FIG. 12 C, D). These data suggest that VSV binding to the plasma membrane and virus internalization appear to be greater in glioma than in normal astrocytes. These factors may contribute to the greater level of VSV infection found in glioma.

Example 17

VSV-rp30 Targets Colon Cancer in Mouse

Materials and Methods
Mouse Procedures

Animal experiments were performed in accordance with institutional guidelines of the Yale University Animal Care and Use Committee. Immunodeficient NCr-Nude mice (NCr-Foxnlnu) were obtained from Taconic Farms (Germantown, N.Y.). Six to eight-week-old mice were briefly anesthetized by i.p. injection using a combination of ketamine and xylazine (100 and 10 mg/kg, respectively) and injected in both flanks with 500,000 HCT116 cells suspended in 0.1 ml sterile saline. Sizeable subcutaneous tumors formed within 3 weeks. Tumor bearing mice received a single tail vein injection of 0.1 ml of virus solution containing $5\times10^6$ pfu VSV-rp3O. Body weight and mouse health were monitored daily. Three days post VSV inoculation mice were sacrificed by an overdose of pentobarbital and perfused transcardially with physiological saline for 1 minute followed by freshly prepared 4% paraformaldehyde solution. Subcutaneous tumor masses and control tissues (liver, spleen, and lung) were excised, stored in 4% paraformaldehyde solution, and cut in 20-μm sections using a microtome. Cryosections were mounted using 4',6-diamidino-2-phenylindole (DAPI (Invitrogen) and analyzed on a fluorescence microscope (Olympus Optical IXT1; Tokyo, Japan) coupled to a SPOT color camera (Diagnostic Instruments, Sterling Heights, Mich.).

Results

It has been shown that VSV-rp30 is oncolytic in vivo using U-87 brain tumor xenograft mouse models employing two different virus application strategies, direct intratumoral injection (34) as well as systemic injection (20). To test the ability of VSV-rp30 to infect non-brain tumor cells in vivo, a HCT116 human colon carcinoma xenograft model was used. Four immunocompromised NCr nude mice bearing bilateral subcutaneous human HCT116 tumors received a single bolus of 100 μl of saline containing $5\times10^6$ pfu VSV-rp30 via tail vein injection. Mouse body weight showed a transient decrease after VSV injection, but recovered to pre-application values at 2 dpi. Tumors were harvested 3 days post inoculation and microscopic analysis revealed wide spread virus dissemination throughout the tumor masses. Importantly, viral GFP expression was restricted to the tumor mass and did not extend into the surrounding subcutaneous tissue. High magnification revealed the characteristic plasma membrane fluorescence of the GFP signal based on the unique viral G-GFP-fusion protein. During the viral replication cycle, viral G-protein incorporates into the cellular membrane. In contrast, analysis of control tissue from liver, spleen, and lung showed no GFP signal, thus indicating a lack of infection by VSV-rp30. In addition, no GFP signal was detected in tumors from mice (n=2) that did not receive virus injection. Together, these data indicate that VSV-rp30 can be applied systemically and target and infect tumor xenografts remote from the injection site with a striking preference for tumor tissue over normal control tissue.

As a proof of principle test that the in vitro data suggesting VSV-rp30 is oncolytic to many types of cancer may generalize to the whole animal, human colon cancer tumor cells were transplanted into mice. Intravenous injections of VSV-rp30 resulted in selective infection and cell death of the tumor, with relatively little detectable infection of normal cells. The in vivo experiment suggests that the tissue culture experiments may generalize to in vivo situations.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An isolated oncolytic VSV virus comprising one or more changes in nucleic acid sequence resulting in substitution of the serine at codon 126 of SEQ ID NO. 3, with an amino acid selected from the group consisting of alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), tryptophan (W), or valine (V) and substitution of aspartic acid (D) at codon 223 of SEQ ID NO. 5 with an amino acid selected from the group consisting of serine (S), threonine (T), or tyrosine (Y).

2. The isolated oncolytic VSV virus of claim 1, wherein the serine (S) at codon 126 SEQ ID NO. 3, is substituted with leucine (L) and the aspartic acid (D) at codon 223 of SEQ ID NO. 5 is substituted with a tyrosine (Y).

3. An isolated oncolytic VSV virus with SEQ ID NO: 6.

4. The isolated oncolytic VSV virus of claim 1, wherein the virus is engineered to express one or more additional genes encoding proteins selected from the group consisting of targeting proteins and therapeutic proteins.

5. A sterile pharmaceutical dosage unit composition comprising an effective amount of the oncolytic virus of claim 1 to reduce tumor burden.

6. The dosage unit of claim 5, in an amount of virus effective to systemically treat an individual having metastastic cancer.

7. The dosage unit of claim 5, comprising an amount of virus effective to locally or regionally treat a tumor.

8. A method for treating cancer comprising administering to a subject in need thereof an effective mount of the viral dosage unit of claim 5.

9. The method of claim 8, wherein the cancer is selected from the group consisting of bone, bladder, brain, breast, cervical, colo-rectal, esophageal, kidney, liver, lung, nasopharangeal, pancreatic, prostate, skin, stomach, and uterine.

10. The method of claim 8, wherein the cancer is a vascular cancer such as multiple myeloma, an adenocarcinomas or a sarcoma.

11. The method of claim 9, comprising administering a viral dosage unit effective to treat a glioma.

12. The method of claim 8, wherein the viral dosage unit is administered intratumorally or parenterally.

13. The method of claim 8, wherein the viral dosage unit is administered in combination with a second therapeutic agent selected from the group consisting of immunosuppressants, anticancer agents, and therapeutic proteins.

* * * * *

UNITED STATES PATENT AND TRADEMARK OFFICE
CERTIFICATE OF CORRECTION

Page 1 of 1

PATENT NO. : 8,481,297 B2
APPLICATION NO. : 12/683973
DATED : July 9, 2013
INVENTOR(S) : Anthony N. van den Pol and Guido Wollmann It is certified that error appears in the above-identified patent and that said Letters Patent is hereby corrected as shown below:

In the Specification

Column 1, Lines 15-18, replace "The United States government has certain rights in this invention by virtue of National Institutes of Health Grant Numbers 5RO1CA124737-03 and 5RO1AI048854-09 to Anthony N. van den Pol" with --This invention was made with government support under AI048854 and CA124737 awarded by the National Institutes of Health. The government has certain rights in the invention.--.

Signed and Sealed this
Nineteenth Day of May, 2020

Andrei Iancu
*Director of the United States Patent and Trademark Office*